US010259877B2

(12) United States Patent
Sun et al.

(10) Patent No.: US 10,259,877 B2
(45) Date of Patent: Apr. 16, 2019

(54) METHODS FOR TREATING OR PREVENTING MIGRAINE HEADACHE

(71) Applicant: AMGEN INC., Thousand Oaks, CA (US)

(72) Inventors: Hong Sun, Agoura Hills, CA (US); Eduardo Dunayevich, San Diego, CA (US); Robert A. Lenz, Westlake Village, CA (US); Gabriel Vargas, Berkeley, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/136,736

(22) Filed: Apr. 22, 2016

(65) Prior Publication Data
US 2016/0311913 A1 Oct. 27, 2016

Related U.S. Application Data

(60) Provisional application No. 62/152,708, filed on Apr. 24, 2015.

(51) Int. Cl.
A61K 39/00 (2006.01)
C07K 16/28 (2006.01)

(52) U.S. Cl.
CPC .... C07K 16/2869 (2013.01); A61K 2039/505 (2013.01); A61K 2039/545 (2013.01); C07K 2317/21 (2013.01); C07K 2317/76 (2013.01)

(58) Field of Classification Search
CPC ............ C07K 16/2869; C07K 2317/76; C07K 2317/92; C07K 2317/56; C07K 2317/565; C07K 2317/51; C07K 2317/515; C07K 2317/21; C07K 2317/24; A61K 2039/505; A61K 2039/545; A61M 5/20; A61M 5/24; A61M 5/28
See application file for complete search history.

(56) References Cited

U.S. PATENT DOCUMENTS

| 5,866,124 | A | 2/1999 | Hardman et al. | |
|---|---|---|---|---|
| 7,193,070 | B2 | 3/2007 | Kane et al. | |
| 7,288,251 | B2 | 10/2007 | Bedian et al. | |
| 7,423,128 | B2 | 9/2008 | Gazit-Bornstein et al. | |
| 7,658,924 | B2 | 2/2010 | Oliner et al. | |
| 9,072,777 | B2 | 7/2015 | Shindo | |
| 9,862,771 | B2 | 1/2018 | Boone et al. | |
| 9,896,502 | B2 * | 2/2018 | Bigal | C07K 16/18 |
| 2002/0164707 | A1 | 11/2002 | Adamou et al. | |
| 2004/0110170 | A1 | 6/2004 | Pisegna et al. | |
| 2004/0132101 | A1 | 7/2004 | Lazar et al. | |
| 2004/0176577 | A1 | 9/2004 | Rojer et al. | |
| 2005/0282252 | A1 | 12/2005 | Siegel et al. | |
| 2006/0018909 | A1 | 1/2006 | Oliner et al. | |
| 2006/0246071 | A1 | 11/2006 | Green et al. | |
| 2008/0057063 | A1 | 3/2008 | Rinkenberger et al. | |
| 2009/0220489 | A1 * | 9/2009 | Zeller | C07K 16/18 424/130.1 |
| 2012/0014968 | A1 * | 1/2012 | Walsh | C07K 16/22 424/158.1 |
| 2015/0266948 | A1 | 9/2015 | Bigal et al. | |
| 2015/0322142 | A1 | 11/2015 | Bigal et al. | |
| 2015/0376286 | A1 | 12/2015 | Boone et al. | |

FOREIGN PATENT DOCUMENTS

| JP | 2005/503809 | 2/2005 |
|---|---|---|
| JP | 2007-525495 A | 9/2007 |
| WO | 98/03534 A1 | 1/1998 |
| WO | 02/066492 A2 | 8/2002 |
| WO | 2004/014351 A2 | 2/2004 |
| WO | 03/027252 A2 | 11/2004 |
| WO | 2004/097421 A2 | 11/2004 |
| WO | 2005/077072 A2 | 8/2005 |
| WO | 2006/068953 A2 | 6/2006 |
| WO | 2006/134692 A1 | 12/2006 |
| WO | 2007/045927 A2 | 4/2007 |
| WO | 2007/048026 A2 | 4/2007 |
| WO | 2007/054809 A2 | 5/2007 |
| WO | 2007/076336 A1 | 7/2007 |
| WO | 2008/132453 A1 | 11/2008 |
| WO | 2009/109908 A1 | 9/2009 |
| WO | 2010/012911 A1 | 2/2010 |
| WO | 2010/075238 A1 | 7/2010 |
| WO | 2011/024113 A1 | 3/2011 |
| WO | 2012/162257 A2 | 11/2012 |

OTHER PUBLICATIONS

Bendig, M. M. (199.'3). Humanization of rodent monoclonal antibodies by CDR grafting. Methods-Companion to Methods in Enzymology, 8(2), 83-93.
Chauhan, M. et al. (2004), "Studies on the effects of the N-terminal domain antibodies of calcitonin receptor-like receptor and receptor activity-modifying protein 1 on calcitonin gene-related peptide-induced vasorelaxation in rat uterine artery", Biol.Reproduction, 70:1658-1663.
Colman, P.M. (1994), "Effects of amino acid sequence changes on antibody-antigen interactions", Research in Immunology, 145:33-36.
Corvera, Carlos U. et al. (2005), "Localization of calcitonin receptor-like receptor (CLR) and calcitonin gene-related peptide (CGRP) in human gut", Database Biosis, Ann. Mtg. Amer. Gastroenterol. Assoc./Digestive Disease Wk., Chicago, IL, 128(4, S2):A361.
Cottrell et al. (2005), "Localization of calcitonin receptor-like receptor and receptor activity modifying protein 1 in enteric neuron, dorsal root ganglia and the spinal cord of the rat", J. Comparative Neurol. 490:239-255.

(Continued)

Primary Examiner — Kimberly Ballard
(74) Attorney, Agent, or Firm — Angela L. Purcell

(57) ABSTRACT

The present invention relates to methods of migraine prophylaxis using anti-CGRP receptor antibodies or binding fragments. In particular, methods for preventing or reducing the occurrence of migraine headache in a patient in need thereof comprising administering to the patient an anti-CGRP receptor or binding fragment according to specific dosage regimens are disclosed. Pharmaceutical compositions and administration devices comprising anti-CGRP receptor antibodies or binding fragments for use in the methods are also described.

58 Claims, 9 Drawing Sheets
Specification includes a Sequence Listing.

(56) References Cited

OTHER PUBLICATIONS

Davis et al. (2008), "The tortuous road to an ideal CGRP function blocker for the treatment of migraine", Current Topics in Med. Chem., 8(16)1468-1479.
Dong, Yuan-Lin et al. (2004), "Involvement of calcitonin gene-related peptide in control of human fetoplacental vascular tone", Amer. J. Physiol. Heart Circulation Physiol., 286:H230-H239.
Durham et al. (2004), "CGRP-receptor antagonists—a fresh approach to migraine therapy?", N. Eng. J. Med., 350(11):1073-1075.
Evans et al. (2000), "CGRP-RCP, a novel protein required for signal transduction at calcitonin gene-related peptide and adrenomedullin receptors", J. Biol. Chem., 275(40):31438-31443.
Hay, D.L. (2007), "What makes a $CGRP_2$ receptor?", Clin. Exper. Pharmacol. Physiol., 34:963-971, doi:10.1111/j.1440-1681.2007.04703.x.
Kuwasako et al. (2000), "Visualization of the calcitonin receptor-like receptor and its receptor activity-modifying proteins during internalization and recycling", J. Biol. Chem., 275(28):29602-29609.
Lennerz et al. (2008), "Calcitonin receptor-like receptor (CLR), receptor activity-modifying protein 1 (RAMP1), and calcitonin gene-related peptide (CGRP) immunoreactivity in the rat trigeminovascular system: differences between peripheral and central CGRP receptor distribution", J. Comparative Neurol., 507(3):1277-1299.
Mach et al. (2002), "Origins of skeletal pain: sensory and sympathetic innervation for the mouse femur", Neurosci., 113(1):155-166.
Paul, William E. (ed.), (1993), Fundamental Immunology, $3^{rd}$ ed., Raven Press, New York, 9:292-295.
Poyner et al. (2002), "International union of pharmacology, XXXII. The mammalian calcitonin gene-related peptides, adrenomedullin, amylin, and calcitonin receptors", Pharmacol. Rev., 54(2).
Rudikoff, Stuart et al. (1982), "Single amino acid substitution altering antigen-binding specificity", PNAS USA, 79(6):1979-1983.
Taylor, Christopher K. et al. (2006), "Pharmacological characterization of novel α-calcitonin gene related peptide (CGRP) receptor peptide antagonists that are selective for human CGRP receptors", J. Pharmacol. Exper. Therap., 319(2):749-757.
Wimalawansa et al. (1989), "Isolation, purification and raising of monoclonal antibodies for calcitonin gene-related peptide (CGRP) receptor", Reg. Peptides, 26(1).
Zeller, J. et al. (2008), "CGRP function-blocking antibodies inhibit neurogenic vasodilatation without affecting heart rate or arterial blood pressure in the rat", British J. Pharmacol., 155(7):1093-1103.
Edvinsson, Lars and Ho, Tony W. (2010), "CGRP receptor antagonism and migraine", Neurotherap., 7(2):164-175.
McAllister, Peter (Mar. 7, 2015), "CGRP Research in 2015: Where are we now and where are we going?" The $25^{th}$ Annual Headache Symposium, HCNE Headache Cooperative of New England, Presentation.
Vecsei, Laszlo et al. (2015), "CGRP antagonists and antibodies for the treatment of migraine", Expert Opin. Invest. Drugs, 24(1):31-41.
Walter, Sarah and Bigal, Marcelo E. (2015), "TEV-48125: A review of a monoclonal CGRP antibody in development for the preventive treatment of migraine", Curr. Pain Headache Rep., 19(6):1-6.
PCT/US2015/044479 (Oct. 19, 2015) International Search Report and Written Opinion.
Committee on Methods of Producing Monoclonal Antibodies (1999), "Monoclonal antibody production", National Academy Press, Washington DC.
Durham, Paul L. (2008), "Inhibition of calcitonin gene-related peptide function: a promising strategy for treating migraine", Headache, 48:1269-1275.
McLatchie, L.M. et al. (1998), "RAMPs regulate the transport and ligand specificity of the calcitonin-receptor-like receptor", Nature, 393:333-339.
Tepper et al. (2017), "Safety and efficacy of erenumab for preventive treatment of chronic migraine: a randomised, double-blind, placebo-controlled phase 2 trial", Lancet Neurol., 16:425-434.
Ashina et al. (2000), "Plasma levels of calcitonin gene-related peptide in chronic tension-type headache", Neurol. 55(9):1335-1340.
Bennett et al. (2000), "Alleviation of mechanical and thermal allodynia by $CGRP_{8-37}$ in a rodent model of chronic central pain", Pain, 86(1-2):163-175.
The International Classification of Headache Disorders, $2^{nd}$ ed. (2004), Cephalalgia, 24(Suppl. 1):9-160.
Wyon et al. (2000), "Concentrations of calcitonin gene-related peptide and neuropeptide Y in plasma increase during flushes in postmenopausal women", Menopause, 7(1):25-30.
Calcitonin receptor-like [Homo sapiens], NCBI Ref. Seq.: NP 005786.1 (Feb. 3, 2008).
Receptor activity-modifying protein 1 precursor [Homo sapiens] NCBI Ref Seq.: NP 005846.1 (Feb. 3, 2008).
Ashina et al. (1999), "Plasma levels of substance P, neuropeptide Y and vasoactive intestinal polypeptide in patients with chronic tension-type headache", Pain, 83:541-547.
Berglund et al. (2008), "The epitope space of the human proteome", Protein Sci., 17:606-613.
Goadsby et al. (2017), "A controlled trial of erenumab for episodic migraine", N. Engl. J. Med., 377(22):2123-2132.
Greenspan et al. (1999), "Defining epitopes: It's not as easy as it seems", Nature Biotech., 17:936-937.
Jiang et al. (2005), "A novel peptide isolated from a phage display peptide library with trastuzumab can mimic antigen epitope of HER-2*", J. Biol. Chem., 280(6):4656-4662.
Perena, M.J. et al. (2000), "Neuroanatomia del dolor", Rev. Soc. Esp. Dolor, 7(Supl II): 5-10.
Perena, M.J. et al. (2000), "Neuroanatomia del dolor", Rev. Soc. Esp. Dolor, 7(Supl II): 5-10. * Machine Translation into English.
Stancoviski et al. (1991), "Mechanistic aspects of the opposing effects of monoclonal antibodies to the ERBB2 receptor on tumor growth", PNAS USA, 88:8691-8695.
Wang, W. et al. (2008), "Monoclonal antibody pharmacokinetics and pharmacodynamics", Clin. Pharmacol. Therap., 84(5):548-558.
Bigal and Walter (2014), "Monoclonal antibodies for migraine: preventing calcitonin gene-related peptide activity," CNS Drugs, 28:389-399.
Deng et al. (2012), "Monoclonal antibodies: what are the pharmacokinetic and pharmacodynamic considerations for drug development?", Expert Opin. Drug Metab. Toxicol., 8(2):141-160.
Goadsby et al. (1990), "Vasoactive peptide release in the extracerebral circulation of humans during migraine headache", Ann. Neurol., 28:183-187.
Walker and Hay (2013), "CGRP in the trigeminovascular system: a role for CGRP, adrenomedullin and amylin receptors?", British J. Of Pharmacol., 170:1293-1307.

* cited by examiner

METHODS FOR TREATING OR PREVENTING MIGRAINE HEADACHE

CROSS-REFERENCE TO RELATED APPLICATIONS

This application claims the benefit of U.S. Provisional Application No. 62/152,708, filed Apr. 24, 2015, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Apr. 22, 2016, is named A-1945-US-NP_ST25.txt and is 140 kilobytes in size.

FIELD OF THE INVENTION

The present invention relates to the fields of neurology and biopharmaceuticals. In particular, the invention relates to prophylactic treatment of migraines using an antibody that selectively inhibits the human calcitonin gene-related peptide (CGRP) receptor.

BACKGROUND OF THE INVENTION

Migraine is a complex, common neurological condition that is characterized by severe, episodic attacks of headache and associated features, which may include nausea, vomiting, sensitivity to light, sound or movement. In some patients, the headache is preceded or accompanied by sensory warning signs or symptoms (i.e. auras). The headache pain may be severe and may also be unilateral in certain patients. Migraine attacks are disruptive to daily life and cost billions of dollars each year in missed work days and impaired performance (Modi and Lowder, Am. Fam. Physician, Vol. 73:72-78, 2006).

Migraine is a highly prevalent disease worldwide with approximately 15% of the European population and 12% of the United States population suffering from migraine attacks (Lipton et al, Neurology, Vol. 68:343-349, 2007). Additionally, migraines have been found to be associated with a number of psychiatric and medical comorbidities such as depression and vascular disorders (Buse et al., Neurol. Neurosurg. Psychiatry, Vol. 81:428-432, 2010; Bigal et al., Neurology, Vol. 72:1864-1871, 2009).

Migraine headache is commonly treated acutely, primarily with analgesics and a class of drugs called triptans (Humphrey et al. Ann NY Acad Sci., Vol. 600:587-598, 1990; Houston and Vanhoutte, Drugs, Vol. 31:149-163 1986). The triptans, which are selective serotonin 5-HT1B/1D agonists, are effective drugs for acute migraine and are generally well tolerated, but are contraindicated in the presence of cardiovascular disease due to their potential for coronary vasoconstriction. In addition, many migraine patients do not respond favorably to triptans. In a meta-analysis of 53 trials, up to a third of all people with migraine and 40% of all migraine attacks did not respond to triptans (Ferrari et al., Lancet, Vol. 358:1668-1675, 2001).

Migraine prophylaxis is an area of large unmet medical need. Approximately 40% of the migraine patient population would benefit from preventive therapy (Lipton et al., Neurology, Vol. 68:343-349, 2007). However, only approximately 12% of patients receive any preventive therapy due in part to limited efficacy and significant tolerability and safety issues with available preventive therapies. Topiramate, an anticonvulsant that blocks voltage-dependent sodium channels and certain glutamate receptors (AMPA-kainate), is the medication most often used for migraine prophylaxis in the United States. Topiramate is the only migraine prophylactic agent with demonstrated efficacy in both episodic and chronic migraine patients through randomized placebo-controlled trials (Diener et al., Cephalalgia, Vol. 27:814-823, 2007; Silberstein et al., Headache, Vol. 47:170-180, 2007). However, approximately 50% of patients fail to respond to topiramate and it is poorly tolerated. Common adverse events associated with topiramate treatment include paresthesia, anorexia, and cognitive adverse events, including psychomotor slowing, somnolence, language difficulties, and difficulties with memory and concentration (Brandes et al., JAMA, Vol. 291:965-973, 2004; Adelman et al., Pain Med., Vol. 9:175-185 2008; Silberstein et al., Arch Neurol., Vol. 61:490-495, 2004). In an open-label, flexible-dose study, 20% of patients withdrew from topiramate because of adverse effects (Nelles et al., Headache, Vol. 49:1454-1465, 2009).

Thus, migraine sufferers have an urgent medical need for more effective and/or tolerable treatment options.

SUMMARY OF THE INVENTION

The present invention is based, in part, on the identification of a therapeutic regimen for effectively reducing the frequency, severity and/or duration of migraine headache in patients in need thereof with no or minimal adverse side effects. Accordingly, in one embodiment, the present invention provides a method for preventing or reducing the occurrence of migraine headache in a patient in need thereof comprising administering to the patient an anti-CGRP receptor antibody or antigen-binding fragment thereof at a dose of about 35 mg to about 210 mg per month. In some embodiments, the present invention provides a method for prophylactically treating a patient for migraine comprising administering to the patient an anti-CGRP receptor antibody or antigen-binding fragment thereof at a dose of about 35 mg to about 210 mg per month.

In some embodiments of the methods, the anti-CGRP receptor antibody or binding fragment thereof is administered to the patient at a dose sufficient to reduce the number of monthly migraine headache days experienced by the patient as compared to the number of monthly migraine headache days prior to treatment or the number of monthly migraine headache days experienced by a patient not receiving the anti-CGRP receptor antibody or binding fragment thereof. In some embodiments, the dose of anti-CGRP receptor antibody or binding fragment thereof administered to the patient is sufficient to reduce the number of monthly migraine headache days in the patient by at least 50% as compared to the number prior to treatment or the number experienced by a patient not receiving the anti-CGRP receptor antibody or binding fragment thereof.

In certain embodiments of the methods, the anti-CGRP receptor antibody or binding fragment thereof is administered to the patient at a dose sufficient to reduce the number of monthly migraine headache hours experienced by the patient as compared to the number of monthly migraine headache hours prior to treatment or the number of monthly migraine headache hours experienced by a patient not receiving the anti-CGRP receptor antibody or binding fragment thereof. In certain other embodiments of the methods, the anti-CGRP receptor antibody or binding fragment thereof is administered to the patient at a dose sufficient to reduce the number of monthly migraine-specific medication use days experienced by the patient as compared to the number of monthly migraine-specific medication use days prior to treatment or the number of monthly migraine-specific medication use days experienced by a patient not receiving the anti-CGRP receptor antibody or binding fragment thereof.

In some embodiments of the methods, the anti-CGRP receptor antibody or binding fragment thereof is administered to the patient at a dose sufficient to reduce the number of days of physical impairment due to migraine headaches in the patients as compared to the number prior to treatment or to the number experienced by a patient not receiving the anti-CGRP receptor antibody or binding fragment thereof. In other embodiments, the anti-CGRP receptor antibody or binding fragment thereof is administered to the patient at a dose sufficient to reduce the impact of migraine headache on everyday activities as compared to the impact prior to treatment or to the impact experienced by a patient not receiving the anti-CGRP receptor antibody or binding fragment thereof. Physical impairment due to migraine headache and the impact of the migraine headache on everyday activities can be assessed using a number of validated questionnaires as described herein.

In certain embodiments of the methods, a dose sufficient to reduce the number of monthly migraine headache days, number of monthly migraine headache hours, number of monthly migraine-specific use days, physical impairment due to migraine, and/or impact of migraine on everyday activities in a patient in need thereof is about 35 mg to about 210 mg per month. In some embodiments, the sufficient dose is about 70 mg to about 140 mg per month. In one particular embodiment, the sufficient dose is about 70 mg per month. In another particular embodiment, the sufficient dose is about 140 mg per month. In these and other embodiments, the dose of anti-CGRP receptor antibody or binding fragment thereof is administered once a month (QM).

In some embodiments of the methods, administration of the anti-CGRP receptor antibody or binding fragment thereof at the dosages described herein does not substantially cause an adverse side effect in the patient. In particular, administration of the anti-CGRP receptor antibody or binding fragment thereof at the dosages described herein does not substantially cause an adverse side effect associated with other migraine prophylactic treatments, including adverse side effects associated with antiepileptics, beta-blockers, and anti-depressants. In certain embodiments, the number and type of adverse side effects associated with administration of the anti-CGRP receptor antibody or binding fragment is not statistically different than the number and type of adverse side effects associated with administration of placebo.

In certain embodiments of the methods described herein, the anti-CGRP receptor antibody or binding fragment thereof is administered to the patient parenterally. In particular embodiments, the anti-CGRP receptor antibody or binding fragment thereof is administered to the patient by subcutaneous injection. In one embodiment, the subcutaneous injection is a bolus injection administered to the patient once a month. The subcutaneous injection may be delivered to the patient with a pre-filled syringe or autoinjector containing a monthly dose of the anti-CGRP receptor antibody or binding fragment thereof.

In some embodiments, the patients to be administered the anti-CGRP receptor antibody or binding fragment thereof according to the methods of the invention have or have been diagnosed with episodic migraine. The episodic migraine may be low-frequency episodic migraine or high-frequency episodic migraine. In other embodiments, the patients to be administered the anti-CGRP receptor antibody or binding fragment thereof according to the methods of the invention have or have been diagnosed with chronic migraine.

In certain embodiments of the methods of the invention, the patients to be administered the anti-CGRP receptor antibody or binding fragment thereof have not previously received any prophylactic therapy for migraine headache (i.e. the patients are treatment-naïve). In other embodiments of the methods of the invention, the patients to be administered the anti-CGRP receptor antibody or binding fragment thereof have failed or are intolerant to at least one other migraine prophylactic therapy. Thus, the patients to be administered the anti-CGRP receptor antibody or binding fragment thereof have, in some embodiments, failed or are intolerant to at least one antiepileptic (e.g. topiramate, valproic acid), tricyclic antidepressant (e.g., amitriptyline), beta-blocker (e.g., propranolol, timolol), or botulinum toxin A. In one embodiment, the patient has failed or is intolerant to two prior migraine prophylactic therapies. In another embodiment, the patient has failed or is intolerant to three prior migraine prophylactic therapies.

In any embodiments of the methods disclosed herein, the anti-CGRP receptor antibody or antigen-binding fragment thereof specifically binds to an epitope formed from amino acids in both human CRLR and human RAMP1 polypeptide components of the human CGRP receptor and selectively inhibits the human CGRP receptor as compared to the human AM1, AM2, and/or amylin receptors. In some embodiments, the anti-CGRP receptor antibody or antigen-binding fragment specifically binds to the human CGRP receptor with a $K_D \leq 100$ nM. In other embodiments, the anti-CGRP receptor antibody or antigen-binding fragment specifically binds to the human CGRP receptor with a $K_D \leq 10$ nM.

In one embodiment, the anti-CGRP receptor antibody or antigen-binding fragment thereof administered to the patient according to the methods of the invention comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65. In another embodiment, the anti-CGRP receptor antibody or antigen-binding fragment thereof administered to the patient according to the methods of the invention comprises a CDRH1 having the sequence of SEQ ID NO:15, a CDRH2 having the sequence of SEQ ID NO:29, a CDRH3 having the sequence of SEQ ID NO:35, a CDRL1 having the sequence of SEQ ID NO:45, a CDRL2 having the sequence of SEQ ID NO:61, and a CDRL3 having the sequence of SEQ ID NO:66.

The anti-CGRP receptor antibody or binding fragment thereof suitable for use in the methods of the invention can comprise a heavy chain variable region comprising the sequence of SEQ ID NO: 92 and a light chain variable region comprising the sequence of SEQ ID NO: 80. In some embodiments, the anti-CGRP receptor antibody or binding fragment thereof used in the methods of the invention comprises a heavy chain variable region comprising the sequence of SEQ ID NO: 98 and a light chain variable region comprising the sequence of SEQ ID NO: 84. In certain embodiments, the anti-CGRP receptor antibody has a human IgG1 constant region or a human IgG2 constant region. In one embodiment, the anti-CGRP receptor antibody comprises a heavy chain comprising the sequence of SEQ ID NO:105, and a light chain comprising the sequence of SEQ ID NO:123. In another embodiment, the anti-CGRP receptor antibody comprises a heavy chain comprising the sequence of SEQ ID NO:111, and a light chain comprising the sequence of SEQ ID NO:127.

Any of the specific antibodies described in Table 7 herein or antigen-binding fragments thereof can be used in the methods of the invention. In certain embodiments, the anti-CGRP receptor antibody or binding fragment administered to a patient according to the methods of the invention is the 4E4 antibody or binding fragment thereof. In other embodiments, the anti-CGRP receptor antibody or binding fragment administered to a patient according to the methods of the invention is the 9F5 antibody or binding fragment thereof.

The present invention also provides pharmaceutical compositions of anti-CGRP receptor antibodies or binding fragments thereof for use in the methods described herein. The pharmaceutical compositions can comprise one or more pharmaceutically acceptable diluents, carriers, or excipients, including buffers, surfactants, and stabilizing agents. In certain embodiments, the pharmaceutical compositions comprise an anti-CGRP receptor antibody or binding fragment thereof, a buffer, a surfactant, and a stabilizing agent. In one embodiment, the pharmaceutical composition comprises an anti-CGRP receptor antibody or binding fragment thereof, an acetate buffer, polysorbate 20 or polysorbate 80, and sucrose. Any of the pharmaceutical compositions described herein can be incorporated into self-administration devices, such as pre-filled syringes or autoinjectors, for administration (e.g. subcutaneous administration) to a patient according to the methods described herein.

Thus, the present invention also includes a pre-filled syringe or autoinjector for use in prophylactically treating migraine headache in a patient in need thereof comprising a pharmaceutical composition comprising an anti-CGRP receptor antibody or binding fragment thereof, an acetate buffer, sucrose, and polysorbate. In some embodiments, the pre-filled syringe or autoinjector comprises a pharmaceutical composition comprising about 70 mg/ml to about 140 mg/ml of anti-CGRP receptor antibody or binding fragment thereof, about 10 mM to about 15 mM sodium acetate, about 0.008% to about 0.012% w/v polysorbate, and about 8% to about 9% w/v sucrose at a pH of about 4.8 to about 5.5. In certain embodiments, the injection volume of the pre-filled syringe or autoinjector is about 1 ml or less.

In some embodiments, the present invention also provides kits comprising a pharmaceutical composition or self-administration device disclosed herein and instructions for using the pharmaceutical composition or self-administration device for delivering a therapeutically effective dose, for example, by subcutaneous injection for prophylactically treating migraine headache in a patient in need thereof. In embodiments in which the pharmaceutical composition is provided in a lyophilized or dry powder form, the kit may comprise a diluent and instructions for reconstituting the pharmaceutical composition prior to administration.

The use of anti-CGRP receptor antibodies or binding fragments thereof in any of the methods disclosed herein or for preparation of medicaments for administration according to any of the methods disclosed herein is specifically contemplated. For instance, the present invention includes an anti-CGRP receptor antibody or binding fragment thereof for use in a method for preventing or reducing the occurrence of migraine headache in a patient in need thereof, wherein the method comprises administering to the patient an anti-CGRP receptor antibody or binding fragment thereof at a dose of about 35 mg to about 210 mg per month. The present invention also includes an anti-CGRP receptor antibody or binding fragment thereof for use in a method for prophylactically treating a patient for migraine headache, wherein the method comprises administering to the patient an anti-CGRP receptor antibody or binding fragment thereof at a dose of about 35 mg to about 210 mg per month.

The present invention also includes the use of an anti-CGRP receptor antibody or binding fragment thereof in the preparation of a medicament for preventing or reducing the occurrence of migraine headache in a patient in need thereof, wherein the anti-CGRP receptor antibody or binding fragment is at a dose of about 35 mg to about 210 mg per month. The present invention further includes the use of an anti-CGRP receptor antibody or binding fragment thereof in the preparation of a medicament for prophylactically treating a patient for migraine headache, wherein the anti-CGRP receptor antibody or binding fragment is at a dose of about 35 mg to about 210 mg per month.

DETAILED DESCRIPTION

Figure 1:
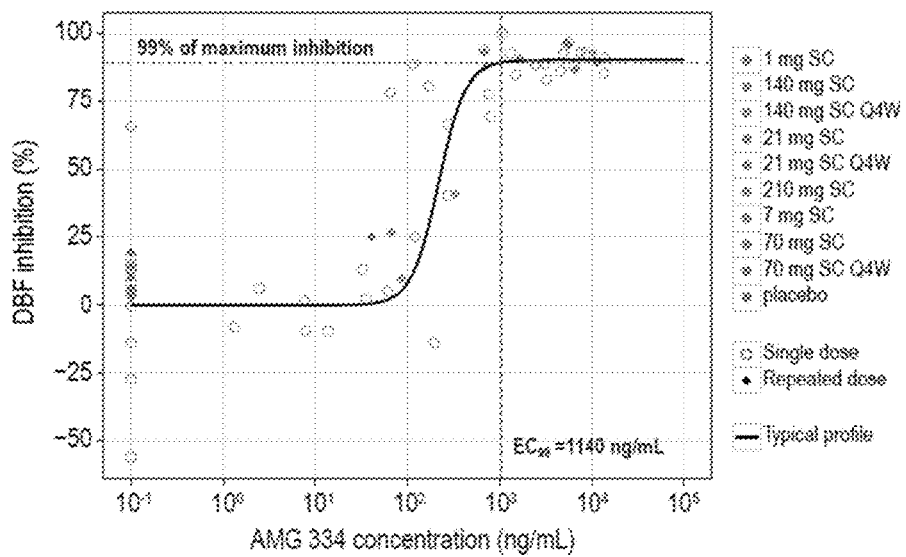
FIG. 1 depicts the percentage inhibition of capsaicin-induced dermal blood flow (DBF) in healthy human subjects and migraine patients as a function of serum concentration of AMG 334 monoclonal antibody.

Currently available therapies for treating migraine headache in human patients have a poor risk-benefit profile due to adverse side effects, which many patients are unable or refuse to tolerate. The present invention addresses this problem, in part, by providing a novel regimen of anti-CGRP receptor antibodies that provides effective migraine prophylaxis with no or minimal side effects. The methods of the invention described herein can effectively reduce the frequency, severity, and/or duration of migraine headache in patients suffering from episodic migraine as well as chronic migraine.

Migraine headaches are recurrent headaches lasting about 4 to about 72 hours that are characterized by unilateral, pulsating, and/or moderate to severe pain and/or pain that is exacerbated by physical activity. Migraine headaches are often accompanied by nausea, vomiting, and/or sensitivity to light (photophobia), sound (phonophobia), or smell. In some patients, an aura precedes the onset of the migraine headache. The aura is typically a visual, sensory, language, or motor disturbance that signals the headache will soon occur. The methods described herein prevent, treat, or ameliorate one or more symptoms of migraine headaches with and without aura in human patients.

In one embodiment, the present invention provides a method for preventing or reducing the occurrence of migraine headache in a patient in need thereof comprising administering to the patient a pharmaceutical composition comprising a therapeutically effective amount of an anti-CGRP receptor antibody or antigen-binding fragment thereof. The term "patient" includes human patients. As used herein, "preventing or reducing the occurrence of migraine headache" refers to a reduction in the frequency, duration, or severity of the migraine headache as compared to the frequency, duration, or severity of the migraine headache prior to administration of the composition or as compared to the frequency, duration, or severity of the migraine headache in a patient not administered the composition (i.e. a control subject). Thus, in certain embodiments, the present invention provides a method for prophylactically treating a patient for migraine headache comprising administering to the patient a pharmaceutical composition comprising a therapeutically effective amount of an anti-CGRP receptor antibody or antigen-binding fragment thereof. "Prophylactic treatment" refers to treatment designed to be taken before a migraine attack to reduce the frequency, severity, and/or length of migraine headaches in the patient. In some embodiments, a prophylactic treatment may increase the effectiveness of or a patient's response to acute migraine-specific medications.

In some embodiments of the methods of the invention, administration of the anti-CGRP receptor antibody or binding fragment thereof reduces the number of migraine headache days experienced by the patient over the course of a month compared to the number prior to administration of the anti-CGRP receptor antibody or binding fragment (i.e. pre-treatment baseline) and/or compared to the number experienced by a patient not receiving the anti-CGRP receptor antibody or binding fragment. A "migraine headache day" includes any calendar day during which a patient experiences the onset, continuation, or recurrence of a "migraine headache" with or without aura lasting greater than 30 minutes. A "migraine headache" is a headache associated with nausea or vomiting or sensitivity to light or sound and/or a headache characterized by at least two of the following pain features: unilateral pain, throbbing pain, moderate to severe pain intensity, or pain exacerbated by physical activity. The pre-treatment baseline can be established by determining the relevant parameter (e.g. number of migraine headache days) in one, two, three, four, five, or six or more months prior to administration of the anti-CGRP receptor antibody or binding fragment. In some embodiments, the pre-treatment baseline is established based on the measurement of the particular parameter in the three months prior to administration of the anti-CGRP receptor antibody or binding fragment.

In certain embodiments, the number of monthly migraine headache days experienced by the patient is reduced by about 10%, about 15%, about 20%, about 25%, about 30%, about 35%, about 40%, about 45%, about 50%, about 55%, or about 60% following administration of the anti-CGRP receptor antibody or binding fragment as compared to a pre-treatment baseline and/or a control subject (i.e. a patient not receiving the antibody or binding fragment). In some embodiments, the number of monthly migraine headache days experienced by the patient is reduced by 65% or more, for example, by at least about 70%, at least about 75%, or at least about 80% following administration of the anti-CGRP receptor antibody or binding fragment as compared to a pre-treatment baseline and/or a control subject. In one embodiment, the number of monthly migraine headache days experienced by the patient is reduced by at least 50% following administration of the anti-CGRP receptor antibody or binding fragment. In another embodiment, the number of monthly migraine headache days experienced by the patient is reduced by at least 75% following administration of the anti-CGRP receptor antibody or binding fragment.

A reduction in the occurrence of migraine headache can also be assessed as a reduction in the number of migraine headache hours experienced by the patient over the course of a month compared to a pre-treatment baseline and/or the number experienced by a patient not receiving the anti-CGRP receptor antibody or binding fragment. A "migraine headache hour" is any hour during which a patient experiences the onset, continuation, or recurrence of a "migraine headache" with or without aura. In certain embodiments, administration of the anti-CGRP receptor antibody or binding fragment thereof reduces the number of monthly migraine headache hours experienced by the patient by at least about 20%, at least about 30%, at least about 40%, at least about 50%, at least about 60%, or at least about 70% as compared to a pre-treatment baseline and/or the number in a control subject not receiving the anti-CGRP receptor antibody or binding fragment.

Efficacy of the therapeutic regimens described herein can also be assessed in terms of the number of days a patient requires acute treatment with migraine-specific medication, the number of days the patient is physically or functionally impaired due to migraine, or the number of migraine attacks experienced by the patient. For instance, in some embodiments, the administration of the anti-CGRP receptor antibody or binding fragment thereof reduces the number of days a patient requires the use of acute migraine treatments over the course of a month compared to a pre-treatment baseline and/or the number experienced by a patient not receiving the anti-CGRP receptor antibody or binding fragment. As used herein, the term "acute migraine-specific medication treatment day" or "acute migraine-specific medication use day" refers to any calendar day during which the patient took a medication that is specific for migraine. Acute migraine-specific medications include, but are not limited to, triptans (e.g., almotriptan, frovatriptan, rizatriptan, sumatriptan, naratriptan, eletriptan, and zolmitriptan), ergotamines (e.g., dihydroergotamine and ergotamine with caffeine), non-steroidal anti-inflammatory drugs (e.g., acetylsalicylic acid, ibuprofen, naproxen, indomethacin, and diclofenac), and opioids (e.g., codeine, morphine, hydrocodone, fentanyl, meperidine, and oxycodone). The number of monthly acute migraine-specific medication treatment days can be reduced by at least about 25%, at least about 30%, at least about 40%, at least about 50%, at least about 60%, at least about 70%, at least about 75%, at least about 80%, or at least about 85% following administration of the anti-CGRP receptor antibody or binding fragment thereof. In certain embodiments, administration of the anti-CGRP receptor antibody or binding fragment thereof completely eliminates the need for the use of acute migraine-specific medications.

In some embodiments, administration of an anti-CGRP receptor antibody or binding fragment thereof according to the methods described herein can reduce the physical impairment or quality-of-life impact scores reported by patients as compared to a pre-treatment baseline and/or a patient not receiving the anti-CGRP receptor antibody. Migraine headaches often impact the quality of life of patients and prevent them from engaging in leisure and everyday activities as well as cause a loss of productivity in a patient's job. These effects can be assessed using validated questionnaires and surveys, such as the modified Migraine Disability Assessment Questionnaire (MIDAS), the Headache Impact Test-6 (HIT-6), the Migraine-Specific Quality of Life Questionnaire (MSQ), the Migraine Functional Impact Questionnaire (MFIQ), and the Migraine Physical Function Impact Diary (MPFID). Thus, the methods of the invention improve one or more aspects of a patient's quality of life and/or reduce the impact of migraines on one or more aspects of a patient's physical, social, or emotional function as assessed by one or more of these questionnaires.

MIDAS is a 5-item self-administered questionnaire that sums the number of productive days lost over the past month in the workplace and the home. The MIDAS also assesses disability in family, social, and leisure activities. The MIDAS score is the sum of missed days due to a headache from paid work, housework, and non-work (family, social, leisure) activities; and days at paid work or house work where productivity was reduced by at least half. The score is categorized into 4 severity grades: Grade I=0-5 (defined as minimal or infrequent disability), Grade II=6-10 (mild or infrequent disability), Grade III=11-20 (moderate disability), and Grade IV=21 and over (severe disability). In certain embodiments, administration of anti-CGRP receptor antibody or binding fragment thereof according to the methods of the invention reduces a patient's MIDAS score (i.e. reduces the severity grade/reduces the frequency or severity of disability caused by migraine) as compared to the patient's score prior to treatment or to the score of a patient not receiving the anti-CGRP receptor antibody or binding fragment.

The MSQ is a self-administered 14-item instrument measuring (i) how migraines limit a patient's daily social and work-related activities (role function-restrictive), (ii) how migraines prevent these activities (role function-preventive), and (iii) the emotions associated with a patient's migraines (emotional function). Patients respond to items using a 6-point scale: "none of the time," "a little bit of the time," "some of the time," "a good bit of the time," "most of the time," and "all of the time," which are assigned scores of 1 to 6, respectively. Raw dimension scores are computed as a sum of item responses and rescaled from a 0 to 100 scale such that higher scores indicate better quality of life. In some embodiments, administration of an anti-CGRP receptor antibody or binding fragment thereof according to the methods of the invention increases a patient's score on the MSQ (i.e. the quality of the patient's life is improved) as compared to the patient's score prior to treatment or to the score of a patient not receiving the anti-CGRP receptor antibody or binding fragment.

The MFIQ is a self-administered 26-item instrument measuring the impact of migraine on broader functioning. Specifically, it measures the impact of a patient's migraines on physical functioning, usual activities, social functioning, and emotional functioning. Subjects respond to items using a 5-point scale assigned scores from 1 to 5, with 5 representing the greatest burden. The scores are calculated as the sum of the item responses and the sum is rescaled to a 0-100 scale, with higher scores representing greater burden. In certain embodiments, administration of an anti-CGRP receptor antibody or binding fragment thereof according to the methods of the invention decreases a patient's score on the MFIQ (i.e. the impact of migraine on a patient's functioning is reduced) as compared to the patient's score prior to treatment or to the score of a patient not receiving the anti-CGRP receptor antibody or binding fragment.

The MPFID is a self-administered 13-item instrument measuring physical functioning. It assesses impact on everyday activities and physical impairment. Subjects respond to items using a 5-point scale, with difficulty items ranging from "Without any difficulty" to "Unable to do" and frequency items ranging from "None of the time" to "All of the time." These are assigned scores from 1 to 5, with 5 representing the greatest burden. Scores are calculated as the sum of the item responses and the sum is rescaled to a 0-100 scale, with higher scores representing greater impact of migraine (i.e., higher burden). In some embodiments, administration of an anti-CGRP receptor antibody or binding fragment thereof according to the methods of the invention decreases a patient's score on the MPFID (i.e. the impact of migraine on a patient's physical functioning or everyday activities is reduced) as compared to the patient's score prior to treatment or to the score of a patient not receiving the anti-CGRP receptor antibody or binding fragment. In one particular embodiment, administration of an anti-CGRP receptor antibody or binding fragment thereof to a patient reduces the patient's physical impairment score by at least about 50% as compared to the patient's score prior to treatment or to a control subject (i.e. a subject not receiving the anti-CGRP receptor antibody or binding fragment). In some embodiments, the mean monthly days with physical impairment as measured by the MPFID is reduced in the patient following administration of an anti-CGRP receptor antibody or binding fragment thereof as compared to the number of days prior to treatment or the mean monthly days with physical impairment in a control subject. In another particular embodiment, administration of an anti-CGRP receptor antibody or binding fragment thereof to a patient reduces the patient's impact on everyday activities score as measured by the MPFID by at least about 50% as compared to the patient's score prior to treatment or to the score of a control subject. In some embodiments, the mean monthly days with impact on everyday activities as measured by the MPFID is reduced in the patient following administration of an anti-CGRP receptor antibody or binding fragment thereof as compared to the number of days prior to treatment or the mean monthly days with impact on everyday activities in a control subject.

In certain embodiments of the methods of the invention, the number of migraine attacks experienced by the patient is reduced following administration of an anti-CGRP receptor antibody or binding fragment thereof as compared to the number of migraine attacks experienced by the patient prior to treatment or the number of migraine attacks experienced by a control subject. As used herein, the term "migraine attack" refers to an episode of any migraine headache as defined herein. A migraine attack that is interrupted by sleep or temporarily remits and then recurs within 48 hours is generally considered to be a single attack. Similarly, a migraine attack that is successfully treated with acute migraine-specific medication but relapses within 48 hours is also considered to be a single attack. In some embodiments, the number of migraine attacks is reduced in the patient by at least about 25%, at least about 30%, at least about 40%, at least about 50%, at least about 60%, at least about 70%, or at least about 75% following administration of an anti-CGRP receptor antibody or binding fragment thereof as compared to the number of attacks prior to treatment or the number of attacks in a control subject.

In some embodiments, the therapeutic regimens of the invention ameliorate one or more symptoms associated with migraine in a patient in need thereof. For instance, administration of an anti-CGRP receptor antibody or binding fragment thereof to the patient according to the methods described herein reduces the occurrence of or treats one or more symptoms in the patients as compared to a control subject (i.e. a subject not receiving the anti-CGRP receptor or binding fragment). Symptoms that can be ameliorated or treated with the methods of the invention include, but are not limited to, vasomotor symptoms (e.g. hot flashes, facial flushing, sweating, and night sweats), photophobia (sensitivity to light), phonophobia (sensitivity to sound), sensitivity to smells, vertigo, dizziness, nausea, vomiting, and headache pain.

In some aspects, the methods of the invention comprise administering to a patient a pharmaceutical composition comprising a therapeutically effective amount of an anti-CGRP receptor antibody or antigen-binding fragment thereof. A "therapeutically effective amount" refers to an amount sufficient to remedy migraine headache or symptoms, particularly a state or symptoms associated with migraine headache, or otherwise prevent, hinder, retard or reverse the progression of migraine headache or any other undesirable symptom associated with migraine headache in any way whatsoever. In certain embodiments, a therapeutically effective amount is an amount sufficient to prevent or delay the onset or reoccurrence of migraine headache or reduce the likelihood of the onset or reoccurrence of migraine headache or its symptoms.

Thus, in some embodiments, an anti-CGRP receptor antibody or antigen-binding fragment thereof is administered to the patient at a total dose of about 35 mg to about 210 mg per month. For instance, the dose of an anti-CGRP receptor antibody or binding fragment thereof can be about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, or about 210 mg per month. Ranges between any and all of these endpoints are also contemplated, for example about 35 mg to about 70 mg, about 40 mg to about 90 mg, about 50 mg to about 80 mg, about 35 mg to about 140 mg, about 70 mg to about 140 mg, about 50 mg to about 100 mg, about 70 mg to about 210 mg, about 140 mg to about 210 mg, or about 150 mg to about 200 mg per month. In some such embodiments, the monthly dose of the anti-CGRP receptor antibody or binding fragment thereof is similar among patients regardless of body weight. In other words, in these embodiments, the monthly dosage of anti-CGRP receptor antibody or binding fragment thereof is a total dose and is not adjusted for a patient's body weight. In one embodiment, an anti-CGRP receptor antibody or binding fragment thereof is administered to the patient at a total dose of about 70 mg to about 140 mg per month. In certain embodiments of the methods described herein, an anti-CGRP receptor antibody or binding fragment thereof is administered to the patient at a total dose of about 70 mg per month. In other embodiments, an anti-CGRP receptor antibody or binding fragment thereof is administered to the patient at a total dose of about 140 mg per month.

In certain embodiments, the monthly dose of anti-CGRP receptor antibody or binding fragment thereof may be based upon a patient's body weight. For example, in some embodiments, the monthly dose of an anti-CGRP receptor antibody or binding fragment thereof may range from about 0.3 mg/kg to about 3.5 mg/kg of body weight, from about 0.5 mg/kg to about 3 mg/kg of body weight, or from about 1 mg/kg to about 2.5 mg/kg of body weight. For instance, the monthly dose of anti-CGRP receptor antibody or binding fragment thereof may be about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.2 mg/kg, about 3.3 mg/kg, about 3.4 mg/kg, or about 3.5 mg/kg of body weight. In one embodiment, the monthly dose of anti-CGRP receptor antibody or binding fragment thereof is about 0.8 mg/kg to about 1.2 mg/kg of body weight. In another embodiment, the monthly dose of anti-CGRP receptor antibody or binding fragment thereof is about 1.6 mg/kg to about 2.2 mg/kg of weight.

The dose of anti-CGRP receptor antibody or antigen-binding fragment thereof can be administered in a single administration or divided among multiple administrations over the course of the dosing frequency period. For example, in certain embodiments, the therapeutically effective dose of anti-CGRP receptor antibody or binding fragment thereof is administered in a single administration each frequency period. Thus, in some embodiments, any of the doses of anti-CGRP receptor antibody or binding fragment thereof described herein can be administered to the patient once a month (QM dosing). Patients on a QM dosing regimen are typically administered the anti-CGRP receptor antibody or binding fragment thereof every 24 to 36 days, preferably, every 28 to 35 days, more preferably, every 28 to 31 days, or even more preferably, every 28 days or every 30 days. In these and other embodiments, the monthly dose is administered to the patient as a bolus injection, for example, using a self-injection device as described herein. For instance, a monthly dose of 70 mg can be administered to the patient as a single bolus injection of 70 mg optionally with an auto-injector, pen injector, or pre-filled syringe containing the 70 mg dose. In certain embodiments, the monthly dose is given in two or more consecutive injections. By way of example, a monthly dose of 70 mg can be administered to the patient in two consecutive injections of 35 mg optionally with two injection devices (e.g. autoinjectors, pen injectors, or pre-filled syringes) containing a 35 mg dose. Similarly, a monthly dose of 140 mg can be administered to the patient in two consecutive injections of 70 mg optionally with two injection devices (e.g. autoinjectors, pen injectors, or pre-filled syringes) containing a 70 mg dose. Consecutive injections given within the period of a single day are considered to be a single administration. In other words, by way of example, a single bolus injection of 70 mg and two consecutive injections of 35 mg within the period of one day would both be considered to be a single administration of a 70 mg dose.

In alternative embodiments, the doses of anti-CGRP receptor antibody or binding fragment thereof are divided among two or more administrations over the course of the dosing frequency period. For example, for a dosing frequency period of one month, the monthly dose may be divided into four doses and administered on a weekly basis or divided into two doses and administered every two weeks. Any of the doses of the anti-CGRP receptor antibody or binding fragment described herein can be divided among two or more administrations. The number of administrations and intervening interval can be adjusted for a particular patient depending on the type and severity of migraine (e.g. episodic or chronic), the age of the patient, the physical health of the patient, concomitant treatment with other medications, and/or the presence of other conditions.

In certain embodiments, the dosing frequency period for the doses of an anti-CGRP receptor antibody or binding fragment thereof that are described herein is monthly. In other words, the dosages of anti-CGRP receptor antibodies or binding fragments thereof are monthly dosages, but can be administered in a single administration (i.e. once a month; QM dosing) or divided among multiple administrations over the course of the month (e.g. ½ the monthly dose administered every two weeks). In some embodiments, the dosing frequency is once every 2 months (Q2M dosing). In other embodiments, the dosing frequency is once every 3 months (Q3M dosing).

In some embodiments of the methods of the invention, the anti-CGRP receptor antibody or binding fragment is administered to the patient over the course of a set treatment period. A "treatment period" begins upon administration of a first dose of anti-CGRP receptor antibody or binding fragment and ends upon administration of a final dose of anti-CGRP receptor antibody or binding fragment. The treatment period may comprise from about 1 month to about 36 months, such as about 2 months, about 3 months, about 4 months, about 5 months, about 6 months, about 7 months, about 8 months, about 9 months, about 10 months, about 11 months, about 12 months, about 13 months, about 14 months, about 15 months, about 18 months, about 21 months, about 24 months, about 27 months, about 30 months, or about 33 months. In some embodiments, the treatment period is about 6 months. In other embodiments, the treatment period is about 7 months. In yet other embodiments, the treatment period is about 12 months. In certain embodiments, the treatment period can be longer than 36 months, such as 48 or 60 or 64 months or more. In one particular embodiment, the treatment period is at least about 6 months and produces a statistically significant reduction in the frequency, duration, or severity of migraine headache in the patient as compared to untreated subjects.

Administration of an anti-CGRP receptor antibody or binding fragment thereof according to the methods of the invention preferably causes few or no adverse side effects in the patient. As used herein, the term "adverse side effect" refers to any abnormality, defect, mutation, lesion, degeneration, harmful or undesirable reaction, symptom, or injury, which may be caused by taking the drug. In some embodiments, administration of the anti-CGRP receptor antibody or binding fragment thereof does not substantially cause one or more adverse side effects associated with other migraine prophylactic treatments (e.g. amitriptyline, divalproex, valproic acid, propranolol, timolol, topiramate, and botulinum toxin A). Side effects associated with other migraine prophylactic treatments include, but are not limited to, fatigue, nausea, dizziness, insomnia, depression, reduced exercise tolerance, tremor, paresthesia, teratogenicity, and cognitive difficulty. In other embodiments, administration of the anti-CGRP receptor antibody or binding fragment thereof is associated with a lower rate or number of adverse side effects as compared to the rate or number of adverse side effects associated with other migraine prophylactic treatments. In yet other embodiments, administration of the anti-CGRP receptor antibody or binding fragment thereof is associated with a lower rate of discontinuation due to adverse side effects as compared to the rate of discontinuation due to adverse side effects associated with other migraine prophylactic treatments. In certain embodiments, the number and type of adverse side effects associated with administration of the anti-CGRP receptor antibody or binding fragment is not statistically different than the number and type of adverse side effects associated with administration of placebo. In some embodiments, administration of an anti-CGRP receptor antibody or binding fragment thereof is not associated with an adverse event higher than grade 2 as assessed by the Common Terminology Criteria for Adverse Events v4.0 (CTCAE). In other embodiments, administration of an anti-CGRP receptor antibody or binding fragment thereof is not associated with an adverse event higher than grade 1 as assessed by the CTCAE.

In certain embodiments, the patients to be treated according to the methods of the invention have, suffer from, or are diagnosed with episodic migraine. Episodic migraine is diagnosed when patients with a history of migraine (e.g. at least five lifetime attacks of migraine headache) have 14 or fewer migraine headache days as defined herein per month. In some embodiments, patients having, suffering from, or diagnosed with episodic migraine have at least four, but less than 15 migraine headache days per month on average. In related embodiments, patients having, suffering from, or diagnosed with episodic migraine have fewer than 15 headache days per month on average. As used herein, a "headache day" is any calendar day in which the patient experiences a migraine headache as defined herein or any headache that lasts greater than 30 minutes or requires acute headache treatment. In some embodiments, the patient may be classified as having or suffering from high-frequency episodic migraine. High-frequency episodic migraine can be characterized by 8 to 14 migraine headache days per month. In other embodiments, the patient may be classified as having or suffering from low-frequency episodic migraine. Low-frequency episodic migraine can be characterized by less than 8 migraine headache days per month.

In some embodiments, the patients to be treated according to the methods of the invention have, suffer from, or are diagnosed with chronic migraine. Chronic migraine is diagnosed when migraine patients (i.e. patients with at least five lifetime attacks of migraine headache) have 15 or more headache days per month and at least 8 of the headache days are migraine headache days. In some embodiments, patients having, suffering from, or diagnosed with chronic migraine have 15 or more migraine headache days per month on average. In certain embodiments of the methods described herein, administration of an anti-CGRP receptor antibody or binding fragment thereof prevents, reduces, or delays the progression of episodic migraine in the patient to chronic migraine.

In certain embodiments of the methods described herein, the patient is treatment-naïve. In one embodiment, a patient is treatment-naïve if the patient has not previously received treatment for migraine headaches. In another embodiment, the patient is treatment-naïve if the patient was not administered a therapeutic agent for the treatment of migraine headaches. In some embodiments, a patient is treatment-naïve if the patient has not previously received prophylactic therapy for migraine headaches. For instance, in certain embodiments, a treatment-naïve patient has not received prior therapy or has not been administered a therapeutic agent for the prophylactic treatment of episodic migraine. In certain other embodiments, a treatment-naïve patient has not received prior therapy or has not been administered a therapeutic agent for the prophylactic treatment of chronic migraine.

In some embodiments of the methods described herein, the patient has failed or is intolerant to at least one other migraine headache prophylactic therapy. For example, in one particular embodiment, the patient has failed to respond to prior therapy with at least one migraine headache prophylactic agent. As used herein, "failure to respond" or "treatment failure" refers to the lack of efficacy of the prophylactic agent in reducing the frequency, duration, and/or severity of migraine headache in the patient following a standard therapeutic regimen of the agent. For instance, in one embodiment, a patient who has failed prior treatment with a migraine prophylactic agent is a patient who experienced the same or a greater number of monthly migraine headache days following administration of the migraine prophylactic agent as compared to the number of monthly migraine headache days prior to treatment with the agent. In another embodiment, a patient who has failed prior treatment with a migraine prophylactic agent is a patient who experienced the same or a greater number of monthly acute migraine-specific medication treatment days following administration of the migraine prophylactic agent as compared to the number of monthly acute migraine-specific medication treatment days prior to treatment with the agent. In yet another embodiment, a patient who has failed prior treatment with a migraine prophylactic agent is a patient who experienced the same or a greater number of migraine attacks following administration of the migraine prophylactic agent as compared to the number of migraine attacks prior to treatment with the agent. In still another embodiment, a patient who has failed prior treatment with a migraine prophylactic agent is a patient who experienced the same level or a greater level of physical impairment (e.g. mean monthly days with physical impairment) as measured by the MPFID following administration of the migraine prophylactic agent as compared to the level of physical impairment prior to treatment with the agent.

Failure to respond to prior treatment with a migraine prophylactic agent can also include inability to tolerate the migraine prophylactic agent. For example, in some embodiments, a patient who has failed prior treatment with a migraine prophylactic agent is a patient who cannot tolerate the side effects associated with the agent. In such embodiments, the side effects associated with the agent may exacerbate or may be incompatible with another medical condition which the patient has. By way of illustration, migraine prophylactic agents having a side effect of teratogenicity would be contraindicated in a pregnant patient. In certain embodiments, a patient who has failed prior treatment with a migraine prophylactic agent is a patient who discontinues treatment with the migraine prophylactic agent due to associated side effects. In these and other embodiments, a patient who has failed prior treatment with a migraine prophylactic agent is a patient who elects to stop treatment, alter the treatment regimen, or switch to a different prophylactic agent because the impact of the side effects is greater than the therapeutic benefit of the migraine prophylactic agent.

Migraine prophylactic agents include, but are not limited to, beta-blockers (e.g., propranolol, timolol, atenolol, metoprolol, and nadolol), antiepileptics (e.g. divalproex, sodium valproate, valproic acid, topiramate, and gabapentin), tricyclic antidepressants (e.g., amitriptyline, nortriptyline, doxepin, and fluoxetine), and botulinum toxin type A. Thus, in certain embodiments, the patients treated according to the methods of the invention have failed or are intolerant to one or more of these migraine prophylactic agents. In some embodiments, the patient has failed or is intolerant to treatment with at least two migraine prophylactic agents. In other embodiments, the patient has failed or is intolerant to treatment with at least three migraine prophylactic agents. In certain embodiments, the patient has failed or is intolerant to treatment with one or more agents selected from propranolol, timolol, divalproex, valproic acid, topiramate, amitriptyline, or botulinum toxin type A. In one particular embodiment, the patient has failed or is intolerant to treatment with topiramate. In another particular embodiment, the patient has failed or is intolerant to treatment with propranolol. In yet another particular embodiment, the patient has failed or is intolerant to treatment with amitriptyline.

In some embodiments, the patient has failed or is intolerant to treatment with two different classes of migraine prophylactic agents. For instance, in one embodiment, the patient may have failed or is intolerant to treatment with an antiepileptic (e.g. topiramate) and a beta-blocker (e.g. propranolol). In another embodiment, the patient may have failed or is intolerant to treatment with an antiepileptic (e.g. topiramate) and an antidepressant (e.g. amitriptyline). In still another embodiment, the patient may have failed or is intolerant to treatment with a beta-blocker (e.g. propranolol) and an antidepressant (e.g. amitriptyline). In certain embodiments, the patient has failed or is intolerant to treatment with three different classes of migraine prophylactic agents. In such embodiments, the patient has failed or is intolerant to treatment with an antiepileptic (e.g. topiramate), a beta-blocker (e.g. propranolol), and an antidepressant (e.g. amitriptyline).

The methods described herein are also applicable to other types of headache disorders such as tension-type headaches, cluster headaches, hemiplegic migraine, and retinal migraine. Accordingly, the present invention also provides methods for treating, including prophylactically treating, or preventing any of the aforementioned headache disorders by administering an anti-CGRP receptor antibody or binding fragment thereof to a patient in need thereof with any of the dosage regimens described herein.

The methods described herein comprise administering to a patient an anti-CGRP receptor antibody or binding fragment thereof. The term "antibody," as used herein, refers to an intact immunoglobulin of any isotype, or an antigen binding fragment thereof that can compete with the intact antibody for specific binding to the target antigen, and includes, for instance, chimeric, humanized, fully human, bispecific, and multivalent antibodies. The structural units of antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region." Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contains three C region domains known as CH1, CH2 and CH3. The antibodies that can be employed in the methods of the invention can have any of these isotypes and subtypes. In certain embodiments, the anti-CGRP receptor antibody is of the IgG1, IgG2, or IgG4 subtype. In one particular embodiment, the anti-CGRP receptor antibody is an IgG2 antibody (e.g. comprises a human IgG2 constant domain). In another particular embodiment, the anti-CGRP receptor antibody is an IgG1 antibody (e.g. comprises a human IgG1 constant domain).

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site. Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain and light chain pair typically are aligned by the framework regions to form a structure that binds specifically to a specific epitope on the target protein (e.g., CGRP receptor). From N-terminal to C-terminal, naturally-occurring light and heavy chain variable regions both typically conform with the following order of these elements: FR1, CDR1, FR2, CDR2, FR3, CDR3, and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342: 878-883.

The term "binding fragment" is used interchangeably herein with the term "antigen-binding fragment" and refers to a portion (regardless of how that portion is obtained or synthesized) of an antibody that lacks at least some of the amino acids present in a full-length heavy chain and/or light chain, but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelid or rabbit.

An antibody binding fragment may be a synthetic or genetically engineered protein. For example, antibody binding fragments include isolated fragments consisting of the light chain variable region, "Fv" fragments consisting of the variable regions of the heavy and light chains, and recombinant single chain polypeptide molecules in which light and heavy variable regions are connected by a peptide linker (scFv proteins). Another form of an antibody binding fragment is a peptide comprising one or more complementarity determining regions (CDRs) of an antibody. CDRs (also termed "minimal recognition units" or "hypervariable region") are obtained by, e.g., constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology, 2:106 (1991); Courtenay-Luck, "Genetic Manipulation of Monoclonal Antibodies," in Monoclonal Antibodies Production, Engineering and Clinical Application, Ritter et al. (eds.), page 166, Cambridge University Press (1995); and Ward et al., "Genetic Manipulation and Expression of Antibodies," in Monoclonal Antibodies: Principles and Applications, Birch et al., (eds.), page 137, Wiley-Liss, Inc. (1995)).

The anti-CGRP receptor antibody or binding fragment thereof used in the methods of the invention specifically binds to the human CGRP receptor. The human CGRP receptor is a heterodimer that comprises the human calcitonin receptor-like receptor (CRLR) polypeptide and the human receptor activity modifying protein 1 (RAMP1) polypeptide. In some embodiments, the anti-CGRP receptor antibody or binding fragment thereof specifically binds to regions of the extracellular domains of CRLR and RAMP1. The amino acid sequences for exemplary extracellular domains and the full-length proteins for human CRLR and RAMP1 are provided in the table below.

binds the target antigen with "high affinity" when the $K_D$ is $\leq 1\times 10^{-8}$ M. In one embodiment, the antibodies or binding fragments bind to human CGRP receptor with a $K_D \leq 5\times 10^{-7}$ M. In another embodiment, the antibodies or binding fragments bind to human CGRP receptor with a $K_D \leq 1\times 10^{-7}$ M. In still another embodiment, the antibodies or binding fragments bind to human CGRP receptor with a $K_D \leq 5\times 10^{-8}$ M. In another embodiment, the antibodies or binding fragments bind to human CGRP receptor with a $K_D \leq 1\times 10^{-8}$ M. In another embodiment the antibodies or binding fragments bind to human CGRP receptor with a $K_D \leq 5\times 10^{-9}$ M. In certain embodiments the antibodies or binding fragments bind to human CGRP receptor with a $K_D \leq 1\times 10^{-9}$ M. In other embodiments, the antibodies or binding fragments bind to human CGRP receptor with a $K_D \leq 5\times 10^{-10}$ M. In still other embodiments, the antibodies or binding fragments bind to human CGRP receptor with a $K_D \leq 1\times 10^{-10}$ M. Affinity is determined using a variety of techniques, an example of which is an affinity ELISA assay. In various embodiments, affinity is determined by a BIAcore assay. In some embodiments, affinity is determined by a kinetic method. In other embodiments, affinity is determined by an equilibrium/solution method. In certain embodiments, affinity is determined by a FACS binding assay. WO 2010/075238, which is hereby incorporated by reference in its entirety, describes suitable affinity assays for determining the affinity for anti-CGRP receptor antibodies.

In certain embodiments, the anti-CGRP receptor antibody or binding fragment thereof employed in the methods described herein specifically binds to residues or sequences of residues, or regions in both human CRLR and human RAMP1 polypeptides. In one particular embodiment, the anti-CGRP receptor antibody or binding fragment thereof specifically binds to an epitope formed from amino acids in both human CRLR and human RAMP1 polypeptides. An "epitope" refers to any determinant capable of specifically binding to an antibody or binding fragment thereof or to a

TABLE 1

Sequences of human CRLR and human RAMP1 polypeptides

| Polypeptide | Sequence |
| --- | --- |
| Human CRLR | MLYSIFHFGLMMEKKCTLYFLVLLPFFMILVTAELEESPEDSIQLGVTR NKIMTAQYECYQKIMQDPIQQAEGVYCNRTWDGWLCWNDVAAGTE SMQLCPDYFQDFDPSEKVTKICDQDGNWFRHPASNRTWTNYTQCNV NTHEKVKTALNLFYLTIIGHGLSIASLLISLGIFFYFKSLSCQRITLHKNL FFSFVCNSVVTIIHLTAVANNQALVATNPVSCKVSQFIHLYLMGCNYF WMLCEGIYLHTLIVVAVFAEKQHLMWYYFLGWGFPLIPACIHAIARS LYYNDNCWISSDTHLLYIIHGPICAALLVNLFFLLNIVRVLITKLKVTH QAESNLYMKAVRATLILVPLLGIEFVLIPWRPEGKIAEEVYDYIMHIL MHFQGLLVSTIFCFFNGEVQAILRRNWNQYKIQFGNSFSNSEALRSAS YTVSTISDGPGYSHDCPSEHLNGKSIHDIENVLLKPENLYN (SEQ ID NO: 1) |
| Human RAMP1 | MARALCRLPRRGLWLLLAHHLFMTTACQEANYGALLRELCLTQFQV DMEAVGETLWCDWGRTIRSYRELADCTWHMAEKLGCFWPNAEVDR FFLAVHGRYFRSCPISGRAVRDPPGSILYPFIVVPITVTLLVTALVVWQ SKRTEGIV (SEQ ID NO: 2) |
| Extracellular Domain of Human CRLR | ELEESPEDSIQLGVTRNKIMTAQYECYQKIMQDPIQQAEGVYCNRTW DGWLCWNDVAAGTESMQLCPDYFQDFDPSEKVTKICDQDGNWFRH PASNRTWTNYTQCNVNTHEKVKTA (SEQ ID NO: 3) |
| Extracellular Domain of Human RAMP1 | CQEANYGALLRELCLTQFQVDMEAVGETLWCDWGRTIRSYRELADC TWHMAEKLGCFWPNAEVDRFFLAVHGRYFRSCPISGRAVRDPPGS (SEQ ID NO: 4) |

An antibody or binding fragment is said to "specifically bind" to its target when the dissociation constant ($K_D$) is $\leq 10^{-6}$ M. The antibody or binding fragment specifically T-cell receptor. An epitope can be contiguous or non-contiguous (e.g., (i) in a single-chain polypeptide, amino acid residues that are not contiguous to one another in the polypeptide sequence but that within in context of the molecule are bound by the antigen binding protein, or (ii) in a multimeric protein, e.g., comprising two or more individual components, amino acid residues present on two or more of the individual components, but that within the context of the multimeric protein are bound by the antibody or binding fragment). In some embodiments, the epitope formed from amino acids in both human CRLR and human RAMP1 polypeptides comprises one or more cleavage sites for AspN protease, which cleaves peptides after aspartic acid residues and some glutamic acid residues at the amino end.

In certain embodiments, the anti-CGRP receptor antibody or binding fragment used in the methods of the invention specifically binds to an extracellular domain of human CRLR polypeptide comprising the amino acid sequence of SEQ ID NO: 3. Alternatively or additionally, the anti-CGRP receptor antibody or binding fragment specifically binds to an extracellular domain of human RAMP1 polypeptide comprising the amino acid sequence of SEQ ID NO: 4. In some embodiments, the anti-CGRP receptor antibody or binding fragment specifically binds to at least one sequence within the human CRLR polypeptide selected from SEQ ID NO: 5 (DSIQLGVTRNKIMTAQY; corresponding to amino acids 8-24 of SEQ ID NO: 3), SEQ ID NO: 6 (DVAAGTESMQLCP; corresponding to amino acids 55-67 of SEQ ID NO: 3), SEQ ID NO: 7 (DGNWFRHPASN-RTWTNYTQCNVNTH; corresponding to amino acids 86-110 of SEQ ID NO: 3), SEQ ID NO: 8 (ECYQKIMQ; corresponding to amino acids 25-32 of SEQ ID NO: 3), or SEQ ID NO: 9 (DGWLCWN; corresponding to amino acids 48-54 of SEQ ID NO: 3). For example, in some embodiments, the anti-CGRP receptor antibody binds a subregion of human CRLR polypeptide of SEQ ID NO: 3 comprising SEQ ID NOs: 5-9, optionally in its native three-dimensional conformation. Alternatively or additionally, the anti-CGRP receptor antibody or binding fragment specifically binds to at least one sequence within the human RAMP1 polypeptide selected from SEQ ID NO: 10 (RELADCTWHMAE; corresponding to amino acids 41-52 of SEQ ID NO: 4), SEQ ID NO: 11 (DWGRTIRSYRELA; corresponding to amino acids 32-44 of SEQ ID NO: 4), SEQ ID NO: 12 (EL-CLTQFQV; corresponding to amino acids 12-20 of SEQ ID NO: 4), or SEQ ID NO: 13 (DCTWHMA; corresponding to amino acids 45-51 of SEQ ID NO: 4). In some embodiments, the anti-CGRP receptor antibody binds a subregion of human RAMP1 polypeptide of SEQ ID NO: 4 comprising SEQ ID NOs: 10-13, optionally in its native three-dimensional conformation.

In certain embodiments, the anti-CGRP receptor antibody or binding fragment specifically binds to a human CRLR polypeptide having the amino acid sequences of SEQ ID NO: 6, SEQ ID NO: 7, SEQ ID NO: 8, and SEQ ID NO: 9, wherein SEQ ID NOs: 6 and 7 are joined by a disulfide bond at amino acid positions 66 and 105 with reference to SEQ ID NO: 3, and SEQ ID NOs: 8 and 9 are joined by a disulfide bond at amino acid positions 26 and 52 with reference to SEQ ID NO: 3, optionally wherein the polypeptide retains the tertiary structure of the corresponding polypeptide region of human CRLR of SEQ ID NO: 3. In some embodiments, the anti-CGRP receptor antibody or binding fragment specifically binds to a human RAMP1 polypeptide having the amino acid sequences of SEQ ID NO: 12 and SEQ ID NO: 13, where the sequences are joined by a disulfide bond at amino acid positions 14 and 46 with reference to SEQ ID NO: 4, optionally wherein the polypeptide retains the tertiary structure of the corresponding polypeptide region of human RAMP1 of SEQ ID NO: 4. In particular embodiments, the anti-CGRP receptor antibody or binding fragment specifically binds to a human CRLR polypeptide and a human RAMP1 polypeptide, wherein the human CRLR polypeptide has the amino acid sequences of SEQ ID NO: 6, SEQ ID NO: 7, SEQ ID NO: 8, and SEQ ID NO: 9, wherein SEQ ID NOs: 6 and 7 are joined by a disulfide bond at amino acid positions 66 and 105 with reference to SEQ ID NO: 3, and SEQ ID NOs: 8 and 9 are joined by a disulfide bond at amino acid positions 26 and 52 with reference to SEQ ID NO: 3, and wherein the human RAMP1 polypeptide has the amino acid sequences of SEQ ID NO: 12 and SEQ ID NO: 13, wherein SEQ ID NOs: 12 and 13 are joined by a disulfide bond at amino acid positions 14 and 46 with reference to SEQ ID NO: 4. In such embodiments, the human CRLR and human RAMP1 polypeptides retain the tertiary structure of the corresponding regions of human CRLR and human RAMP1 polypeptides of SEQ ID NOs: 3 and 4, respectively. In related embodiments, the human CRLR and human RAMP1 polypeptides form a heterodimer.

Anti-CGRP receptor antibodies or binding fragments suitable for use in the methods of the invention preferably inhibit, interfere with, or modulate one or more biological activities of the human CGRP receptor. Biological activities of the human CGRP receptor include, but are not limited to, induction of CGRP receptor signal transduction pathways, induction of vasodilation, inhibition of vasoconstriction, and induction of inflammation, e.g., neurogenic inflammation. In some embodiments, the anti-CGRP receptor or antigen-binding fragment thereof substantially inhibits binding of human CGRP receptor to the CGRP ligand. "Substantial inhibition of binding" occurs when an excess of antibody or binding fragment thereof reduces the quantity of human CGRP receptor bound to CGRP, or vice versa, by at least about 20%, about 30%, about 40%, about 50%, about 60%, about 70%, about 80%, about 85%, about 90%, about 95%, about 97%, about 99% or more, for example by measuring binding in an in vitro competitive binding assay.

In certain embodiments, anti-CGRP receptor antibodies or binding fragments for use in the methods described herein selectively inhibit the human CGRP receptor as compared with the human adrenomedullin 1 (AM1), adrenomedullin 2 (AM2), or amylin receptors (e.g. human AMY1 receptor). The human AM1 receptor is comprised of a human CRLR polypeptide and a RAMP2 polypeptide, whereas the human AM2 receptor is comprised of a human CRLR polypeptide and a RAMP3 polypeptide. Thus, an antibody or other binding protein that binds only CRLR (and not RAMP1) would not be expected to selectively inhibit the CGRP receptor because the CRLR polypeptide is also a component of the AM1 and AM2 receptors. The human amylin (AMY) receptors are comprised of a human calcitonin receptor (CT) polypeptide and one of the RAMP1, RAMP2, or RAMP3 subunits. Specifically, the human AMY1 receptor is composed of the CT polypeptide and the RAMP1 polypeptide, the human AMY2 receptor is composed of the CT polypeptide and the RAMP2 polypeptide, and the human AMY3 receptor is composed of the CT polypeptide and the RAMP3 polypeptide. Thus, an antibody or other binding protein that binds only RAMP1 (and not CRLR) would not be expected to selectively inhibit the CGRP receptor because the RAMP1 polypeptide is also a component of the human AMY1 receptor.

An antibody or antigen-binding fragment thereof "selectively inhibits" a specific receptor relative to other receptors when the IC50 of the antibody or antigen-binding fragment thereof in an inhibition assay of the specific receptor is at least 50-fold lower than the IC50 in an inhibition assay of another "reference" receptor. An "IC50" is the amount of a drug or substance that is needed to inhibit a given biological process by half. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any anti-CGRP antibody or binding fragment can be calculated by determining the concentration of the antibody or binding fragment needed to inhibit half of the maximum biological response of the CGRP ligand in activating the CGRP receptor in any functional assay.

The "selectivity ratio" is the IC50 of the reference receptor divided by IC50 of the specific receptor. An anti-CGRP receptor antibody or antigen-binding fragment thereof selectively inhibits the human CGRP receptor if the IC50 of the antibody or antigen-binding fragment thereof in a functional CGRP receptor assay, such as the cyclic AMP (cAMP) assay, is at least 50-fold lower than the IC50 of that same antibody or antigen-binding fragment thereof in an inhibition assay of the human AM1, AM2 or an amylin receptor (e.g., AMY1). By way of non-limiting example, if the IC50 of a specific anti-CGRP receptor antibody in a cAMP assay of the human CGRP receptor is, e.g., between 0.1 nM and 20 nM, and the IC50 of the same antibody in a cAMP assay of the human AM1, human AM2 or human AMY1 receptor is 1000 nM or more, that antibody would be considered to selectively inhibit the human CGRP receptor. The degree of selective inhibition may be determined using any suitable CGRP receptor functional assay, such as the cAMP assay as described in Example 4 of WO 2010/075238, which is hereby incorporated by reference in its entirety. An antibody or antigen-binding fragment thereof that selectively inhibits a specific receptor is also understood to be a neutralizing antibody or antigen-binding fragment with respect to that receptor. In certain embodiments, the anti-CGRP receptor antibody or binding fragment thereof may selectively inhibit the human CGRP receptor, relative to the human AM1, AM2, and/or AMY1 receptors, e.g., with a selectivity ratio of 100 or more, 250 or more, 500 or more, 750 or more, 1,000 or more, 2,500 or more, 5,000 or more or 10,000 or more. In one embodiment, the anti-CGRP receptor antibody or binding fragment thereof selectively inhibits the human CGRP receptor relative to the human AM1, AM2, and/or AMY1 receptors with a selectivity ratio of 100 or more. In another embodiment, the anti-CGRP receptor antibody or binding fragment thereof selectively inhibits the human CGRP receptor relative to the human AM1, AM2, and/or AMY1 receptors with a selectivity ratio of 500 or more.

In some embodiments, the anti-CGRP receptor antibody or binding fragment thereof specifically binds to both human CRLR and human RAMP1 polypeptides, and does not specifically bind to human AM1, human AM2, and/or a human amylin receptor (e.g., AMY1 or AMY2). For example, the anti-CGRP receptor antibody or binding fragment thereof may specifically bind the human CGRP receptor with a $K_D \leq 1$ μM, $\leq 100$ nM, $\leq 10$ nM, or $\leq 5$ nM. In some embodiments, the anti-CGRP receptor antibody or binding fragment thereof specifically binds to the human CGRP receptor with a $K_D \leq 100$ nM, $\leq 10$ nM, or $\leq 5$ nM as determined using a FACS binding assay and analyzed, for example, using methods described in Rathanaswami, et al., *Biochemical and Biophysical Research Communications* 334 (2005) 1004-1013. In certain embodiments, the anti-CGRP receptor antibody or binding fragment thereof specifically binds to the human CGRP receptor with a $K_D \leq 100$ nM. In other embodiments, the anti-CGRP receptor antibody or binding fragment thereof specifically binds to the human CGRP receptor with a $K_D \leq 10$ nM.

In certain embodiments, the anti-CGRP receptor antibody or binding fragment thereof has a Ki of $\leq 100$ nM, $\leq 10$ nM, $\leq 1$ nM, $\leq 0.5$ nM or $\leq 0.1$ nM in a CGRP binding competition assay. "Ki" refers to the equilibrium dissociation constant of a ligand determined in inhibition studies. The Ki for a given ligand is typically determined in a competitive radiolabeled ligand binding study by measuring the inhibition of the binding of a reference radiolabeled ligand by the competing substance of interest under equilibrium conditions. Binding competition assays for assessing inhibitors of a ligand/receptor interaction are known to those of skill in the art and can include assays using radiolabeled ligands (e.g. radiolabeled CGRP) and cells expressing the receptor (e.g. human CGRP receptor). In some embodiments, the Ki of the anti-CGRP receptor antibody or binding fragment thereof is determined using a radiolabeled $^{125}$I-CGRP binding competition assay in which binding of the radiolabeled ligand to membranes from cells expressing human CGRP receptor is assessed. An exemplary protocol for conducting this type of assay is described in Example 5 of WO 2010/075238, which is hereby incorporated by reference in its entirety. In one embodiment, the anti-CGRP receptor antibody or binding fragment thereof has a Ki of less than 10 nM in a CGRP binding competition assay. In another embodiment, the anti-CGRP receptor antibody or binding fragment thereof has a Ki of less than 1 nM in a CGRP binding competition assay.

Examples of anti-CGRP receptor antibodies or binding fragments thereof suitable for use in the methods of the invention are described in WO 2010/075238, which is hereby incorporated by reference in its entirety. In one embodiment, the anti-CGRP receptor antibody or binding fragment thereof employed in the methods described herein cross-blocks the binding of at least one of antibodies 1E11, 1H7, 2E7, 3B6, 3C8, 4E4, 4H6, 5F5, 9D4, 9F5, 10E4, 11D11, 11H9, 12E8, 12G8, 13H2 and 32H7 (all of which are described herein and in WO 2010/075238) to the human CGRP receptor. Alternatively or in addition, the anti-CGRP receptor antibody or binding fragment thereof is cross-blocked from binding to the human CGRP receptor by at least one of antibodies 1E11, 1H7, 2E7, 3B6, 3C8, 4E4, 4H6, 5F5, 9D4, 9F5, 10E4, 11D11, 11H9, 12E8, 12G8, 13H2 and 32H7 (all of which are described further herein). All of these antibodies were determined to be neutralizing antibodies of the human CGRP receptor and to bind to essentially the same region of the human CGRP receptor, a region which was distinct from the region of the receptor that was bound by non-neutralizing antibodies. See Example 7 of WO 2010/075238. The terms "cross-block," "cross-blocked," and "cross-blocking" are used interchangeably herein to mean the ability of an antibody to interfere with the binding of other antibodies or binding fragments to the human CGRP receptor. The extent to which an antibody or binding fragment is able to interfere with the binding of another to the human CGRP receptor, and therefore whether it can be said to cross-block, can be determined using competition binding assays. In some embodiments, a cross-blocking antibody or binding fragment thereof reduces human CGRP receptor binding of a reference antibody between about 40% and 100%, such as about 60% and about 100%, specifically between about 70% and 100%, and more specifically between about 80% and 100%. A particularly suitable quantitative assay for detecting cross-blocking uses a Biacore machine which measures the extent of interactions using surface plasmon resonance technology. Another suitable quantitative cross-blocking assay uses a FACS-based approach to measure competition between antibodies in terms of their binding to the human CGRP receptor.

The anti-CGRP receptor antibodies and binding fragments thereof for use in the methods disclosed herein may comprise one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). In some embodiments, the anti-CGRP receptor antibody or binding fragment comprises at least one heavy chain variable region comprising a CDRH1, CDRH2, and CDRH3 and at least one light chain variable region comprising a CDRL1, CDRL2, and CDRL3. Specific heavy and light chain CDRs are listed in Tables 2 and 3, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies and binding fragments that are disclosed herein comprise one or more amino acid sequences that are identical or have substantial sequence identity to the amino acid sequences of one or more of the CDRs presented in Table 2 (heavy chain CDRs, i.e. CDRHs) and Table 3 (light chain CDRs, i.e. CDRLs).

TABLE 2

Exemplary Heavy Chain CDR Amino Acid Sequences

| SEQ ID NO: | Designation | Sequence |
|---|---|---|
| 14 | CDRH 1-1 | SFGMH |
| 15 | CDRH 1-2 | NAWMS |
| 16 | CDRH 1-3 | SYAMS |
| 17 | CDRH 1-4 | GYYMH |
| 18 | CDRH 1-5 | SYGMH |
| 19 | CDRH 1-6 | DYAMS |
| 20 | CDRH 1-7 | DYYMY |
| 21 | CDRH 1-8 | TYSMN |
| 22 | CDRH 1-9 | SYGMH |
| 23 | CDRH 2-1 | VISFDGSIKYSVDSVKG |
| 24 | CDRH 2-2 | RIKSTTDGGTTDYAAPVKG |
| 25 | CDRH 2-3 | AISGSGGRTYYADSVKG |
| 26 | CDRH 2-4 | WINPNSGGTNYAQKFQG |
| 27 | CDRH 2-5 | VISYDGSHESYADSVKG |
| 28 | CDRH 2-6 | FIRSRAYGGTPEYAASVKG |
| 29 | CDRH 2-7 | RIKSKTDGGTTDYTAPVKG |
| 30 | CDRH 2-8 | WISPNSGGTNYAQKFQG |
| 31 | CDRH 2-9 | RIKSKTDGGTTDYAAPVKG |
| 32 | CDRH 2-10 | SISSSSSYRYYADSVKG |

TABLE 2-continued

Exemplary Heavy Chain CDR Amino Acid Sequences

| SEQ ID NO: | Designation | Sequence |
|---|---|---|
| 33 | CDRH 2-11 | VIWYDGSNKYYADSVKG |
| 34 | CDRH 3-1 | DRLNYYDSSGYYHYKYYGMAV |
| 35 | CDRH 3-2 | DRTGYSISWSSYYYYYGMDV |
| 36 | CDRH 3-3 | DQREVGPYSSGWYDYYYGMDV |
| 37 | CDRH 3-4 | DQMSIIMLRGVFPPYYYGMDV |
| 38 | CDRH 3-5 | ERKRVTMSTLYYYFYYGMDV |
| 39 | CDRH 3-6 | GRGIAARWDY |
| 40 | CDRH 3-7 | GGYSGYAGLYSHYYGMDV |
| 41 | CDRH 3-8 | DRLNYYDSSGYYHYKYYGLAV |
| 42 | CDRH 3-9 | EGVSGSSPYSISWYDYYYGMDV |
| 43 | CDRH 3-10 | AGGIAAAGLYYYYGMDV |

TABLE 3

Exemplary Light Chain CDR Amino Acid Sequences

| SEQ ID NO: | Designation | Sequence |
|---|---|---|
| 44 | CDRL 1-1 | SGSSSNIGNNYVS |
| 45 | CDRL 1-2 | SGSSSNIGSNYVY |
| 46 | CDRL 1-3 | RASQGIRNDLG |
| 47 | CDRL 1-4 | QGDSLRSFYAS |
| 48 | CDRL 1-5 | KSSQSLLHSAGKTYLY |
| 49 | CDRL 1-6 | RSSQSLLHSFGYNYLD |
| 50 | CDRL 1-7 | KSSQSLLHSDGKTYLY |
| 51 | CDRL 1-8 | SGSSSNIGSNTVN |
| 52 | CDRL 1-9 | KSSQSLLHSDGRNYLY |
| 53 | CDRL 1-10 | RASQGIRKDLG |
| 54 | CDRL 1-11 | RASQSVSSGYLT |
| 55 | CDRL 2-1 | DNNKRPS |
| 56 | CDRL 2-2 | RSNQRPS |
| 57 | CDRL 2-3 | AASSLQS |
| 58 | CDRL 2-4 | GKNNRPS |
| 59 | CDRL 2-5 | EVSNRFS |
| 60 | CDRL 2-6 | LGSNRAS |
| 61 | CDRL 2-7 | RNNQRPS |
| 62 | CDRL 2-8 | TNNQRPS |
| 63 | CDRL 2-9 | GASSLQS |
| 64 | CDRL 2-10 | GASSRAT |
| 65 | CDRL 3-1 | GTWDSRLSAVV |
| 66 | CDRL 3-2 | AAWDDSLSGWV |

TABLE 3-continued

Exemplary Light Chain CDR Amino Acid Sequences

| SEQ ID NO: | Designation | Sequence |
|---|---|---|
| 67 | CDRL 3-3 | LQYNIYPWT |
| 68 | CDRL 3-4 | NSRDSSVYHLV |
| 69 | CDRL 3-5 | MQSFPLPLT |
| 70 | CDRL 3-6 | MQALQTPFT |
| 71 | CDRL 3-7 | AARDESLNGVV |
| 72 | CDRL 3-8 | LQYNSFPWT |
| 73 | CDRL 3-9 | QQYGNSLCR |
| 74 | CDRL 3-10 | QQYGNSLSR |

In some embodiments, the anti-CGRP receptor antibodies or binding fragments thereof comprise one or more heavy chain CDRs selected from (i) a CDRH1 selected from the group consisting of SEQ ID NOs: 14 to 22; (ii) a CDRH2 selected from the group consisting of SEQ ID NOs: 23 to 33; (iii) a CDRH3 selected from the group consisting of SEQ ID NOs: 34 to 43; and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids. In these and other embodiments, the anti-CGRP receptor antibodies or binding fragments thereof comprise one or more light chain CDRs selected from (i) a CDRL1 selected from the group consisting of SEQ ID NOs: 44 to 54; (ii) a CDRL2 selected from the group consisting of SEQ ID NOs: 55 to 64; (iii) a CDRL3 selected from the group consisting of SEQ ID NOs: 65 to 74; and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In certain embodiments, the anti-CGRP receptor antibodies or binding fragments thereof may comprise 1, 2, 3, 4, 5, or 6 variant forms of the CDRs listed in Tables 2 and 3, each having at least 80%, 85%, 90% or 95% sequence identity to a CDR sequence listed in Tables 2 and 3. Some anti-CGRP receptor antibodies or binding fragments thereof include 1, 2, 3, 4, 5, or 6 of the CDRs listed in Tables 2 and 3, each differing by no more than 1, 2, 3, 4 or 5 amino acids from the CDRs listed in these tables.

In some embodiments, the anti-CGRP receptor antibodies or binding fragments comprise a heavy chain variable region comprising CDRH1, CDRH2, and a CDRH3, wherein:
(a) CDRH1, CDRH2, and CDRH3 have the sequence of SEQ ID NOs: 14, 23 and 34, respectively;
(b) CDRH1, CDRH2, and CDRH3 have the sequence of SEQ ID NOs: 15, 24 and 35, respectively;
(c) CDRH1, CDRH2, and CDRH3 have the sequence of SEQ ID NOs: 16, 25 and 36, respectively;
(d) CDRH1, CDRH2, and CDRH3 have the sequence of SEQ ID NOs: 17, 26 and 37, respectively;
(e) CDRH1, CDRH2, and CDRH3 have the sequence of SEQ ID NOs: 18, 27 and 38, respectively;
(f) CDRH1, CDRH2, and CDRH3 have the sequence of SEQ ID NOs: 15, 29 and 35, respectively;
(g) CDRH1, CDRH2, and CDRH3 have the sequence of SEQ ID NOs: 20, 30 and 40, respectively;
(h) CDRH1, CDRH2, and CDRH3 have the sequence of SEQ ID NOs: 15, 31 and 35, respectively;
(i) CDRH1, CDRH2, and CDRH3 have the sequence of SEQ ID NOs: 14, 23 and 41, respectively;
(j) CDRH1, CDRH2, and CDRH3 have the sequence of SEQ ID NOs: 21, 32 and 42, respectively;
(k) CDRH1, CDRH2, and CDRH3 have the sequence of SEQ ID NOs: 22, 33 and 43, respectively; or
(l) CDRH1, CDRH2, and CDRH3 have the sequence of SEQ ID NOs: 19, 28 and 39, respectively.

In some embodiments, the anti-CGRP receptor antibodies or binding fragments comprise a light chain variable region comprising CDRL1, CDRL2, and a CDRL3, wherein:
(a) CDRL1, CDRL2, and CDRL3 have the sequence of SEQ ID NOs: 44, 55 and 65, respectively;
(b) CDRL1, CDRL2, and CDRL3 have the sequence of SEQ ID NOs: 45, 56 and 66, respectively;
(c) CDRL1, CDRL2, and CDRL3 have the sequence of SEQ ID NOs: 46, 57 and 67, respectively;
(d) CDRL1, CDRL2, and CDRL3 have the sequence of SEQ ID NOs: 47, 58 and 68, respectively;
(e) CDRL1, CDRL2, and CDRL3 have the sequence of SEQ ID NOs: 48, 59 and 69, respectively;
(f) CDRL1, CDRL2, and CDRL3 have the sequence of SEQ ID NOs: 49, 60 and 70, respectively;
(g) CDRL1, CDRL2, and CDRL3 have the sequence of SEQ ID NOs: 50, 59 and 69, respectively;
(h) CDRL1, CDRL2, and CDRL3 have the sequence of SEQ ID NOs: 45, 61 and 66, respectively;
(i) CDRL1, CDRL2, and CDRL3 have the sequence of SEQ ID NOs: 51, 62 and 71, respectively;
(j) CDRL1, CDRL2, and CDRL3 have the sequence of SEQ ID NOs: 52, 59 and 69, respectively;
(k) CDRL1, CDRL2, and CDRL3 have the sequence of SEQ ID NOs: 53, 63 and 72, respectively;
(l) CDRL1, CDRL2, and CDRL3 have the sequence of SEQ ID NOs: 54, 64 and 73, respectively; or
(m) CDRL1, CDRL2, and CDRL3 have the sequence of SEQ ID NOs: 54, 64 and 74, respectively.

In certain embodiments, the anti-CGRP receptor antibodies or binding fragments comprise a heavy chain variable region comprising CDRH1, CDRH2, and a CDRH3 and a light chain variable region comprising CDRL1, CDRL2, and a CDRL3, wherein:
(a) CDRH1, CDRH2, and CDRH3 have the sequence of SEQ ID NOs: 14, 23 and 34, respectively, and CDRL1, CDRL2, and CDRL3 have the sequence of SEQ ID NOs: 44, 55 and 65, respectively;
(b) CDRH1, CDRH2, and CDRH3 have the sequence of SEQ ID NOs: 14, 23 and 41, respectively, and CDRL1, CDRL2, and CDRL3 have the sequence of SEQ ID NOs: 44, 55 and 65, respectively;
(c) CDRH1, CDRH2, and CDRH3 have the sequence of SEQ ID NOs: 15, 24 and 35, respectively, and CDRL1, CDRL2, and CDRL3 have the sequence of SEQ ID NOs: 45, 56 and 66, respectively;
(d) CDRH1, CDRH2, and CDRH3 have the sequence of SEQ ID NOs: 15, 29 and 35, respectively, and CDRL1, CDRL2, and CDRL3 have the sequence of SEQ ID NOs: 45, 61 and 66, respectively;
(e) CDRH1, CDRH2, and CDRH3 have the sequence of SEQ ID NOs: 15, 31 and 35, respectively, and CDRL1, CDRL2, and CDRL3 have the sequence of SEQ ID NOs: 45, 61 and 66, respectively;

(f) CDRH1, CDRH2, and CDRH3 have the sequence of SEQ ID NOs: 16, 25 and 36, respectively, and CDRL1, CDRL2, and CDRL3 have the sequence of SEQ ID NOs: 46, 57 and 67, respectively;

(g) CDRH1, CDRH2, and CDRH3 have the sequence of SEQ ID NOs: 17, 26 and 37, respectively, and CDRL1, CDRL2, and CDRL3 have the sequence of SEQ ID NOs: 47, 58 and 68, respectively;

(h) CDRH1, CDRH2, and CDRH3 have the sequence of SEQ ID NOs: 18, 27 and 38, respectively, and CDRL1, CDRL2, and CDRL3 have the sequence of SEQ ID NOs: 48, 59 and 69, respectively;

(i) CDRH1, CDRH2, and CDRH3 have the sequence of SEQ ID NOs: 18, 27 and 38, respectively, and CDRL1, CDRL2, and CDRL3 have the sequence of SEQ ID NOs: 50, 59 and 69, respectively;

(j) CDRH1, CDRH2, and CDRH3 have the sequence of SEQ ID NOs: 19, 28 and 39, respectively, and CDRL1, CDRL2, and CDRL3 have the sequence of SEQ ID NOs: 49, 60 and 70, respectively;

(k) CDRH1, CDRH2, and CDRH3 have the sequence of SEQ ID NOs: 20, 30 and 40, respectively, and CDRL1, CDRL2, and CDRL3 have the sequence of SEQ ID NOs: 51, 62 and 71, respectively;

(l) CDRH1, CDRH2, and CDRH3 have the sequence of SEQ ID NOs: 21, 32 and 42, respectively, and CDRL1, CDRL2, and CDRL3 have the sequence of SEQ ID NOs: 53, 63 and 72, respectively;

(m) CDRH1, CDRH2, and CDRH3 have the sequence of SEQ ID NOs: 22, 33 and 43, respectively, and CDRL1, CDRL2, and CDRL3 have the sequence of SEQ ID NOs: 54, 64 and 73, respectively; or (n) CDRH1, CDRH2, and CDRH3 have the sequence of SEQ ID NOs: 22, 33 and 43, respectively, and CDRL1, CDRL2, and CDRL3 have the sequence of SEQ ID NOs: 54, 64 and 74, respectively; or (o) CDRH1, CDRH2, and CDRH3 have the sequence of SEQ ID NOs: 18, 27 and 38, respectively, and CDRL1, CDRL2, and CDRL3 have the sequence of SEQ ID NOs: 52, 59 and 69, respectively.

In some embodiments, the anti-CGRP receptor antibody or binding fragment thereof used in the methods of the invention comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65. In other embodiments, the anti-CGRP receptor antibody or binding fragment thereof used in the methods of the invention comprises a CDRH1 having the sequence of SEQ ID NO:15, a CDRH2 having the sequence of SEQ ID NO:29, a CDRH3 having the sequence of SEQ ID NO:35, a CDRL1 having the sequence of SEQ ID NO:45, a CDRL2 having the sequence of SEQ ID NO:61, and a CDRL3 having the sequence of SEQ ID NO:66.

In certain embodiments of the methods described herein, the anti-CGRP receptor antibody or binding fragment thereof comprises a heavy chain variable region selected from the group consisting of $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$, and/or a light chain variable region selected from the group consisting of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, and $V_L17$, as shown in Table 4 below, and immunologically functional fragments, derivatives, muteins and variants of these light chain and heavy chain variable regions.

TABLE 4

Exemplary $V_L$ and $V_H$ Chain Amino Acid Sequences

| Designation | SEQ ID NO. | Amino Acid Sequence |
|---|---|---|
| Light chain variable regions ||| 
| $V_L1$ | 75 | QSVLTQPPSVSEAPGQKVTISCSGSSSNIGNNYVSWYQ QLPGTAPKLLIYDNNKRPSGIPDRFSGSKSGTSATLGIT GLQTGDEADYYCGTWDSRLSAVVFGGGTKLTVL |
| $V_L2$ | 76 | QSVLTQPPSASGTPGQRVTISCSGSSSNIGSNYVYWYQ QLPGAAPKLLIFRSNQRPSGVPDRFSGSKSGTSASLAIS GLRSEDEADYYCAAWDDSLSGWVFGGGTKLTVL |
| $V_L3$ | 77 | DIQMTQSPSSLSASVGDRVTITCRASQGIRNDLGWFQQ KPGKAPKRLIYAASSLQSGVPSRFSGSGSGTEFTLTISSL QPEDLATYYCLQYNIYPWTFGQGTKVEJK |
| $V_L4$ | 78 | SSELTQDPTVSVALGQTVKITCQGDSLRSFYASWYQQ KPGQAPVLVFYGKNNRPSGIPDRFSGSSSGNTASLTITG AQAEDEADYYCNSRDSSVYHLVLGGGTKLTVL |
| $V_L5$ | 79 | DIILAQTPLSLSVTPGQPASISCKSSQSLLHSAGKTYLY WYLQKPGQPPQLLIYEVSNRFSGVPDRFSGSGSGTDFT LKISRVEAEDVGIYYCMQSFPLPLTFGGGTKVEIK |
| $V_L6$ | 80 | QSVLTQPPSVSAAPGQKVTISCSGSSSNIGNNYVSWYQ QLPGTAPKLLIYDNNKRPSGIPDRFSGSKSGTSTTLGIT GLQTGDEADYYCGTWDSRLSAVVFGGGTKLTVL |
| $V_L7$ | 81 | DIVMTQSPLSLPVTPGEPASISCRSSQSLLHSFGYNYLD WYLQKPGOSPOLLIYLGSNRASGVPDRFSGSGSGTDFT LKISRVEAEDVGVYYCMQALQTPFTFGPGTKVDIK |

TABLE 4-continued

Exemplary V_L and V_H Chain Amino Acid Sequences

| Designation | SEQ ID NO. | Amino Acid Sequence |
|---|---|---|
| V_L8 | 82 | DIILTQTPLSLSVTPGQPASISCKSSQSLLHSDGKTYLYWYLQKPGQPPQLLIYEVSNRFSGEPDRFSGSGSGTDFTLKISRVEAEDVGTYYCMQSFPLPLTFGGGTKVEIK |
| V_L9 | 83 | QSVLTQPPSVSAAPGQKVTISCSGSSSNIGNNYVSWYQQFPGTAPKLLIYDNNKRPSGIPDRFSGSKSGTSATLGITGLQTGDEADYYCGTWDSRLSAVVFGGGTKLTVL |
| V_L10 | 84 | QSVLTQSPSASGTPGQRVTISCSGSSSNIGSNYVYWYQQLPGAAPKLLILRNNQRPSGVPDRFSGSKSGTSASLTISGLRSEDEADYYCAAWDDSLSGWVFGGGTKLTVL |
| V_L11 | 85 | QSVLTQPPSASGTPGQRVTISCSGSSSNIGSNTVNWYQQLPGTAPKLLIYTNNQRPSGVPDRFSGSKSGTSASLAISGLQSEDEADFYCAARDESLNGVVFGGGTKLTVL |
| V_L12 | 86 | QSVLTQPPSASGTPGQRVTISCSGSSSNIGSNYVYWYQQLPGAAPKLLIFRNNQRPSGVPDRFSGSKSGTSASLAISGLRSEDEADYYCAAWDDSLSGWVFGGGTKLTVL |
| V_L13 | 87 | DITLTQTPLSLSVSPGQPASISCKSSQSLLHSDGRNYLYWYLQKPGQPPQLLIYEVSNRFSGLPDRFSGSGSGTDFTLKISRVEAEDVGIYYCMQSFPLPLTFGGGTKVEIK |
| V_L14 | 88 | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSRLSAVVFGGGTKLTVL |
| V_L15 | 89 | DIQMTQSPSSLSASVGDRVTITCRASQGIRKDLGWYQQKPGKAPKRLIYGASSLQSGVPSRFSGSGSGTEFTLTISSLQPEDFATYYCLQYNSFPWTFGQGTKVEIK |
| V_L16 | 90 | EIVLTQSPGTLSLSPGERATLSCRASQSVSSGYLTWYQQKPGQAPRLLIYGASSRATGIPDRFSGSGSGTDFTLTISRLEPEDFAVYYCQQYGNSLCRFGQGTKLEIK |
| V_L17 | 91 | EIVLTQSPGTLSLSPGERATLSCRASQSVSSGYLTWYQQKPGQAPRLLIYGASSRATGIPDRFSGSGSGTDFTLTISRLEPEDFAVYYCQQYGNSLSRFGQGTKLEIK |
| Heavy chain variable regions | | |
| V_H1 | 92 | QVQLVESGGGVVQPGRSLRLSCAASGFTFSSFGMHWVRQAPGKGLEWVAVISFDGSIKYSVDSVKGRFTISRDNSKNTLFLQMNSLRAEDTAVYYCARDRLNYYDSSGYYHYKYYGMAVWGQGTTVTSS |
| V_H2 | 93 | EVQLVESGGGLVKPGGSLRLSCAASGFTFSNAWMSWVRQAPGKGLEWVGRIKSTTDGGTTDYAAPVKGRFTISRDDSKNTLYLQMNSLKTEDTAVYYCTTDRTGYSISWSSYYYYYGMDVWGQGTTVTSS |
| V_H3 | 94 | EVQLLESGGGLVQPGESLRLSCAASGFTFSSYAMSWVRQAPGKGLEWVSAISGSGGRTYYADSVKGRFTISRDNSKNTLYLQMNSLRAEDTAVYYCAKDQREVGPYSSGWYDYYYGMDVWGQGTTVTSS |
| V_H4 | 95 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYFCARDQMSIIMLRGVFPPYYYGMDVWGQGTTVTSS |
| V_H5 | 96 | QVQLVESGGGVVQPGRSLRLSCAASGFTFSSYGMHWVRQAPGKGLEWVAVISYDGSHESYADSVKGRFTISRDISKNTLYLQMNSLRAEDTAVYFCARERKRVTMSTLYYYFYYGMDVWGQGTTVTSS |
| V_H6 | 97 | EVQLVESGGGLVKPGRSLRLSCTASGFTFGDYAMSWFRQAPGKGLEWIGFIRSRAYGGTPEYAASVKGRFTISRDDSKTIAYLQMNSLKTEDTAVYFCARGRGIAARWDYWGQGTLVTVSS |

TABLE 4-continued

Exemplary $V_L$ and $V_H$ Chain Amino Acid Sequences

| Designation | SEQ ID NO. | Amino Acid Sequence |
|---|---|---|
| $V_H7$ | 98 | EVQLVESGGGLVKPGGSLRLSCAASGFTFSNAWMSW VRQAPGKGLEWVGRIKSKTDGGTTDYTAPVKGRFTIS RDDSKNTLYLQMNSLKAEDTAVYYCTTDRTGYSISWS SYYYYYGMDVWGQGTTVTVSS |
| $V_H8$ | 99 | QVQLVQSGAEVKKPGASVKVSCKASGYTFTDYYMY WVRQAPGQGLEWMGWISPNSGGTNYAQKFQGRVTM TRDTSISTAYMELSRLRSDDTAVYYCVRGGYSGYAGL YSHYYGMDVWGQGTTVTVSS |
| $V_H9$ | 100 | EVQLVESGGGLVKPGGSLRLSCAASGFTFGNAWMSW VRQAPGKGLEWVGRIKSKTDGGTTDYAAPVKGRFTIS RDDSKNTLYLQMNSLKTEDTAVYFCTTDRTGYSISWS SYYYYYGMDVWGQGTTVTVSS |
| $V_H10$ | 101 | EVQLVESGGGLVKPGGSLRLSCAASGFTFGNAWMSW VRQAPGKGLEWVGRIKSKTDGGTTDYAAPVKGRFTIS RDDSKNTLYLQMNSLKTEDTAVYYCTTDRTGYSISWS SYYYYYGMDVWGQGTTVTVSS |
| $V_H11$ | 102 | QVQLVESGGGVVQPGRSLRLSCAASGFTFSSFGMHWV RQAPGKGLEWVAVISFDGSIKYSVDSVKGRFTISRDNS KNTLFLQMNSLRAEDTAVYYCARDRLNYYDSSGYYH YKYYGLAVWGQGTTVTVSS |
| $V_H12$ | 103 | EVQLVESGGGLVKPGGSLRLSCAASGYTFSTYSMNWV RQAPGKGLEWVSSISSSSSYRYYADSVKGRFTISRDNA KNSLYLQMSSLRAEDTAVYYCAREGVSGSSPYSISWY DYYYGMDVWGQGTTVTVSS |
| $V_H13$ | 104 | QVQLVESGGGVVQPGRSLRLSCAASGFTFSSYGMHW VRQAPGKGLEWVAVIWYDGSNKYYADSVKGRFIISRD KSKNTLYLQMNSLRAEDTAVYYCARAGGIAAAGLYY YYGMDVWGQGTTVTVSS |

Each of the heavy chain variable regions listed in Table 4 may be combined with any of the light chain variable regions shown in Table 4 to form an anti-CGRP receptor antibody or binding fragment suitable for use in the methods of the invention. Examples of such combinations include $V_H1$ combined with any of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$; $V_H2$ combined with any of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$; $V_H3$ combined with any of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$; and so on.

In some embodiments, the anti-CGRP receptor antibody or binding fragment thereof includes at least one heavy chain variable region and/or one light chain variable region from those listed in Table 4. In certain embodiments, the anti-CGRP receptor antibody or binding fragment includes at least two different heavy chain variable regions and/or light chain variable regions from those listed in Table 4. An example of such an anti-CGRP receptor antibody or binding fragment comprises (a) one $V_H1$, and (b) one of $V_H2$, $V_H3$, $V_H4$, $V_H5$, $V_H6$, $V_H7$, $V_H8$, $V_H9$, $V_H10$, $V_H11$, $V_H12$, or $V_H13$. Another example comprises (a) one $V_H2$, and (b) one of $V_H1$, $V_H3$, $V_H4$, $V_H5$, $V_H6$, $V_H7$, $V_H8$, $V_H9$, $V_H10$, $V_H11$, $V_H12$, or $V_H13$. Again another example comprises (a) one $V_H3$, and (b) one of $V_H1$, $V_H2$, $V_H4$, $V_H5$, $V_H6$, $V_H7$, $V_H8$, $V_H9$, $V_H10$, $V_H11$, $V_H12$, or $V_H13$, etc. Again another example of such an anti-CGRP receptor antibody or binding fragment comprises (a) one $V_L1$, and (b) one of $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$, $V_L18$, $V_L19$, $V_L20$, or $V_L21$. Again another example of such an anti-CGRP receptor antibody or binding fragment comprises (a) one $V_L2$, and (b) one of $V_L1$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, or $V_L21$. Again another example of such an anti-CGRP receptor antibody or binding fragment comprises (a) one $V_L3$, and (b) one of $V_L1$, $V_L2$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, or $V_L21$, etc. The various combinations of heavy chain variable regions may be combined with any of the various combinations of light chain variable regions as is apparent to one of skill in the art.

In other embodiments, the anti-CGRP receptor antibody or binding fragment contains two identical light chain variable regions and/or two identical heavy chain variable regions. As an example, the anti-CGRP receptor antibody or binding fragment includes two light chain variable regions and two heavy chain variable regions in combinations of pairs of light chain variable regions and pairs of heavy chain variable regions as listed in Table 4.

In certain embodiments of the methods described herein, the anti-CGRP receptor antibodies or binding fragments thereof comprise a heavy chain variable domain comprising a sequence of amino acids that differs from the sequence of a heavy chain variable domain selected from $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some anti-CGRP receptor antibodies or binding fragments thereof comprises a sequence of amino acids that has at least 70%, 75%, 80%, 85%, 90%, 95%, 97% or 99% sequence identity to the amino acid sequences of the heavy chain variable region of $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$.

In some embodiments of the methods described herein, the anti-CGRP receptor antibodies or binding fragments thereof comprise a light chain variable domain comprising a sequence of amino acids that differs from the sequence of a light chain variable domain selected from $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some anti-CGRP receptor antibodies or binding fragments thereof comprises a sequence of amino acids that has at least 70%, 75%, 80%, 85%, 90%, 95%, 97% or 99% sequence identity to the amino acid sequences of the light chain variable region of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, or $V_L17$.

In certain embodiments, the anti-CGRP receptor antibody or antigen-binding fragment thereof suitable for use in the methods of the invention comprises a light chain variable region ($V_L$) and heavy chain variable region ($V_H$), wherein:

(a) $V_L$ comprises the sequence of SEQ ID NO: 75 and $V_H$ comprises the sequence of SEQ ID NO: 92;
(b) $V_L$ comprises the sequence of SEQ ID NO: 76 and $V_H$ comprises the sequence of SEQ ID NO: 93;
(c) $V_L$ comprises the sequence of SEQ ID NO: 77 and $V_H$ comprises the sequence of SEQ ID NO: 94;
(d) $V_L$ comprises the sequence of SEQ ID NO: 78 and $V_H$ comprises the sequence of SEQ ID NO: 95;
(e) $V_L$ comprises the sequence of SEQ ID NO: 79 and $V_H$ comprises the sequence of SEQ ID NO: 96;
(f) $V_L$ comprises the sequence of SEQ ID NO: 80 and $V_H$ comprises the sequence of SEQ ID NO: 92;
(g) $V_L$ comprises the sequence of SEQ ID NO: 81 and $V_H$ comprises the sequence of SEQ ID NO: 97;
(h) $V_L$ comprises the sequence of SEQ ID NO: 82 and $V_H$ comprises the sequence of SEQ ID NO: 96;
(i) $V_L$ comprises the sequence of SEQ ID NO: 83 and $V_H$ comprises the sequence of SEQ ID NO: 92;
(j) $V_L$ comprises the sequence of SEQ ID NO: 84 and $V_H$ comprises the sequence of SEQ ID NO: 98;
(k) $V_L$ comprises the sequence of SEQ ID NO: 85 and $V_H$ comprises the sequence of SEQ ID NO: 99;
(l) $V_L$ comprises the sequence of SEQ ID NO: 86 and $V_H$ comprises the sequence of SEQ ID NO: 100;
(m) $V_L$ comprises the sequence of SEQ ID NO: 86 and $V_H$ comprises the sequence of SEQ ID NO: 101;
(n) $V_L$ comprises the sequence of SEQ ID NO: 87 and $V_H$ comprises the sequence of SEQ ID NO: 96;
(o) $V_L$ comprises the sequence of SEQ ID NO: 88 and $V_H$ comprises the sequence of SEQ ID NO: 102;
(p) $V_L$ comprises the sequence of SEQ ID NO: 89 and $V_H$ comprises the sequence of SEQ ID NO: 103;
(q) $V_L$ comprises the sequence of SEQ ID NO: 90 and $V_H$ comprises the sequence of SEQ ID NO: 104; or
(r) $V_L$ comprises the sequence of SEQ ID NO: 91 and $V_H$ comprises the sequence of SEQ ID NO: 104.

In some embodiments, the anti-CGRP receptor antibodies or binding fragments may comprise amino acid sequences that have 70%, 75%, 80%, 85%, 90%, 95%, 97% or 99% sequence identity with the specified variable domains in the above pairings. In one particular embodiment, the anti-CGRP receptor antibody or binding fragment thereof used in the methods described herein comprises a heavy chain variable region comprising the sequence of SEQ ID NO: 92 and a light chain variable region comprising the sequence of SEQ ID NO: 80. In another particular embodiment, the anti-CGRP receptor antibody or binding fragment thereof used in the methods described herein comprises a heavy chain variable region comprising the sequence of SEQ ID NO: 98 and a light chain variable region comprising the sequence of SEQ ID NO: 84.

Specific examples of some of the full-length light and heavy chains of the anti-CGRP receptor antibodies useful in the methods of the invention and their corresponding amino acid sequences are summarized in Tables 5 and 6. Table 5 shows exemplary heavy chain sequences, and Table 6 shows exemplary light chain sequences.

TABLE 5

Exemplary Antibody Heavy Chain Amino Acid Sequences

| SEQ ID NO: | Designation | Sequence |
|---|---|---|
| 105 | H1 | QVQLVESGGGVVQPGRSLRLSCAASGFTFSSFGMHWVRQAPG KGLEWVAVISFDGSIKYSVDSVKGRFTISRDNSKNTLFLQMNS LRAEDTAVYYCARDRLNYYDSSGYYHYKYYGMAVWGQGTT VTVSSASTKGPSVFPLAPCSRSTSESTAALGCLVKDYFPEPVTV SWNSGALTSGVHTFPAVLQSSGLYSLSSVVTVPSSNFGTQTYT CNVDHKPSNTKVDKTVERKCCVECPPCPAPPVAGPSVFLFPPK PKDTLMISRTPEVTCVVVDVSHEDPEVQFNWYVDGVEVHNAK TKPREEQFNSTFRVVSVLTVVHQDWLNGKEYKCKVSNKGLPA PIEKTISKTKGQPREPQVYTLPPSREEMTKNQVSLTCLVKGFYP SDIAVEWESNGQPENNYKTTPPMLDSDGSFFLYSKLTVDKSR WQQGNVFSCSVMHEALHNHYTQKSLSLSPGK |
| 106 | H2 | EVQLVESGGGLVKPGGSLRLSCAASGFTFSNAWMSWVRQAPG KGLEWVGRIKSTTDGGTTDYAAPVKGRFTISRDDSKNTLYLQ MNSLKTEDTAVYYCTTDRTGYSISWSSYYYYGMDVWGQGT TVTVSSASTKGPSVFPLAPCSRSTSESTAALGCLVKDYFPEPVT VSWNSGALTSGVHTFPAVLQSSGLYSLSSVVTVPSSNFGTQTY TCNVDHKPSNTKVDKTVERKCCVECPPCPAPPVAGPSVFLFPP KPKDTLMISRTPEVTCVVVDVSHEDPEVQFNWYVDGVEVHNA KTKPREEQFNSTFRVVSVLTVVHQDWLNGKEYKCKVSNKGLP APIEKTISKTKGQPREPQVYTLPPSREEMTKNQVSLTCLVKGFY PSDIAVEWESNGQPENNYKTTPPMLDSDGSFFLYSKLTVDKSR WQQGNVFSCSVMHEALHNHYTQKSLSLSPGK |

TABLE 5-continued

Exemplary Antibody Heavy Chain Amino Acid Sequences

| SEQ ID NO: | Designation | Sequence |
|---|---|---|
| 107 | H3 | EVQLLESGGGLVQPGESLRLSCAASGFTFSSYAMSWVRQAPG KGLEWVSAISGSGGRTYYADSVKGRFTISRDNSKNTLYLQMN SLRAEDTAVYYCAKDQREVGPYSSGWYDYYYGMDVWGQGT TVTVSSASTKGPSVFPLAPCSRSTSESTAALGCLVKDYFPEPVT VSWNSGALTSGVHTFPAVLQSSGLYSLSSVVTVPSSNFGTQTY TCNVDHKPSNTKVDKTVERKCCVECPPCPAPPVAGPSVFLPP KPKDTLMISRTPEVTCVVVDVSHEDPEVQFNWYVDGVEVHNA KTKPREEQFNSTFRVVSVLTVVHQDWLNGKEYKCKVSNKGLP APIEKTISKTKGQPREPQVYTLPPSREEMTKNQVSLTCLVKGFY PSDIAVEWESNGQPENNYKTTPPMLDSDGSFFLYSKLTVDKSR WQQGNVFSCSVMHEALHNHYTQKSLSLSPGK |
| 108 | H4 | QVQLVQSGAEVKKPGASVKVSCKASGYTFTGYYMHWVRQAP GQGLEWMGWINPNSGGTNYAQKFQGRVTMTRDTSISTAYME LSRLRSDDTAVYFCARDQMSIIMLRGVFPPYYYGMDVWGQGT TVTVSSASTKGPSVFPLAPCSRSTSESTAALGCLVKDYFPEPVT VSWNSGALTSGVHTFPAVLQSSGLYSLSSVVTVPSSNFGTQTY TCNVDHKPSNTKVDKTVERKCCVECPPCPAPPVAGPSVFLPP KPKDTLMISRTPEVTCVVVDVSHEDPEVQFNWYVDGVEVHNA KTKPREEQFNSTFRVVSVLTVVHQDWLNGKEYKCKVSNKGLP APIEKTISKTKGQPREPQVYTLPPSREEMTKNQVSLTCLVKGFY PSDIAVEWESNGQPENNYKTTPPMLDSDGSFFLYSKLTVDKSR WQQGNVFSCSVMHEALHNHYTQKSLSLSPGK |
| 109 | H5 | QVQLVESGGGVVQPGRSLRLSCAASGFTFSSYGMHWVRQAPG KGLEWVAVISYDGSHESYADSVKGRFTISRDISKNTLYLQMNS LRAEDTAVYFCARERKRVTMSTLYYYFYYGMDVWGQGTTVT VSSASTKGPSVFPLAPCSRSTSESTAALGCLVKDYFPEPVTVSW NSGALTSGVHTFPAVLQSSGLYSLSSVVTVPSSNFGTQTYTCN VDHKPSNTKVDKTVERKCCVECPPCPAPPVAGPSVFLFPPKPK DTLMISRTPEVTCVVVDVSHEDPEVQFNWYVDGVEVHNAKT KPREEQFNSTFRVVSVLTVVHQDWLNGKEYKCKVSNKGLPAP IEKTISKTKGQPREPQVYTLPPSREEMTKNQVSLTCLVKGFYPS DIAVEWESNGQPENNYKTTPPMLDSDGSFFLYSKLTVDKSRW QQGNVFSCSVMHEALHNHYTQKSLSLSPGK |
| 110 | H6 | EVQLVESGGGLVKPGRSLRLSCTASGFTGDYAMSWFRQAPG KGLEWIGFIRSRAYGGTPEYAASVKGRFTISRDDSKTIAYLQM NSLKTEDTAVYFCARGRGIAARWDYWGQGTLVTVSSASTKGP SVFPLAPCSRSTSESTAALGCLVKDYFPEPVTVSWNSGALTSG VHTFPAVLQSSGLYSLSSVVTVPSSNFGTQTYTCNVDHKPSNT KVDKTVERKCCVECPPCPAPPVAGPSVFLFPPKPKDTLMISRTP EVTCVVVDVSHEDPEVQFNWYVDGVEVHNAKTKPREEQFNS TFRVVSVLTVVHQDWLNGKEYKCKVSNKGLPAPIEKTISKTK GQPREPQVYTLPPSREEMTKNQVSLTCLVKGFYPSDIAVEWES NGQPENNYKTTPPMLDSDGSFFLYSKLTVDKSRWQQGNVFSC SVMHEALHNHYTQKSLSLSPGK |
| 111 | H7 | EVQLVESGGGLVKPGGSLRLSCAASGFTFSNAWMSWVRQAPG KGLEWVGRIKSKTDGGTTDYTAPVKGRFTISRDDSKNTLYLQ MNSLKAEDTAVYYCTTDRTGYSISWSSYYYYGMDVWGQGT TVTVSSASTKGPSVFPLAPCSRSTSESTAALGCLVKDYFPEPVT VSWNSGALTSGVHTFPAVLQSSGLYSLSSVVTVPSSNFGTQTY TCNVDHKPSNTKVDKTVERKCCVECPPCPAPPVAGPSVFLPP KPKDTLMISRTPEVTCVVVDVSHEDPEVQFNWYVDGVEVHNA KTKPREEQFNSTFRVVSVLTVVHQDWLNGKEYKCKVSNKGLP APIEKTISKTKGQPREPQVYTLPPSREEMTKNQVSLTCLVKGFY PSDIAVEWESNGQPENNYKTTPPMLDSDGSFFLYSKLTVDKSR WQQGNVFSCSVMHEALHNHYTQKSLSLSPGK |
| 112 | H8 | QVQLVQSGAEVKKPGASVKVSCKASGYTFTDYYMYWVRQAP GQGLEWMGWISPNSGGTNYAQKFQGRVTMTRDTSISTAYME LSRLRSDDTAVYYCVRGGYSGYAGLYSHYYGMDVWGQGTT VTVSSASTKGPSVFPLAPCSRSTSESTAALGCLVKDYFPEPVTV SWNSGALTSGVHTFPAVLQSSGLYSLSSVVTVPSSNFGTQTYT CNVDHKPSNTKVDKTVERKCCVECPPCPAPPVAGPSVFLFPPK PKDTLMISRTPEVTCVVVDVSHEDPEVQFNWYVDGVEVHNAK TKPREEQFNSTFRVVSVLTVVHQDWLNGKEYKCKVSNKGLPA PIEKTISKTKGQPREPQVYTLPPSREEMTKNQVSLTCLVKGFYP SDIAVEWESNGQPENNYKTTPPMLDSDGSFFLYSKLTVDKSR WQQGNVFSCSVMHEALHNHYTQKSLSLSPGK |

TABLE 5-continued

Exemplary Antibody Heavy Chain Amino Acid Sequences

| SEQ ID NO: | Designation | Sequence |
|---|---|---|
| 113 | H9 | EVQLVESGGGLVKPGGSLRLSCAASGFTFGNAWMSWVRQAP GKGLEWVGRIKSKTDGGTTDYAAPVKGRFTISRDDSKNTLYL QMNSLKTEDTAVYFCTTDRTGYSISWSSYYYYGMDVWGQG TTVTVSSASTKGPSVFPLAPCSRSTSESTAALGCLVKDYFPEPV TVSWNSGALTSGVHTFPAVLQSSGLYSLSSVVTVPSSNFGTQT YTCNVDHKPSNTKVDKTVERKCCVECPPCPAPPVAGPSVFLFP PKPKDTLMISRTPEVTCVVVDVSHEDPEVQFNWYVDGVEVHN AKTKPREEQFNSTFRVVSVLTVVHQDWLNGKEYKCKVSNKG LPAPIEKTISKTKGQPREPQVYTLPPSREEMTKNQVSLTCLVKG FYPSDIAVEWESNGQPENNYKTTPPMLDSDGSFFLYSKLTVDK SRWQQGNVFSCSVMHEALHNHYTQKSLSLSPGK |
| 114 | H10 | EVQLVESGGGLVKPGGSLRLSCAASGFTFGNAWMSWVRQAP GKGLEWVGRIKSKTDGGTTDYAAPVKGRFTISRDDSKNTLYL QMNSLKTEDTAVYYCTTDRTGYSISWSSYYYYGMDVWGQG TTVTVSSASTKGPSVFPLAPCSRSTSESTAALGCLVKDYFPEPV TVSWNSGALTSGVHTFPAVLQSSGLYSLSSVVTVPSSNFGTQT YTCNVDHKPSNTKVDKTVERKCCVECPPCPAPPVAGPSVFLFP PKPKDTLMISRTPEVTCVVVDVSHEDPEVQFNWYVDGVEVHN AKTKPREEQFNSTFRVVSVLTVVHQDWLNGKEYKCKVSNKG LPAPIEKTISKTKGQPREPQVYTLPPSREEMTKNQVSLTCLVKG FYPSDIAVEWESNGQPENNYKTTPPMLDSDGSFFLYSKLTVDK SRWQQGNVFSCSVMHEALHNHYTQKSLSLSPGK |
| 115 | H11 | QVQLVESGGGVVQPGRSLRLSCAASGFTFSSFGMHWVRQAPG KGLEWVAVISFDGSIKYSVDSVKGRFTISRDNSKNTLFLQMNS LRAEDTAVYYCARDRLNYYDSSGYYHYKYYGLAVWGQTT VTVSSASTKGPSVFPLAPCSRSTSESTAALGCLVKDYFPEPVTV SWNSGALTSGVHTFPAVLQSSGLYSLSSVVTVPSSNFGTQTYT CNVDHKPSNTKVDKTVERKCCVECPPCPAPPVAGPSVFLFPPK PKDTLMISRTPEVTCVVVDVSHEDPEVQFNWYVDGVEVHNAK TKPREEQFNSTFRVVSVLTVVHQDWLNGKEYKCKVSNKGLPA PIEKTISKTKGQPREPQVYTLPPSREEMTKNQVSLTCLVKGFYP SDIAVEWESNGQPENNYKTTPPMLDSDGSFFLYSKLTVDKSR WQQGNVFSCSVMHEALHNHYTQKSLSLSPGK |
| 116 | H12 | EVQLVESGGGLVKPGGSLRLSCAASGYTFSTYSMNWVRQAPG KGLEWVSSISSSSSYRYYADSVKGRFTISRDNAKNSLYLQMSS LRAEDTAVYYCAREGVSGSSPYSISWYDYYYGMDVWGQGTT VTVSSASTKGPSVFPLAPCSRSTSESTAALGCLVKDYFPEPVTV SWNSGALTSGVHTFPAVLQSSGLYSLSSVVTVPSSNFGTQTYT CNVDHKPSNTKVDKTVERKCCVECPPCPAPPVAGPSVFLFPPK PKDTLMISRTPEVTCVVVDVSHEDPEVQFNWYVDGVEVHNAK TKPREEQFNSTFRVVSVLTVVHQDWLNGKEYKCKVSNKGLPA PIEKTISKTKGQPREPQVYTLPPSREEMTKNQVSLTCLVKGFYP SDIAVEWESNGQPENNYKTTPPMLDSDGSFFLYSKLTVDKSR WQQGNVFSCSVMHEALHNHYTQKSLSLSPGK |
| 117 | H13 | QVQLVESGGGVVQPGRSLRLSCAASGFTFSSYGMHWVRQAPG KGLEWVAVIWYDGSNKYYADSVKGRFIISRDKSKNTLYLQMN SLRAEDTAVYYCARAGGIAAAGLYYYYGMDVWGQGTTVTVS SASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLEPPKPKDT LMISRTPEVTCVVVDVSHEDPEVQFNWYVDGVEVHNAKTKPR EEQFNSTFRVVSVLTVVHQDWLNGKEYKCKVSNKGLPAPIEK TISKTKGQPREPQVYTLPPSREEMTKNQVSLTCLVKGFYPSDIA VEWESNGQPENNYKTTPPMLDSDGSFFLYSKLTVDKSRWQQG NVFSCSVMHEALHNHYTQKSLSLSPGK |

TABLE 6

Exemplary Antibody Light Chain Amino Acid Sequences

| SEQ ID NO: | Designation | Sequence |
|---|---|---|
| 118 | L1 | QSVLTQPPSVSEAPGQKVTISCSGSSSNIGNNYVSWYQQLPG TAPKLLIYDNNKRPSGIPDRFSGSKSGTSATLGITGLQTGDEA DYYCGTWDSRLSAVVFGGGTKLTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTECS |

TABLE 6-continued

Exemplary Antibody Light Chain Amino Acid Sequences

| SEQ ID NO: | Designation | Sequence |
|---|---|---|
| 119 | L2 | QSVLTQPPSASGTPGQRVTISCSGSSSNIGSNYVYWYQQLPG AAPKLLIFRSNQRPSGVPDRFSGSKSGTSASLAISGLRSEDEA DYYCAAWDDSLSGWVFGGGTKLTVLGQPKANPTVTLFPPS SEELQANKATLVCLISDFYPGAVTVAWKADGSPVKAGVETT KPSKQSNNKYAASSYLSLTPEQWKSHRSYSCQVTHEGSTVE KTVAPTECS |
| 120 | L3 | DIQMTQSPSSLSASVGDRVTITCRASQGIRNDLGWFQQKPGK APKRLIYAASSLQSGVPSRFSGSGSGTEFTLTISSLQPEDLAT YYCLQYNIYPWTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 121 | L4 | SSELTQDPTVSVALGQTVKITCQGDSLRSFYASWYQQKPGQ APVLVFYGKNNRPSGIPDRFSGSSSGNTASLTITGAQAEDEA DYYCNSRDSSVYHLVLGGGTKLTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTECS |
| 122 | L5 | DIILAQTPLSLSVTPGQPASISCKSSQSLLHSAGKTYLYWYLQ KPGQPPQLLIYEVSNRFSGVPDRFSGSGSGTDFTLKISRVEAE DVGIYYCMQSFPLPLTFGGGTKVEIKRTVAAPSVFIFPPSDEQ LKSGTASVVCLLNNFYPREAKVQWKVDNALQSGNSQESVT EQDSKDSTYSLSSTLTLSKADYEKHKVYACEVTHQGLSSPV TKSFNRGEC |
| 123 | L6 | QSVLTQPPSVSAAPGQKVTISCSGSSSNIGNNYVSWYQQLPG TAPKLLIYDNNKRPSGIPDRFSGSKSGTSTTLGITGLQTGDEA DYYCGTWDSRLSAVVFGGGTKLTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTECS |
| 124 | L7 | DIVMTQSPLSLPVTPGEPASISCRSSQSLLHSFGYNYLDWYL QKPGQSPQLLIYLGSNRASGVPDRFSGSGSGTDFTLKISRVE AEDVGVYYCMQALQTPFTFGPGTKVDIKRTVAAPSVFIFPPS DEQLKSGTASVVCLLNNFYPREAKVQWKVDNALQSGNSQE SVTEQDSKDSTYSLSSTLTLSKADYEKHKVYACEVTHQGLS SPVTKSFNRGEC |
| 125 | L8 | DIILTQTPLSLSVTPGQPASISCKSSQSLLHSDGKTYLYWYLQ KPGQPPQLLIYEVSNRFSGEPDRFSGSGSGTDFTLKISRVEAE DVGTYYCMQSFPLPLTFGGGTKVEIKRTVAAPSVFIFPPSDE QLKSGTASVVCLLNNFYPREAKVQWKVDNALQSGNSQESV TEQDSKDSTYSLSSTLTLSKADYEKHKVYACEVTHQGLSSP VTKSFNRGEC |
| 126 | L9 | QSVLTQPPSVSAAPGQKVTISCSGSSSNIGNNYVSWYQQFPG TAPKLLIYDNNKRPSGIPDRFSGSKSGTSATLGITGLQTGDEA DYYCGTWDSRLSAVVFGGGTKLTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTECS |
| 127 | L10 | QSVLTQSPSASGTPGQRVTISCSGSSSNIGSNYVYWYQQLPG AAPKLLILRNNQRPSGVPDRFSGSKSGTSASLTISGLRSEDEA DYYCAAWDDSLSGWVFGGGTKLTVLGQPKANPTVTLFPPS SEELQANKATLVCLISDFYPGAVTVAWKADGSPVKAGVETT KPSKQSNNKYAASSYLSLTPEQWKSHRSYSCQVTHEGSTVE KTVAPTECS |
| 128 | L11 | QSVLTQPPSASGTPGQRVTISCSGSSSNIGSNTVNWYQQLPG TAPKLLIYTNNQRPSGVPDRFSGSKSGTSASLAISGLQSEDEA DFYCAARDESLNGVVFGGGTKLTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTECS |

TABLE 6-continued

Exemplary Antibody Light Chain Amino Acid Sequences

| SEQ ID NO: | Designation | Sequence |
|---|---|---|
| 129 | L12 | QSVLTQPPSASGTPGQRVTISCSGSSSNIGSNYVYWYQQLPG<br>AAPKLLIFRNNQRPSGVPDRFSGSKSGTSASLAISGLRSEDEA<br>DYYCAAWDDSLSGWVFGGGTKLTVLGQPKANPTVTLFPPS<br>SEELQANKATLVCLISDFYPGAVTVAWKADGSPVKAGVETT<br>KPSKQSNNKYAASSYLSLTPEQWKSHRSYSCQVTHEGSTVE<br>KTVAPTECS |
| 130 | L13 | DITLTQTPLSLSVSPGQPASISCKSSQSLLHSDGRNYLYWYLQ<br>KPGQPPQLLIYEVSNRFSGLPDRFSGSGSGTDFTLKISRVEAE<br>DVGIYYCMQSFPLPLTFGGGTKVEIKRTVAAPSVFIFPPSDEQ<br>LKSGTASVVCLLNNFYPREAKVQWKVDNALQSGNSQESVT<br>EQDSKDSTYSLSSTLTLSKADYEKHKVYACEVTHQGLSSPV<br>TKSFNRGEC |
| 131 | L14 | QSVLTQPPSVSAAPGQKVTISCSGSSSNIGNNYVSWYQQLPG<br>TAPKLLIYDNNKRPSGIPDRFSGSKSGTSATLGITGLQTGDEA<br>DYYCGTWDSRLSAVVFGGGTKLTVLGQPKANPTVTLFPPSS<br>EELQANKATLVCLISDFYPGAVTVAWKADGSPVKAGVETT<br>KPSKQSNNKYAASSYLSLTPEQWKSHRSYSCQVTHEGSTVE<br>KTVAPTECS |
| 132 | L15 | DIQMTQSPSSLSASVGDRVTITCRASQGIRKDLGWYQQKPG<br>KAPKRLIYGASSLQSGVPSRFSGSGSGTEFTLTISSLQPEDFAT<br>YYCLQYNSFPWTFGQGTKVEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |
| 133 | L16 | EIVLTQSPGTLSLSPGERATLSCRASQSVSSGYLTWYQQKPG<br>QAPRLLIYGASSRATGIPDRFSGSGSGTDFTLTISRLEPEDFAV<br>YYCQQYGNSLCRFGQGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |
| 134 | L17 | EIVLTQSPGTLSLSPGERATLSCRASQSVSSGYLTWYQQKPG<br>QAPRLLIYGASSRATGIPDRFSGSGSGTDFTLTISRLEPEDFAV<br>YYCQQYGNSLSRFGQGTKLEIKRTVAAPSVFIFPPSDEQLKS<br>GTASVVCLLNNFYPREAKVQWKVDNALQSGNSQESVTEQD<br>SKDSTYSLSSTLTLSKADYEKHKVYACEVTHQGLSSPVTKSF<br>NRGEC |

Signal peptide sequences, for example to facilitate expression of the heavy and light chain sequences in certain types of host cells, may be appended/fused to the amino terminus of any of the heavy and light chain sequences listed in Tables 5 and 6. For instance, in some embodiments, a signal peptide having the amino acid sequence of MDMRVPAQLL-GLLLLWLRGARC (SEQ ID NO: 135) is fused to the amino terminus of any of the heavy and light chain sequences in Tables 5 and 6. In other embodiments, a signal peptide having the amino acid sequence of METPAQLL-FLLLLWLPDTTG (SEQ ID NO: 136) is fused to the amino terminus of any of the heavy and light chain sequences in Tables 5 and 6. Other signal peptides are known to those of skill in the art and may be fused to any of the heavy chains and/or light chains listed in Tables 5 and 6, for example, to facilitate or optimize expression in particular host cells.

Each of the exemplary heavy chains (H1, H2, H3 etc.) listed in Table 5 can be combined with any of the exemplary light chains shown in Table 6 to form an anti-CGRP receptor antibody suitable for use in the methods described herein. Examples of such combinations include H1 combined with any of L1 through L17; H2 combined with any of L1 through L17; H3 combined with any of L1 through L17, and so on. In some embodiments, the anti-CGRP receptor antibodies include at least one heavy chain and one light chain from those listed in Tables 5 and 6. In some embodiments, the anti-CGRP receptor antibodies comprise two different heavy chains and two different light chains listed in Tables 5 and 6. In other embodiments, the anti-CGRP receptor antibodies contain two identical light chains and two identical heavy chains. As an example, an anti-CGRP receptor antibody or binding fragment thereof may include two H1 heavy chains and two L1 light chains, or two H2 heavy chains and two L2 light chains, or two H3 heavy chains and two L3 light chains and other similar combinations of pairs of light chains and pairs of heavy chains as listed in Tables 5 and 6.

The anti-CGRP receptor antibodies employed in the methods of the invention may be variants of antibodies formed by combination of the heavy and light chains shown in Tables 5 and 6 and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances the variant forms contain two identical light chains and two identical heavy chains.

In some embodiments of the methods described herein, the anti-CGRP receptor antibody comprises:

(a) a heavy chain comprising the sequence of SEQ ID NO: 105 and a light chain comprising the sequence of SEQ ID NO: 118;

(b) a heavy chain comprising the sequence of SEQ ID NO: 106 and a light chain comprising the sequence of SEQ ID NO: 119;
(c) a heavy chain comprising the sequence of SEQ ID NO: 107 and a light chain comprising the sequence of SEQ ID NO: 120;
(d) a heavy chain comprising the sequence of SEQ ID NO: 108 and a light chain comprising the sequence of SEQ ID NO: 121;
(e) a heavy chain comprising the sequence of SEQ ID NO: 109 and a light chain comprising the sequence of SEQ ID NO: 122;
(f) a heavy chain comprising the sequence of SEQ ID NO: 105 and a light chain comprising the sequence of SEQ ID NO: 123;
(g) a heavy chain comprising the sequence of SEQ ID NO: 110 and a light chain comprising the sequence of SEQ ID NO: 124;
(h) a heavy chain comprising the sequence of SEQ ID NO: 109 and a light chain comprising the sequence of SEQ ID NO: 125;
(i) a heavy chain comprising the sequence of SEQ ID NO: 105 and a light chain comprising the sequence of SEQ ID NO: 126;
(j) a heavy chain comprising the sequence of SEQ ID NO: 111 and a light chain comprising the sequence of SEQ ID NO: 127;
(k) a heavy chain comprising the sequence of SEQ ID NO: 112 and a light chain comprising the sequence of SEQ ID NO: 128;
(l) a heavy chain comprising the sequence of SEQ ID NO: 113 and a light chain comprising the sequence of SEQ ID NO: 129;
(m) a heavy chain comprising the sequence of SEQ ID NO: 114 and a light chain comprising the sequence of SEQ ID NO: 129;
(n) a heavy chain comprising the sequence of SEQ ID NO: 109 and a light chain comprising the sequence of SEQ ID NO: 130;
(o) a heavy chain comprising the sequence of SEQ ID NO: 115 and a light chain comprising the sequence of SEQ ID NO: 131;
(p) a heavy chain comprising the sequence of SEQ ID NO: 116 and a light chain comprising the sequence of SEQ ID NO: 132;
(q) a heavy chain comprising the sequence of SEQ ID NO: 117 and a light chain comprising the sequence of SEQ ID NO: 133; or
(r) a heavy chain comprising the sequence of SEQ ID NO: 117 and a light chain comprising the sequence of SEQ ID NO: 134.

In one particular embodiment, the anti-CGRP receptor antibody used in the methods of the invention comprises a heavy chain comprising the sequence of SEQ ID NO: 105 and a light chain comprising the sequence of SEQ ID NO: 123. In another particular embodiment, the anti-CGRP receptor antibody used in the methods of the invention comprises a heavy chain comprising the sequence of SEQ ID NO: 111 and a light chain comprising the sequence of SEQ ID NO: 127.

Exemplary anti-CGRP receptor antibodies for use in the methods of the invention include, but are not limited to, antibodies 1E11, 1H7, 2E7, 3B6, 3C8, 4E4, 4H6, 5F5, 9D4, 9F5, 10E4, 11D11, 11H9, 12E8, 12G8, 13H2 and 32H7. Table 7 summarizes the structural characteristics of each of these antibodies.

TABLE 7

Exemplary Anti-CGRP Receptor Antibodies

| Antibody | Full Heavy Chain | Heavy Chain Variable Region | Heavy Chain CDRs | Full Light Chain | Light Chain Variable Region | Light Chain CDRs |
|---|---|---|---|---|---|---|
| 1E11 | H1 (SEQ ID NO: 105) | $V_H1$ (SEQ ID NO: 92) | CDRH 1-1 (SEQ ID NO: 14) CDRH 2-1 (SEQ ID NO: 23) CDRH 3-1 (SEQ ID NO: 34) | L1 (SEQ ID NO: 118) | $V_L1$ (SEQ ID NO: 75) | CDRL 1-1 (SEQ ID NO: 44) CDRL 2-1 (SEQ ID NO: 55) CDRL 3-1 (SEQ ID NO: 65) |
| 1H7 | H2 (SEQ ID NO: 106) | $V_H2$ (SEQ ID NO: 93) | CDRH 1-2 (SEQ ID NO: 15) CDRH 2-2 (SEQ ID NO: 24) CDRH 3-2 (SEQ ID NO: 35) | L2 (SEQ ID NO: 119) | $V_L2$ (SEQ ID NO: 76) | CDRL 1-2 (SEQ ID NO: 45) CDRL 2-2 (SEQ ID NO: 56) CDRL 3-2 (SEQ ID NO: 66) |
| 2E7 | H3 (SEQ ID NO: 107) | $V_H3$ (SEQ ID NO: 94) | CDRH 1-3 (SEQ ID NO: 16) CDRH 2-3 (SEQ ID NO: 25) CDRH 3-3 (SEQ ID NO: 36) | L3 (SEQ ID NO: 120) | $V_L3$ (SEQ ID NO: 77) | CDRL 1-3 (SEQ ID NO: 46) CDRL 2-3 (SEQ ID NO: 57) CDRL 3-3 (SEQ ID NO: 67) |
| 3B6 | H4 (SEQ ID NO: 108) | $V_H4$ (SEQ ID NO: 95) | CDRH 1-4 (SEQ ID NO: 17) CDRH 2-4 (SEQ ID NO: 26) CDRH 3-4 (SEQ ID NO: 37) | L4 (SEQ ID NO: 121) | $V_L4$ (SEQ ID NO: 78) | CDRL 1-4 (SEQ ID NO: 47) CDRL 2-4 (SEQ ID NO: 58) CDRL 3-4 (SEQ ID NO: 68) |
| 3C8 | H5 (SEQ ID NO: 109) | $V_H5$ (SEQ ID NO: 96) | CDRH 1-5 (SEQ ID NO: 18) CDRH 2-5 (SEQ ID NO: 27) CDRH 3-5 (SEQ ID NO: 38) | L5 (SEQ ID NO: 122) | $V_L5$ (SEQ ID NO: 79) | CDRL 1-5 (SEQ ID NO: 48) CDRL 2-5 (SEQ ID NO: 59) CDRL 3-5 (SEQ ID NO: 69) |

TABLE 7-continued

Exemplary Anti-CGRP Receptor Antibodies

| Antibody | Full Heavy Chain | Heavy Chain Variable Region | Heavy Chain CDRs | Full Light Chain | Light Chain Variable Region | Light Chain CDRs |
|---|---|---|---|---|---|---|
| 4E4 | H1 (SEQ ID NO: 105) | $V_H1$ (SEQ ID NO: 92) | CDRH 1-1 (SEQ ID NO: 14) CDRH 2-1 (SEQ ID NO: 23) CDRH 3-1 (SEQ ID NO: 34) | L6 (SEQ ID NO: 123) | $V_L6$ (SEQ ID NO: 80) | CDRL 1-1 (SEQ ID NO: 44) CDRL 2-1 (SEQ ID NO: 55) CDRL 3-1 (SEQ ID NO: 65) |
| 4H6 | H6 (SEQ ID NO: 110) | $V_H6$ (SEQ ID NO: 97) | CDRH 1-6 (SEQ ID NO: 19) CDRH 2-6 (SEQ ID NO: 28) CDRH 3-6 (SEQ ID NO: 39) | L7 (SEQ ID NO: 124) | $V_L7$ (SEQ ID NO: 81) | CDRL 1-6 (SEQ ID NO: 49) CDRL 2-6 (SEQ ID NO: 60) CDRL 3-6 (SEQ ID NO: 70) |
| 5F5 | H5 (SEQ ID NO: 109) | $V_H5$ (SEQ ID NO: 96) | CDRH 1-5 (SEQ ID NO: 18) CDRH 2-5 (SEQ ID NO: 27) CDRH 3-5 (SEQ ID NO: 38) | L8 (SEQ ID NO: 125) | $V_L8$ (SEQ ID NO: 82) | CDRL 1-7 (SEQ ID NO: 50) CDRL 2-5 (SEQ ID NO: 59) CDRL 3-5 (SEQ ID NO: 69) |
| 9D4 | H1 (SEQ ID NO: 105) | $V_H1$ (SEQ ID NO: 92) | CDRH 1-1 (SEQ ID NO: 14) CDRH 2-1 (SEQ ID NO: 23) CDRH 3-1 (SEQ ID NO: 34) | L9 (SEQ ID NO: 126) | $V_L9$ (SEQ ID NO: 83) | CDRL 1-1 (SEQ ID NO: 44) CDRL 2-1 (SEQ ID NO: 55) CDRL 3-1 (SEQ ID NO: 65) |
| 9F5 | H7 (SEQ ID NO: 111) | $V_H7$ (SEQ ID NO: 98) | CDRH 1-2 (SEQ ID NO: 15) CDRH 2-7 (SEQ ID NO: 29) CDRH 3-2 (SEQ ID NO: 35) | L10 (SEQ ID NO: 127) | $V_L10$ (SEQ ID NO: 84) | CDRL 1-2 (SEQ ID NO: 45) CDRL 2-7 (SEQ ID NO: 61) CDRL 3-2 (SEQ ID NO: 66) |
| 10E4 | H8 (SEQ ID NO: 112) | $V_H8$ (SEQ ID NO: 99) | CDRH 1-7 (SEQ ID NO: 20) CDRH 2-8 (SEQ ID NO: 30) CDRH 3-7 (SEQ ID NO: 40) | L11 (SEQ ID NO: 128) | $V_L11$ (SEQ ID NO: 85) | CDRL 1-8 (SEQ ID NO: 51) CDRL 2-8 (SEQ ID NO: 62) CDRL 3-7 (SEQ ID NO: 71) |
| 11D11 | H9 (SEQ ID NO: 113) | $V_H9$ (SEQ ID NO: 100) | CDRH 1-2 (SEQ ID NO: 15) CDRH 2-9 (SEQ ID NO: 31) CDRH 3-2 (SEQ ID NO: 35) | L12 (SEQ ID NO: 129) | $V_L12$ (SEQ ID NO: 86) | CDRL 1-2 (SEQ ID NO: 45) CDRL 2-7 (SEQ ID NO: 61) CDRL 3-2 (SEQ ID NO: 66) |
| 11H9 | H10 (SEQ ID NO: 114) | $V_H10$ (SEQ ID NO: 101) | CDRH 1-2 (SEQ ID NO: 15) CDRH 2-9 (SEQ ID NO: 31) CDRH 3-2 (SEQ ID NO: 35) | L12 (SEQ ID NO: 129) | $V_L12$ (SEQ ID NO: 86) | CDRL 1-2 (SEQ ID NO: 45) CDRL 2-7 (SEQ ID NO: 61) CDRL 3-2 (SEQ ID NO: 66) |
| 12E8 | H5 (SEQ ID NO: 109) | $V_H5$ (SEQ ID NO: 96) | CDRH 1-5 (SEQ ID NO: 18) CDRH 2-5 (SEQ ID NO: 27) CDRH 3-5 (SEQ ID NO: 38) | L13 (SEQ ID NO: 130) | $V_L13$ (SEQ ID NO: 87) | CDRL 1-9 (SEQ ID NO: 52) CDRL 2-5 (SEQ ID NO: 59) CDRL 3-5 (SEQ ID NO: 69) |
| 12G8 | H11 (SEQ ID NO: 115) | $V_H11$ (SEQ ID NO: 102) | CDRH 1-1 (SEQ ID NO: 14) CDRH 2-1 (SEQ ID NO: 23) CDRH 3-8 (SEQ ID NO: 41) | L14 (SEQ ID NO: 131) | $V_L14$ (SEQ ID NO: 88) | CDRL 1-1 (SEQ ID NO: 44) CDRL 2-1 (SEQ ID NO: 55) CDRL 3-1 (SEQ ID NO: 65) |
| 13H2 | H12 (SEQ ID NO: 116) | $V_H12$ (SEQ ID NO: 103) | CDRH 1-8 (SEQ ID NO: 21) CDRH 2-10 (SEQ ID NO: 32) CDRH 3-9 (SEQ ID NO: 42) | L15 (SEQ ID NO: 132) | $V_L15$ (SEQ ID NO: 89) | CDRL 1-10 (SEQ ID NO: 53) CDRL 2-9 (SEQ ID NO: 63) CDRL 3-8 (SEQ ID NO: 72) |
| 32H7 | H13 (SEQ ID NO: 117) | $V_H13$ (SEQ ID NO: 104) | CDRH 1-9 (SEQ ID NO: 22) CDRH 2-11 (SEQ ID NO: 33) CDRH 3-10 (SEQ ID NO: 43) | L16 (SEQ ID NO: 133) | $V_L16$ (SEQ ID NO: 90) | CDRL 1-11 (SEQ ID NO: 54) CDRL 2-10 (SEQ ID NO: 64) CDRL 3-9 (SEQ ID NO: 73) |

The anti-CGRP receptor antibodies used in the methods described herein can be monoclonal antibodies, polyclonal antibodies, recombinant antibodies, human antibodies, humanized antibodies, chimeric antibodies, multispecific antibodies, or antigen-binding fragments thereof. In certain embodiments, the anti-CGRP receptor antibody is a monoclonal antibody. In such embodiments, the anti-CGRP receptor antibody may be a human monoclonal antibody. In some embodiments, the anti-CGRP receptor antibody is a human antibody and can be of the IgG1-, IgG2-, IgG3-, or IgG4- type. Thus, the anti-CGRP receptor antibody may, in some embodiments, have a human IgG1 or human IgG2 constant domain. In one embodiment, the anti-CGRP receptor antibody is a monoclonal IgG1 antibody. In another embodiment, the anti-CGRP receptor antibody is a monoclonal IgG2 antibody.

Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a CGRP receptor immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds CGRP receptor.

Monoclonal antibodies secreted by a hybridoma cell line can be purified using any technique known in the art. Hybridomas or mAbs may be further screened to identify mAbs with particular properties, such as the ability to bind cells expressing CGRP receptor, ability to block or interfere with the binding of the CGRP ligand or $CGRP_{8-37}$ peptide, or the ability to functionally block the receptor, e.g., using a cAMP assay, e.g., as described herein.

In some embodiments, the anti-CGRP receptor antibodies used in the methods of the invention are chimeric or humanized antibodies based upon the foregoing sequences. A chimeric antibody is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855, which are hereby incorporated by reference. CDR grafting is described, for example, in U.S. Pat. No. 6,180,370, U.S. Pat. No. 5,693,762, U.S. Pat. No. 5,693,761, U.S. Pat. No. 5,585,089, and U.S. Pat. No. 5,530,101.

Generally, the goal of making a chimeric antibody is to create a chimera in which the number of amino acids from the intended species is maximized. One example is the "CDR-grafted" antibody, in which the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and U.S. Pat. No. 5,693,762; Jones et al., 1986, *Nature* 321:522-525; Riechmann et al., 1988, *Nature* 332:323-27; Verhoeyen et al., 1988, *Science* 239:1534-1536), In one aspect, the CDRs of the light and heavy chain variable regions of the antibodies provided herein (see, Tables 2 and 3) are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, $V_H12$, and $V_H13$, and/or $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, and $V_L17$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of an anti-CGRP receptor antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In particular embodiments, the anti-CGRP receptor antibodies or antigen-binding fragments thereof used in the methods of the invention are fully human antibodies. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. No. 5,545,807; U.S. Pat. No. 6,713,610; U.S. Pat. No. 6,673,986; U.S. Pat. No. 6,162,963; U.S. Pat. No. 5,545,807; U.S. Pat. No. 6,300,129; U.S. Pat. No. 6,255,458; U.S. Pat. No. 5,877,397; U.S. Pat. No. 5,874,299 and U.S. Pat. No. 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N. Y Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N. Y Acad. Sci.* 764:536-546; Fishwild et al., 1996, *Nature Biotechnology* 14:845-851; the foregoing references are hereby incorporated by reference in their entirety for all purposes. See, further U.S. Pat. No. 5,545,806; U.S. Pat. No. 5,569,825; U.S. Pat. No. 5,625,126; U.S. Pat. No. 5,633,425; U.S. Pat. No. 5,789,650; U.S. Pat. No. 5,877,397; U.S. Pat. No. 5,661,016; U.S. Pat. No. 5,814,318; U.S. Pat. No. 5,874,299; and U.S. Pat. No. 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate anti-CGRP receptor antibodies.

Some of the anti-CGRP receptor antibodies or binding fragments that can be used in the methods described herein are variant forms of the anti-CGRP receptor antibodies disclosed above (e.g., those having the sequences listed in Tables 2-7). For instance, the anti-CGRP receptor antibody or binding fragment may have one or more conservative amino acid substitutions in one or more of the heavy or light chains, variable regions or CDRs listed in Tables 2-7. Conservative amino acid substitutions may involve exchange of an amino acid with another amino acid that has a common side chain property (e.g. hydrophobic, neutral hydrophilic, acidic, basic, and aromatic). For example, a conservative substitution includes substitution of a hydrophobic amino acid (e.g. norleucine, methionine, alanine, valine, leucine, or isoleucine) with another hydrophobic amino acid. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 8.

TABLE 8

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of anti-CGRP receptor antibodies as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for CGRP receptor neutralizing activity, thus yielding information regarding which amino acids can be changed and which must not be changed. In other words, based on information gathered from such routine experiments, one skilled in the art can readily determine the amino acid positions where further substitutions should be avoided either alone or in combination with other mutations.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteine residues.

The anti-CGRP receptor antibodies or binding fragments thereof that are of one subclass can be changed to antibodies or binding fragments from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, Methods Mol. Biol. 178:303-316.

Accordingly, the anti-CGRP receptor antibodies described herein include those comprising, for example, the variable domain combinations described above having a desired isotype (for example, IgA, IgG1, IgG2, IgG3, IgG4, IgE, and IgD) as well as Fab or F(ab')2 fragments thereof. Moreover, if an IgG4 is desired, it may also be desired to introduce a point mutation (CPSCP->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology 10:779.

Conservative modifications may be made to the heavy and light chain variable regions described in Table 4, or the CDRs described in Tables 2 and 3 (and corresponding modifications to the encoding nucleic acids) to produce a CGRP receptor antibody or binding fragment thereof having certain desirable functional and biochemical characteristics. Methods for achieving such modifications are described above.

The anti-CGRP receptor antibodies or binding fragments thereof for use in the methods of the invention may be prepared by any of a number of conventional techniques. For example, the anti-CGRP receptor antibodies described herein may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Anti-CGRP receptor antibodies or binding fragments thereof can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; U.S. Pat. No. 4,912,040; U.S. Pat. No. 4,740,461; U.S. Pat. No. 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., CH1, CH2 and/or CH3); a heavy chain variable region; and/or another scaffold portion of an anti-CGRP receptor antibody. These nucleic acid sequences are inserted into an appropriate expression vector using standard ligation techniques. In one embodiment, the heavy or light chain constant region is appended to the C-terminus of the anti-CGRP receptor-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, Biotech. Biotechnol. Bioeng. 84:439-44, which is hereby incorporated by reference. Additional suitable expression vectors are discussed, for example, in Methods Enzymol., vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the anti-CGRP receptor antibody coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the anti-CGRP receptor antibody from the host cell. Affinity purification can be accomplished, for example, by column chromatography using antibodies against the tag as an affinity matrix. Optionally, the tag can subsequently be removed from the purified anti-CGRP receptor antibody by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using known methods for nucleic acid synthesis.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an anti-CGRP receptor antibody. As a result, increased quantities of a polypeptide such as an anti-CGRP receptor antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding an anti-CGRP receptor antibody or binding fragment. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising an anti-CGRP receptor antibody or binding fragment by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); promoter and regulatory sequences from the metallothionine gene (Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315:115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-fetoprotein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1:161-171); the beta-globin gene control region that is active in myeloid cells (Mogram et al., 1985, Nature 315:338-340; Kollias et al., 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234:1372-1378).

An enhancer sequence may be inserted into the vector to increase transcription of DNA encoding light chain or heavy chain comprising an anti-CGRP receptor antibody or binding fragment thereof by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin 7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846. Other useful signal peptides for expressing the anti-CGRP receptor antibodies or binding fragments described herein are the signal peptides having the sequence set forth in SEQ ID NO: 135 or SEQ ID NO: 136.

The expression vectors for recombinant production of the anti-CGRP receptor antibodies or binding fragments thereof described herein may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an anti-CGRP receptor antibody or binding fragment has been inserted into the proper site of the vector, the completed vector may be inserted into a suitable host cell for amplification and/or polypeptide expression. The transformation of an expression vector for an antigen-binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein (e.g. antibody or binding fragment) that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies or binding fragments with CGRP receptor binding properties. In another embodiment, a cell line from the B cell lineage that does not make its own antibody but has a capacity to make and secrete a heterologous antibody can be selected.

The anti-CGRP receptor antibody or binding fragment thereof is generally administered to the patient in a pharmaceutical composition, which can include pharmaceutically-acceptable carriers, excipients, or diluents. "Pharmaceutically-acceptable" refers to molecules, compounds, and compositions that are non-toxic to human recipients at the dosages and concentrations employed and/or do not produce allergic or adverse reactions when administered to humans. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

In some embodiments, the selection of carriers and excipients for incorporation into the pharmaceutical compositions influences the physical state, stability, rate of in vivo release and rate of in vivo clearance of the anti-CGRP receptor antibodies or binding fragments thereof. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration.

In certain embodiments of the methods described herein, the anti-CGRP receptor antibody or binding fragment thereof is administered to the patient parenterally. Parenteral administration includes intraperitoneal, intramuscular, intravenous, intraarterial, intradermal, subcutaneous, intracerebral, intracerebroventricular, and intrathecal administration. In one particular embodiment, the pharmaceutical composition comprising a therapeutically effective amount of an anti-CGRP receptor antibody or binding fragment thereof is administered to the patient subcutaneously. In these and other embodiments in which the pharmaceutical composition is administered by parenteral injection, the pharmaceutical composition can be administered to the patient with a syringe. In some embodiments, the syringe is pre-filled with the pharmaceutical composition. In other embodiments in which the pharmaceutical composition is administered to the patient by parenteral injection, such as subcutaneous injection, the pharmaceutical composition is administered with an injection device, including devices for self-administration. Such devices are commercially available and include, but are not limited to, autoinjectors, dosing pens, microinfusion pumps, and pre-filled syringes. Exemplary devices for administering a pharmaceutical composition comprising a therapeutically effective amount of an anti-CGRP receptor antibody or binding fragment thereof according to the methods of the invention include autoinjectors (e.g., SureClick®, EverGentle®, Avanti®, DosePro®, Molly®, and Leva®), pen injection devices (e.g., Madie® pen injector, DCP™ pen injector, BD Vystra™ disposable pen, BD™ reusable pen), and pre-filled syringes (BD Sterifill™, BD Hypak™, pre-filled syringes from Baxter). In some embodiments, the pharmaceutical composition comprising a therapeutically effective amount of an anti-CGRP receptor antibody or binding fragment is administered to the patient with a pre-filled syringe. In other embodiments, the pharmaceutical composition comprising a therapeutically effective amount of an anti-CGRP receptor antibody or binding fragment is administered to the patient with an autoinjector. In certain related embodiments, the injection volume is about 1 mL or less.

In one embodiment, the anti-CGRP receptor antibody or binding fragment thereof is administered to a patient at a dose of about 70 mg per month to prevent or reduce the occurrence of migraine headache in the patient, wherein the dose is delivered by a single subcutaneous injection. In related embodiments, the single subcutaneous injection is delivered with a pre-filled syringe. In other related embodiments, the single subcutaneous injection is delivered with an autoinjector. In certain embodiments, the patient may have or be diagnosed with episodic migraine. In other embodiments, the patient may have or be diagnosed with chronic migraine.

In another embodiment, the anti-CGRP receptor antibody or binding fragment thereof is administered to a patient at a dose of about 140 mg per month to prevent or reduce the occurrence of migraine headache in the patient, wherein the dose is delivered by a single subcutaneous injection. In such embodiments, the single injection may be delivered with a pre-filled syringe or autoinjector. In one embodiment, the 140 mg monthly dose of anti-CGRP receptor antibody or binding fragment thereof is administered to the patient through two consecutive injections each comprising a 70 mg dose. In such embodiments, the two consecutive injections can be delivered using two pre-filled syringes or two autoinjectors, each of which contains a 70 mg dose. In some embodiments, the patient may have or be diagnosed with episodic migraine. In other embodiments, the patient may have or be diagnosed with chronic migraine.

Illustrative pharmaceutical forms suitable for parenteral injection include sterile aqueous solutions or dispersions and sterile powders for the extemporaneous preparation of sterile injectable solutions or dispersions. Preferably, the pharmaceutical form is sterile and is sufficiently fluid to allow for delivery via a syringe (i.e., the formulation is not excessively viscous so as to prevent passage through a syringe). Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions can be placed into a container having a sterile access port, for example, an intravenous solution bag or vial having a stopper pierceable by a hypodermic injection needle. Parenteral compositions can also be stored in syringes, autoinjector devices, or pen injection devices or cartridges adapted for use with such injection devices.

In certain embodiments, the preparation of a pharmaceutical composition to be administered according to the methods of the invention can involve the formulation of the anti-CGRP receptor antibody or binding fragment thereof with an agent, such as injectable microspheres, bio-erodible particles, polymeric compounds (such as polylactic acid or polyglycolic acid), beads or liposomes, that may provide controlled or sustained release of the antibody or binding fragment which can be delivered via depot injection. In certain embodiments, hyaluronic acid may also be used, having the effect of promoting sustained duration in the circulation. In certain embodiments, implantable drug delivery devices may be used to deliver the anti-CGRP receptor antibody or binding fragment.

In some embodiments, the pharmaceutical composition comprising a therapeutically effective amount of an anti-CGRP receptor antibody or binding fragment thereof to be administered to a patient according to the methods of the invention further comprises a buffer. Buffers are used to maintain the composition at physiological pH or at a slightly lower pH, typically within a pH range from about 4.5 to about 6.5. Suitable buffers include, but are not limited to, glutamate, acetate, Tris, citrate, histidine, succinate, and phosphate buffers. In certain embodiments, the pharmaceutical composition administered according to the methods described herein comprises an acetate buffer. The acetate buffer can be made from an acetate salt, for example, sodium acetate. Other salts can be used, for example such as potassium, ammonium, calcium or magnesium salts of acetate. Pharmaceutical compositions comprising an acetate buffer typically have a pH of about 4.5 to about 5.5 or a pH of about 4.8 to about 5.2, including a pH of about 4.5, about 4.6, about 4.7, about 4.8, about 4.9, about 5.0, about 5.1, about 5.2, about 5.3, about 5.4, and about 5.5.

The pharmaceutical composition comprising a therapeutically effective amount of an anti-CGRP receptor antibody or binding fragment thereof may further comprise a surfactant. The term "surfactant" as used herein refers to a substance that functions to reduce the surface tension of a liquid in which it is dissolved. Surfactants can be included in pharmaceutical compositions for a variety of purposes including, for example, to prevent or control aggregation, particle formation and/or surface adsorption in liquid formulations or to prevent or control these phenomena during the lyophilization and/or reconstitution process in lyophilized formulations. Surfactants include, for example, amphipathic organic compounds that exhibit partial solubility in both organic solvents and aqueous solutions. General characteristics of surfactants include their ability to reduce the surface tension of water, reduce the interfacial tension between oil and water and also form micelles. Surfactants that may be incorporated into the pharmaceutical compositions used in the methods of the invention include both non-ionic and ionic surfactants. Suitable non-ionic surfactants include, but are not limited to, alkyl poly (ethylene oxide), alkyl polyglucosides, such as octyl glucoside and decyl maltoside, fatty alcohols, such as cetyl alcohol and oleyl alcohol, cocamide MEA, cocamide DEA, and cocamide TEA. Specific examples of non-ionic surfactants include the polysorbates including, for example, polysorbate 20, polysorbate 28, polysorbate 40, polysorbate 60, polysorbate 65, polysorbate 80, polysorbate 81, polysorbate 85 and the like; the poloxamers including, for example, poloxamer 188, also known as poloxalkol or poly(ethylene oxide)-poly(propylene oxide), poloxamer 407 or polyethylene-polypropylene glycol and the like, and polyethylene glycol (PEG). Suitable ionic surfactants include, for example, anionic, cationic and zwitterionic surfactants. Anionic surfactants include, but are not limited to, sulfonate-based or carboxylate-based surfactants such as soaps, fatty acid salts, sodium dodecyl sulfate (SDS), ammonium lauryl sulfate and other alkyl sulfate salts. Cationic surfactants include, but are not limited to, quaternary ammonium-based surfactants such as cetyl trimethylammonium bromide (CTAB), other alkyltrimethylammonium salts, cetyl pyridinium chloride, polyethoxylated tallow amine (POEA) and benzalkonium chloride. Zwitterionic or amphoteric surfactants include, for example, dodecyl betaine, dodecyl dimethylamine oxide, cocamidopropyl betaine and coco ampho glycinate. In certain embodiments, the pharmaceutical compositions administered according to the methods described herein comprise a non-ionic surfactant. In one embodiment, the non-ionic surfactant is polysorbate 20. In another embodiment, the non-ionic surfactant is polysorbate 80.

In certain embodiments, the pharmaceutical composition comprising a therapeutically effective amount of an anti-CGRP receptor antibody or binding fragment thereof further comprises a stabilizing agent. As used herein, the term "stabilizing agent" refers to an excipient that stabilizes the native conformation of the polypeptide or antibody and/or prevents or reduces the physical or chemical degradation of the polypeptide or antibody. Suitable stabilizing agents include, but are not limited to, polyols (e.g. sorbitol, glycerol, mannitol, xylitol, maltitol, lactitol, erythritol and threitol), sugars (e.g., fructose, glucose, glyceraldehyde, lactose, arabinose, mannose, xylose, ribose, rhamnose, galactose maltose, sucrose, trehalose, sorbose, sucralose, melezitose and raffinose), and amino acids (e.g., glycine, methionine, proline, lysine, arginine, histidine, or glutamic acid). In some embodiments, the pharmaceutical composition comprises a sugar as a stabilizing agent. In these and other embodiments, the sugar is sucrose.

In certain embodiments, a pharmaceutical composition useful for the prophylactic treatment of migraine headache according to the methods described herein comprises about 35 mg/ml to about 210 mg/ml of anti-CGRP receptor antibody or binding fragment thereof, about 8 mM to about 20 mM sodium acetate, about 0.002% to about 0.015% weight/volume (w/v) polysorbate, and about 7% to about 10% w/v sucrose. In other embodiments, the pharmaceutical composition comprises about 70 mg/ml to about 140 mg/ml of anti-CGRP receptor antibody or binding fragment thereof, about 10 mM to about 15 mM sodium acetate, about 0.008% to about 0.012% w/v polysorbate, and about 8% to about 9% w/v sucrose. The pH of these compositions is in the range of about 4.8 to about 5.5 (e.g., pH of about 4.8, about 5.0, about 5.2, or about 5.4).

In one embodiment, a pharmaceutical composition to be administered according to the methods of the invention comprises about 70 mg/ml anti-CGRP receptor antibody or binding fragment thereof, about 10 mM sodium acetate, about 0.004% w/v polysorbate 20, and about 9% w/v sucrose at a pH of 5.2±0.2. In another embodiment, the pharmaceutical composition comprises about 70 mg/ml anti-CGRP receptor antibody or binding fragment thereof, about 10 mM sodium acetate, about 0.004% w/v polysorbate 80, and about 9% w/v sucrose at a pH of 5.2±0.2. In another embodiment, the pharmaceutical composition comprises about 140 mg/ml anti-CGRP receptor antibody or binding fragment thereof, about 10 mM sodium acetate, about 0.004% w/v polysorbate 20, and about 9% w/v sucrose at a pH of 5.2±0.2. In yet another embodiment, the pharmaceutical composition comprises about 140 mg/ml anti-CGRP receptor antibody or binding fragment thereof, about 10 mM sodium acetate, about 0.004% w/v polysorbate 80, and about 9% w/v sucrose at a pH of 5.2±0.2. In another embodiment, the pharmaceutical composition comprises about 70 mg/ml anti-CGRP receptor antibody or binding fragment thereof, about 10 mM sodium acetate, about 0.010% w/v polysorbate 20, and about 9% w/v sucrose at a pH of 5.2±0.2. In still another embodiment, the pharmaceutical composition comprises about 70 mg/ml anti-CGRP receptor antibody or binding fragment thereof, about 10 mM sodium acetate, about 0.010% w/v polysorbate 80, and about 9% w/v sucrose at a pH of 5.2±0.2. In one particular embodiment, the pharmaceutical composition comprises about 140 mg/ml anti-CGRP receptor antibody or binding fragment thereof, about 10 mM sodium acetate, about 0.010% w/v polysorbate 20, and about 9% w/v sucrose at a pH of 5.2±0.2. In another particular embodiment, the pharmaceutical composition comprises about 140 mg/ml anti-CGRP receptor antibody or binding fragment thereof, about 10 mM sodium acetate, about 0.010% w/v polysorbate 80, and about 9% w/v sucrose at a pH of 5.2±0.2.

In certain embodiments, a pharmaceutical composition to be administered according to the methods of the invention comprises about 70 mg/ml anti-CGRP receptor antibody or binding fragment thereof, about 15 mM sodium acetate, about 0.010% w/v polysorbate 20, and about 8.2% w/v sucrose at a pH of 5.2±0.2. In one particular embodiment, the pharmaceutical composition comprises about 70 mg/ml anti-CGRP receptor antibody or binding fragment thereof, about 15 mM sodium acetate, about 0.010% w/v polysorbate 80, and about 8.2% w/v sucrose at a pH of 5.2±0.2. In another particular embodiment, the pharmaceutical composition comprises about 140 mg/ml anti-CGRP receptor antibody or binding fragment thereof, about 15 mM sodium acetate, about 0.010% w/v polysorbate 80, and about 8.2% w/v sucrose at a pH of 5.2±0.2. In another embodiment, the pharmaceutical composition comprises about 140 mg/ml anti-CGRP receptor antibody or binding fragment thereof, about 15 mM sodium acetate, about 0.010% w/v polysorbate 20, and about 8.2% w/v sucrose at a pH of 5.2±0.2. In yet another embodiment, the pharmaceutical composition comprises about 70 mg/ml anti-CGRP receptor antibody or binding fragment thereof, about 15 mM sodium acetate, about 0.010% w/v polysorbate 80, and about 8.5% w/v sucrose at a pH of 5.2±0.2. In still another embodiment, the pharmaceutical composition comprises about 140 mg/ml anti-CGRP receptor antibody or binding fragment thereof, about 15 mM sodium acetate, about 0.010% w/v polysorbate 80, and about 8.5% w/v sucrose at a pH of 5.2±0.2. In some embodiments, the pharmaceutical composition comprises about 70 mg/ml anti-CGRP receptor antibody or binding fragment thereof, about 15 mM sodium acetate, about 0.010% w/v polysorbate 20, and about 8.5% w/v sucrose at a pH of 5.2±0.2. In other embodiments, the pharmaceutical composition comprises about 140 mg/ml anti-CGRP receptor antibody or binding fragment thereof, about 15 mM sodium acetate, about 0.010% w/v polysorbate 20, and about 8.5% w/v sucrose at a pH of 5.2±0.2.

In some embodiments, a pharmaceutical composition to be administered according to the methods of the invention comprises about 70 mg/ml anti-CGRP receptor antibody or binding fragment thereof, about 20 mM sodium acetate, about 0.010% w/v polysorbate 20, and about 8.2% w/v sucrose at a pH of 5.2±0.2. In one embodiment, the pharmaceutical composition comprises about 140 mg/ml anti-CGRP receptor antibody or binding fragment thereof, about 20 mM sodium acetate, about 0.010% w/v polysorbate 20, and about 8.2% w/v sucrose at a pH of 5.2±0.2. In another embodiment, the pharmaceutical composition comprises about 70 mg/ml anti-CGRP receptor antibody or binding fragment thereof, about 20 mM sodium acetate, about 0.010% w/v polysorbate 80, and about 8.2% w/v sucrose at a pH of 5.2±0.2. In another embodiment, the pharmaceutical composition comprises about 140 mg/ml anti-CGRP receptor antibody or binding fragment thereof, about 20 mM sodium acetate, about 0.010% w/v polysorbate 80, and about 8.2% w/v sucrose at a pH of 5.2±0.2. In yet another embodiment, the pharmaceutical composition comprises about 70 mg/ml anti-CGRP receptor antibody or binding fragment thereof, about 20 mM sodium acetate, about 0.010% w/v polysorbate 80, and about 8.5% w/v sucrose at a pH of 5.2±0.2. In another embodiment, the pharmaceutical composition comprises about 140 mg/ml anti-CGRP receptor antibody or binding fragment thereof, about 20 mM sodium acetate, about 0.010% w/v polysorbate 80, and about 8.5% w/v sucrose at a pH of 5.2±0.2. In still another embodiment, the pharmaceutical composition comprises about 70 mg/ml anti-CGRP receptor antibody or binding fragment thereof, about 20 mM sodium acetate, about 0.010% w/v polysorbate 20, and about 8.5% w/v sucrose at a pH of 5.2±0.2. In another embodiment, the pharmaceutical composition comprises about 140 mg/ml anti-CGRP receptor antibody or binding fragment thereof, about 20 mM sodium acetate, about 0.010% w/v polysorbate 20, and about 8.5% w/v sucrose at a pH of 5.2±0.2.

Any of the anti-CGRP receptor antibodies or binding fragments described herein, including the specific anti-CGRP receptor antibodies described in Table 7, can be incorporated into any of the pharmaceutical compositions described above and administered to a patient according to the methods described herein. In certain embodiments, the anti-CGRP receptor antibody is the 4E4 antibody described in Table 7 or a binding fragment thereof. In other particular embodiments, the anti-CGRP receptor antibody is the 9F5 antibody described in Table 7 or a binding fragment thereof.

Any of the above-described pharmaceutical compositions can be incorporated into a self-administration injection device. Thus, the present invention also includes injection devices suitable for the prophylactic treatment of migraine headache in a patient in need thereof. In certain embodiments, the invention provides a pre-filled syringe comprising a pharmaceutical composition comprising an anti-CGRP receptor antibody or binding fragment thereof, an acetate buffer, sucrose, and polysorbate. In one embodiment, the pre-filled syringe comprises a pharmaceutical composition comprising about 70 mg/ml anti-CGRP receptor antibody or binding fragment thereof, about 15 mM sodium acetate, about 0.010% w/v polysorbate 80, and about 8.2% w/v sucrose at a pH of 5.2±0.2. In another embodiment, the pre-filled syringe comprises a pharmaceutical composition comprising about 140 mg/ml anti-CGRP receptor antibody or binding fragment thereof, about 15 mM sodium acetate, about 0.010% w/v polysorbate 80, and about 8.2% w/v sucrose at a pH of 5.2±0.2. In another embodiment, the pre-filled syringe comprises a pharmaceutical composition comprising about 70 mg/ml anti-CGRP receptor antibody or binding fragment thereof, about 15 mM sodium acetate, about 0.010% w/v polysorbate 80, and about 8.5% w/v sucrose at a pH of 5.2±0.2. In yet another embodiment, the pre-filled syringe comprises a pharmaceutical composition comprising about 140 mg/ml anti-CGRP receptor antibody or binding fragment thereof, about 15 mM sodium acetate, about 0.010% w/v polysorbate 80, and about 8.5% w/v sucrose at a pH of 5.2±0.2. In certain embodiments, the injection volume of the pre-filled syringe is about 1 ml or less (e.g. 0.5 ml).

In some embodiments, the invention provides an autoinjector comprising a pharmaceutical composition comprising an anti-CGRP receptor antibody or binding fragment thereof, an acetate buffer, sucrose, and polysorbate. In one embodiment, the autoinjector comprises a pharmaceutical composition comprising about 70 mg/ml anti-CGRP receptor antibody or binding fragment thereof, about 15 mM sodium acetate, about 0.010% w/v polysorbate 80, and about 8.2% w/v sucrose at a pH of 5.2±0.2. In another embodiment, the autoinjector comprises a pharmaceutical composition comprising about 140 mg/ml anti-CGRP receptor antibody or binding fragment thereof, about 15 mM sodium acetate, about 0.010% w/v polysorbate 80, and about 8.2% w/v sucrose at a pH of 5.2±0.2. In another embodiment, the autoinjector comprises a pharmaceutical composition comprising about 70 mg/ml anti-CGRP receptor antibody or binding fragment thereof, about 15 mM sodium acetate, about 0.010% w/v polysorbate 80, and about 8.5% w/v sucrose at a pH of 5.2±0.2. In yet another embodiment, the autoinjector comprises a pharmaceutical composition comprising about 140 mg/ml anti-CGRP receptor antibody or binding fragment thereof, about 15 mM sodium acetate, about 0.010% w/v polysorbate 80, and about 8.5% w/v sucrose at a pH of 5.2±0.2. In certain embodiments, the injection volume of the autoinjector is about 1 ml or less (e.g. 0.5 ml).

The invention also includes administering to a patient an anti-CGRP receptor antibody or binding fragment thereof in combination with one or more agents suitable for the acute or prophylactic treatment of migraine headache or other headache disorder described herein. The term "combination therapy" as used herein encompasses the administration of the two compounds (e.g. anti-CGRP receptor antibody or binding fragment and additional agent) in a sequential manner (i.e. each compound is administered at a different time in any order) as well as administration of the two compounds in a substantially simultaneous manner. Substantially simultaneous administration includes concurrent administration and can be accomplished by administering a single formulation comprising both compounds (e.g. a single capsule or other formulation comprising a fixed ratio of both compounds or a pre-filled syringe having a fixed ratio of each compound) or concurrently administering separate formulations containing each of the compounds.

In some embodiments, the methods of the invention comprise administering an anti-CGRP receptor antibody or binding fragment thereof with a second agent that modulates CGRP receptor signaling. For example, the anti-CGRP receptor antibody or binding fragment can be administered in combination with a second CGRP receptor antagonist to prophylactically treat migraine headache in a patient in need thereof. Other CGRP receptor antagonists include small molecule inhibitors of the CGRP receptor, such as those described in U.S. Patent Publication No. 20060142273 and U.S. Pat. Nos. 7,842,808; 7,772,244; 7,754,732; 7,569,578; 8,685,965; 8,569,291; 8,377,955; 8,372,859; 8,143,266; 7,947,677; and 7,625,901, all of which are hereby incorporated by reference in their entireties. CGRP receptor antagonists can also include peptide antagonists of the receptor, such as those described in U.S. Pat. No. 8,168,592, which is hereby incorporated by reference in its entirety. In some embodiments, the anti-CGRP receptor antibody or binding fragment can be administered in combination with an agent that interferes with the binding of the CGRP ligand to the CGRP receptor to prophylactically treat migraine headache in a patient in need thereof. An agent that interferes with the binding of the CGRP ligand to the CGRP receptor can be a decoy or soluble CGRP receptor or other protein that binds to the CGRP ligand, such as an anti-CGRP antibody. Anti-CGRP antibodies are known in the art and are described, for example, in WO 2007/054809; WO 2007/076336; WO 2011/156324; and WO 2012/162243, all of which are hereby incorporated by reference in their entireties.

In certain embodiments, the methods of the invention comprise administering an anti-CGRP receptor antibody or binding fragment thereof with a second anti-migraine agent. The second anti-migraine agent may be an agent used for the acute treatment of migraines such as triptans (e.g., almotriptan, frovatriptan, rizatriptan, sumatriptan, naratriptan, eletriptan, and zolmitriptan), ergotamines (e.g., dihydroergotamine and ergotamine with caffeine), non-steroidal anti-inflammatory drugs (e.g., acetylsalicylic acid, ibuprofen, naproxen, indomethacin, and diclofenac), and opioids (e.g., codeine, morphine, hydrocodone, fentanyl, meperidine, and oxycodone). In some embodiments, the second anti-migraine agent is an agent used for the prophylactic treatment of migraines, such as an antiepileptic (e.g. topiramate), beta-blocker (e.g. propranolol) or an anti-depressant (e.g. amitriptyline). In other embodiments, the second anti-migraine agent is an agent that modulates activity of the pituitary adenylate cyclase-activating polypeptide type I receptor (PAC1 receptor). An agent that modulates activity of the PAC1 receptor includes antibodies or other binding proteins that bind to the PAC1 receptor, such as those described in WO 2014/144632, which is hereby incorporated by reference in its entirety.

The present invention also includes kits for prophylactically treating migraine headache in a patient in need thereof. In one embodiment, the kit comprises a pharmaceutical composition of an anti-CGRP receptor antibody or binding fragment described herein and packaging material that provides instructions regarding the use of the pharmaceutical compositions. The pharmaceutical composition of the kit may be present in a container, such as a vial or syringe. The pharmaceutical composition may be provided as a solution, suspension, gel, emulsion, solid, crystal, or as a dehydrated or lyophilized powder. In embodiments in which the pharmaceutical composition is provided as a powder, the kit may also comprise diluents (e.g. water, saline, phosphate-buffer saline) necessary to reconstitute the pharmaceutical composition as well as instructions for preparing the composition for administration. In some embodiments, the kits comprise an injection device for self-administration (e.g. pre-filled syringe or autoinjector) pre-filled with the pharmaceutical composition as described herein. Any of the pre-filled syringes and autoinjectors described above can be included in kits.

The following examples, including the experiments conducted and the results achieved, are provided for illustrative purposes only and are not to be construed as limiting the scope of the appended claims.

EXAMPLES

Example 1. Pharmacokinetic/Pharmacodynamic Modeling of Monoclonal Antibody AMG 334 to Characterize Concentration Relationship with Capsaicin-Induced Increase in Dermal Blood Flow in Healthy Subjects and Migraine Patients AMG 334 (also referred to herein as antibody 4E4) is a fully human IgG2 monoclonal antibody that binds to the human CGRP receptor with high in vitro potency. Inhibition of capsaicin (CAP)-induced increases in dermal blood flow (DBF) has been used extensively as a translational model to characterize the pharmacological effect of CGRP receptor antagonists. This validated model was used to characterize the pharmacological effect of AMG 334 and to quantify the inhibitory effect of AMG 334 on CAP-induced increases in DBF in healthy subjects (HS) and migraine patients (MP) after single and multiple doses of AMG 334.

The analysis dataset included 52 subjects (40 HS, 12 MP) who received a single subcutaneous (SC) dose of AMG 334 (1, 7, 21, 70, 140, or 210 mg) or placebo and 40 subjects (24 HS, 16 MP) who received 3 consecutive SC doses of AMG 334 (21, 70, or 140 mg) or placebo, every 4 weeks. See Table 9 below. Repeated CAP challenges and DBF measurements were performed within the same subjects, using laser Doppler imaging, at multiple study visits to estimate the inhibitory effect of AMG 334 on DBF pre- and post-CAP administration. Serum AMG 334 concentrations were determined at the corresponding time points for DBF measurements with additional samples collected at other time points for pharmacokinetic characterization. A population pharmacokinetic-pharmacodynamic (PK-PD) modeling approach was implemented to evaluate AMG 334 concentration-DBF relationship. Effects of body weight (44.6-104 kg), sex (male vs female), age (18-53 years), and disease population (MP vs HS) on PK and PD parameters were assessed in the model.

Figure 2:
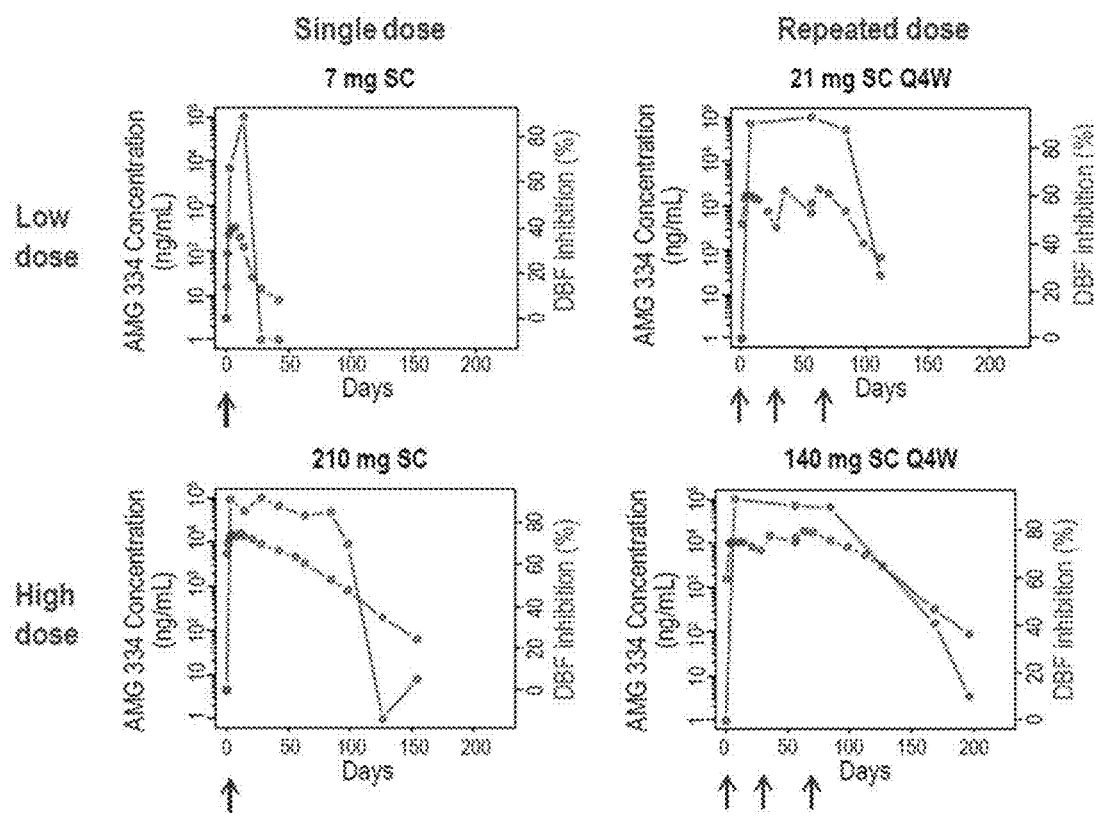
FIG. 2 shows the percentage inhibition of capsaicin-induced dermal blood flow (DBF) and serum concentration of AMG 334 monoclonal antibody over time following single dose and repeated dose (once every four weeks; Q4W) subcutaneous (SC) administration of AMG 334 to healthy human subjects and migraine patients. The duration of maximum DBF inhibition is consistent with the dose concentration-DBF relationship.

AMG 334 PK was best characterized by a receptor-mediated drug disposition model, which explained the concentration/dose-dependence of AMG 334 clearance and distribution. Complete SC absorption occurred approximately 10 days after dosing. For a typical subject (70 kg) who received a 70 mg SC dose, the estimated elimination half-life was 21 days, which is typical for a monoclonal antibody. The half-life of AMG 334 was shortened (i.e., <21 days) with rapid antibody elimination, when its concentration was approximately <700 ng/mL, presumably because most of AMG 334 was bound by the target receptor, leaving less circulating, unbound AMG 334 available for elimination. AMG 334 significantly inhibited post-CAP DBF, but had no significant effect on pre-CAP DBF. The PK-PD model estimated a mean baseline, CAP-induced DBF increase of 390 AU and maximum DBF inhibition of 90%. The AMG 334 concentrations required for 50% (EC50) and 99% (EC99) of maximal inhibition were 218 ng/mL and 1140 ng/mL, respectively. See FIG. 1. Consequently, all doses >7 mg produced concentrations above EC99 or the maximal DBF inhibition; the duration of maximum inhibition increased with increasing dose and was sustained after repeated dosing. See FIG. 2. AMG 334 exposure, but not DBF, decreased with increased body weight. No differences in PK and PD were noted between HS and MP after adjusting for body weight.

AMG 334 results in a potent and reproducible inhibition of CAP-induced DBF, indicating complete peripheral CGRP receptor blockade in HS and MP. Body weight was the only covariate affecting PK, but did not affect PD. The long half-life of AMG 334 and robust concentration-DBF relationship indicates prolonged inhibition of CGRP receptors.

Example 2. Phase 1, Randomized, Double-Blind, Placebo-Controlled, Single-Dose and Multiple Dose Studies of AMG 334 in Healthy Subjects and Migraine Patients Migraines are disabling headaches for which calcitonin gene-related peptide (CGRP) is thought to be involved. AMG 334 (4E4 antibody) is a fully human monoclonal antibody against the CGRP receptor. In these phase 1, randomized, placebo controlled, single-dose (SD) and multiple-dose (MD) studies, the pharmacokinetics (PK), pharmacodynamics (PD) and safety of AMG 334 in healthy subjects and migraineurs were evaluated.

In the SD study, subjects received single, escalating doses of AMG 334 (n=42) of 1 to 210 mg SC, 140 mg IV, or matching placebo (n=18). In the MD study, subjects received multiple doses of AMG 334 (n=35) of 21 to 280 mg SC or placebo (n=12) on days 1, 29, and 57. PK and safety were evaluated in both studies; PK measurements included maximum concentration ($C_{max}$), area under the concentration-time curve from time zero to the last quantifiable concentration ($AUC_{last}$), and time to maximum concentration ($t_{max}$). Inhibition of capsaicin-induced dermal blood flow (DBF) by AMG 334 was used to measure CGRP receptor antagonism in both studies; $E_{max}$ represented the maximum percent inhibition. In the SD study, a sigmoidal $E_{max}$ PK/PD model was applied to analyze the relationship between AMG 334 serum exposure and inhibition of capsaicin-induced increase in DBF. Continuous, 24-hour ambulatory blood pressure monitoring (ABPM) was conducted in the MD study, approximately 7 days after each dose.

Figure 3A:
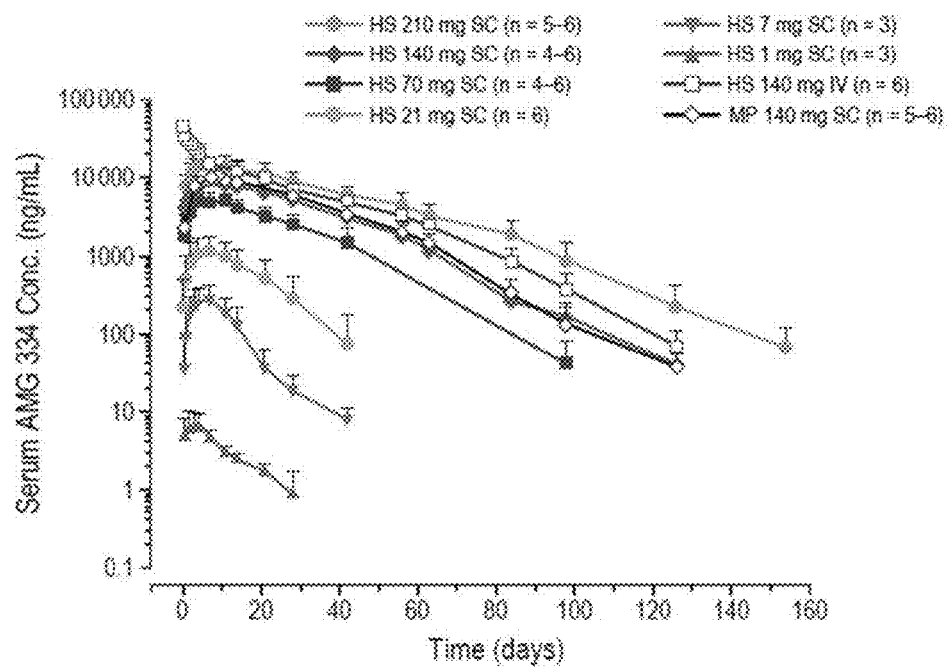
FIG. 3A depicts the mean serum AMG 334 concentration—time profiles in healthy human subjects (HS) and migraine patients (MP) receiving single, escalating doses of AMG 334 or matching placebo either subcutaneously (SC) or intravenously (IV).

In the SD study, 42 subjects received AMG 334 (36 healthy, 6 migraine); 18 received placebo (12 healthy, 6 migraine). Detectable serum levels of AMG 334 were observed 30 to 160 days postdose, with doses 70 mg and higher leading to detectable levels for 100 days or greater postdosing. See FIG. 3A. After single SC administration, AMG 334 exhibited nonlinear PK; AMG 334 exposure increased more than dose proportionally from 1 to 70 mg and approximately dose proportionally from 70 to 210 mg. See Table 10 below. The mean $AUC_{last}$ increased 3.8-fold from 171 to 652 μg·day/mL and mean $C_{max}$ increased 2.4-fold from 6.25 to 15.2 μg/mL, following the 3-fold increase in dose from 70 to 210 mg (Table 10). The median $t_{max}$ ranged from 4 to 11 days throughout the dose range (Table 10). The relative exposure area under the concentration time curve (AUC) for SC administration compared with IV administration was approximately 54% for the 140-mg

TABLE 9

Characteristics of Subjects Included in Population PK/PD Modeling

| | Single dose N = 52 | | Repeated dose N = 40 | |
|---|---|---|---|---|
| | Healthy N = 40 | Migraine N = 12 | Healthy N = 24 | Migraine N = 16 |
| Dose regimens | placebo, 1, 7, 21, 70, 140, or 210 mg SC | placebo or 140 mg SC | placebo, 21, 70, or 140 mg SC Q4W × 3 doses | placebo, 21 or 140 mg SC Q4W × 3 doses |
| Weight (kg)* | 80.3 (9.28) | 64.5 (11) | 75.5 (11.5) | 69.2 (14.1) |
| Age (y)* | 26.8 (6.48) | 26.2 (9.56) | 30.1 (10.3) | 32.9 (11.3) |
| Male/Female (N) | 40/0 | 3/9 | 23/1 | 4/12 |

*Mean (SD);
SC = subcutaneous;
Q4W = every 4 weeks

AMG 334 dose. There were no apparent differences in PK between healthy subjects and migraineurs.

24-hour ABPM revealed no change in BP circadian rhythm and no increase in BP with increasing doses of AMG

TABLE 10

Pharmacokinetic Parameter Estimates Following AMG 334 Single Administration by Cohort

| Treatment | $C_{max}$ (µg/mL) | $T_{max}$ (day) | $AUC_{last}$ (day × µg/mL) | $AUC_{inf}$ (day × µg/mL) |
|---|---|---|---|---|
| Healthy Subjects | | | | |
| 1 mg SC; n = 3 | 0.008 (0.004) | 4.0 (2.0-7.0) | 0.085 (0.017) | NR |
| 7 mg SC; n = 3 | 0.302 (0.145) | 7.0 (4.0-7.0) | 4.01 (2.07) | 4.13 (2.04) |
| 21 mg SC; n = 6 | 1.17 (0.646) | 7.0 (3.0-10) | 23.5 (15.5) | 24.5 (17.0) |
| 70 mg SC; n = 4-6 | 6.25 (2.03) | 6.0 (3.0-11) | 171 (60.9) | 174 (78.6) |
| 140 mg SC; n = 6 | 9.18 (1.97) | 5.5 (4.0-21) | 332 (57.9) | 333 (57.9) |
| 210 mg SC; n = 6 | 15.2 (4.78) | 8.5 (4.0-11) | 652 (221) | 653 (222) |
| 140 mg IV; n = 6 | 47.8 (4.09) | 0.069 (0.069-0.38) | 614 (112) | 615 (112) |
| Migraine Patients | | | | |
| 140 mg SC; n = 6 | 9.93 (3.42) | 11 (7.0-14) | 367 (102) | 367 (103) |

Data are expressed as mean (SD or range).
$AUC_{inf}$, area under the concentration-time curve from time zero to infinity;
$AUC_{last}$, area under the concentration-time curve from time zero to time of last quantifiable concentration;
$C_{max}$, maximum concentration;
IV, intravenous;
NR, not reported;
SC, subcutaneous;
SD, standard deviation;
$t_{max}$, time to achieve $C_{max}$.

Figure 4A:
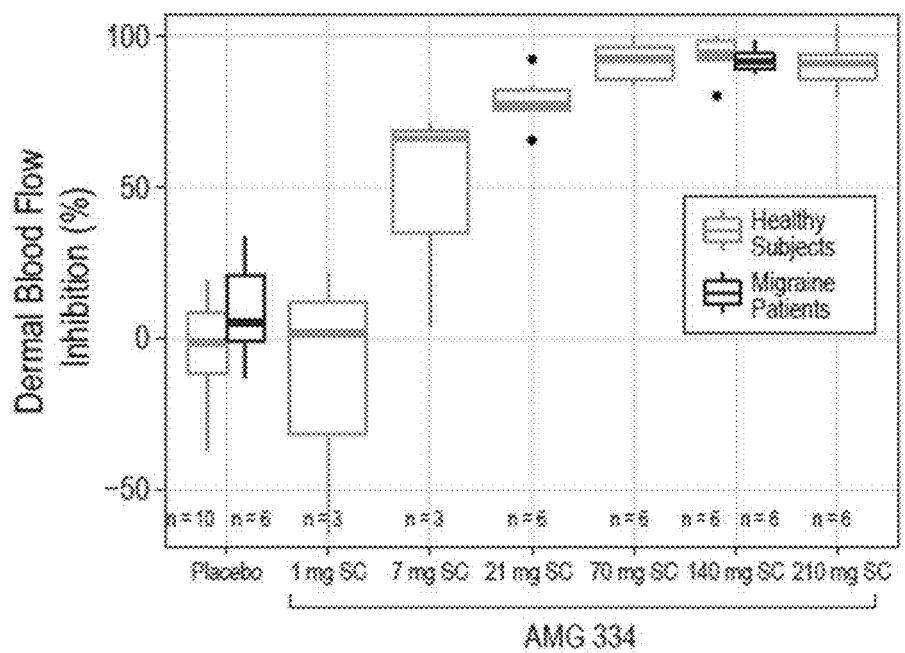
FIG. 4A shows the percentage inhibition of capsaicin-induced dermal blood flow four days after subcutaneous (SC) administration of a single dose of AMG 334 or placebo in healthy subjects and migraine patients in the single, escalating dose study.

Day 4 was the first time point assessed for inhibition of capsaicin-induced DBF in the SD study. On day 4, the percent inhibition of capsaicin-induced increases in DBF compared with placebo for SC doses ≥21 mg ranged from 75% to 95% across the dose range in healthy subjects (91% in migraine subjects). See FIG. 4A. Application of a sigmoidal $E_{max}$ PK/PD model analyzing the relationship between AMG 334 serum exposure and inhibition of capsaicin-induced increase in DBF resulted in an $E_{max}$ of 94.2% (with standard error of 2.85%) and a serum AMG 334 concentration associated with the half maximal effect ($EC_{50}$) of 286 (with standard error of 37.2) ng/mL.

Figure 3B:
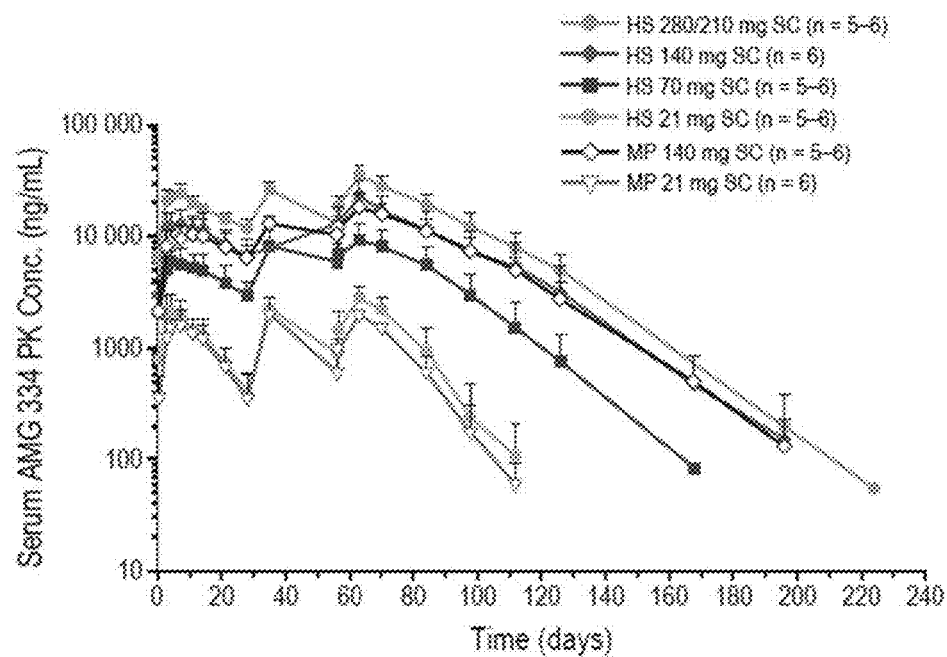
FIG. 3B depicts the mean serum AMG 334 concentration—time profiles in healthy human subjects (HS) and migraine patients (MP) receiving multiple doses on days 1, 29, and 57 of AMG 334 or placebo subcutaneously (SC).

In the MD study, 36 subjects (24 healthy, 12 migraine) received a total of 3 doses of AMG 334 (21 to 280 mg); 12 subjects (8 healthy, 4 migraine) received placebo. After 3 single-dose SC administrations, AMG 334 accumulation ranged from 1.42 to 1.69-fold across doses in healthy subjects and 1.50 to 1.78-fold across doses in migraine patients. See FIG. 3B. $T_{max}$ values ranged from ~3 to 13 days following the first SC dose and ~6 to 14 days following the third dose for all dose ranges (FIG. 3B). Similar to the results of the SD study, there was no apparent difference in PK parameters between healthy subjects and migraineurs.

Figure 4B:
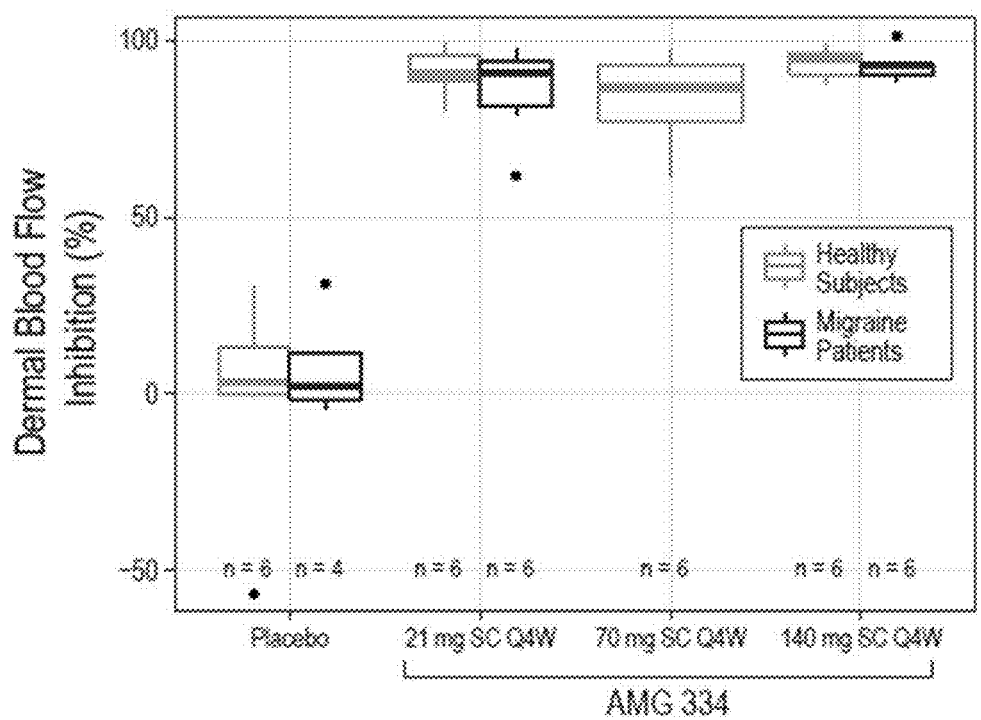
FIG. 4B shows the percentage inhibition of capsaicin-induced dermal blood flow eight days after subcutaneous (SC) administration of the first dose of three of AMG 334 or placebo in healthy subjects and migraine patients in the multiple dose study.

Day 8 was the first time point assessed for inhibition of capsaicin-induced DBF in the MD study. A significant inhibition versus placebo at day 8 was observed across all AMG 334 cohorts in healthy subjects and migraine patients, with no significant difference in drug effect between patient populations. See FIG. 4B. There was no apparent dose dependency in the AMG 334 group in either patient population. Results at days 57 and 85 (healthy subjects) or days 57, 86, and 169 (migraine patients) were consistent with day 8 findings. Later time points (113 days or greater) showed no significant inhibition in the AMG 334 group versus placebo. The DBF inhibition in the MD study was consistent with the SD DBF results and maximum inhibition was maintained during repeated dosing intervals.

334. No statistically significant difference in least squares mean 24-hour and nocturnal BP across all AMG 334 groups versus placebo in healthy subjects was observed. There was also no statistically significant difference in least squares mean 24-hour diastolic and nocturnal diastolic BP across all AMG 334 groups versus placebo in migraine patients. Treatment-emergent adverse events were similar in type and frequency between treatment groups and between healthy subjects and migraineurs. There was no apparent relationship between doses of AMG 334 and the overall incidence of treatment-emergent adverse events. No clinically meaningful differences in vital signs or laboratory values were observed.

The AMG 334 PK profile is consistent with that of other human IgG2 antibodies. PK exposure increased more than dose proportionally from 1 to 70 mg and approximately dose proportionally from 70 to 210 mg after a single administration, with no apparent differences between healthy subjects and migraineurs. After three single-dose SC administrations, similar trends in PK across the dose range in both populations were observed. Administration of AMG 334 resulted in significant inhibition of capsaicin-induced increase in DBF relative to placebo in both healthy subjects and migraine patients, indicating CGRP receptor antagonism. Inhibition of capsaicin-induced increases in DBF was similar between healthy subjects and migraineurs. Single and multiple doses of AMG 334 were well tolerated and there was no association between serum AMG 334 concentration and blood pressure.

Example 3. Results of a Randomized, Double-Blind, Placebo-Controlled, Phase 2 Study to Evaluate the Efficacy and Safety of AMG 334 for the Prevention of Episodic Migraine In this phase 2, double blind, placebo-controlled trial, the effects of AMG 334 (i.e. 4E4 antibody) in preventing episodic migraine were evaluated.

Patients with episodic migraine (≥4 and ≤14 migraine days per month) were randomized to subcutaneous, monthly (QM) placebo or AMG 334 (7 mg, 21 mg, or 70 mg) in a 3:2:2:2 ratio, respectively. The primary endpoint was the change from baseline in monthly migraine days at week 12. Secondary endpoints included the proportion of subjects with ≥50% reduction in monthly migraine days (i.e. 50% responder rate), reduction in monthly migraine attacks, and safety/tolerability. Key exploratory endpoints included reduction in monthly headache days and monthly acute migraine-specific medication (e.g. triptans, ergotamines) use days.

Figure 5:
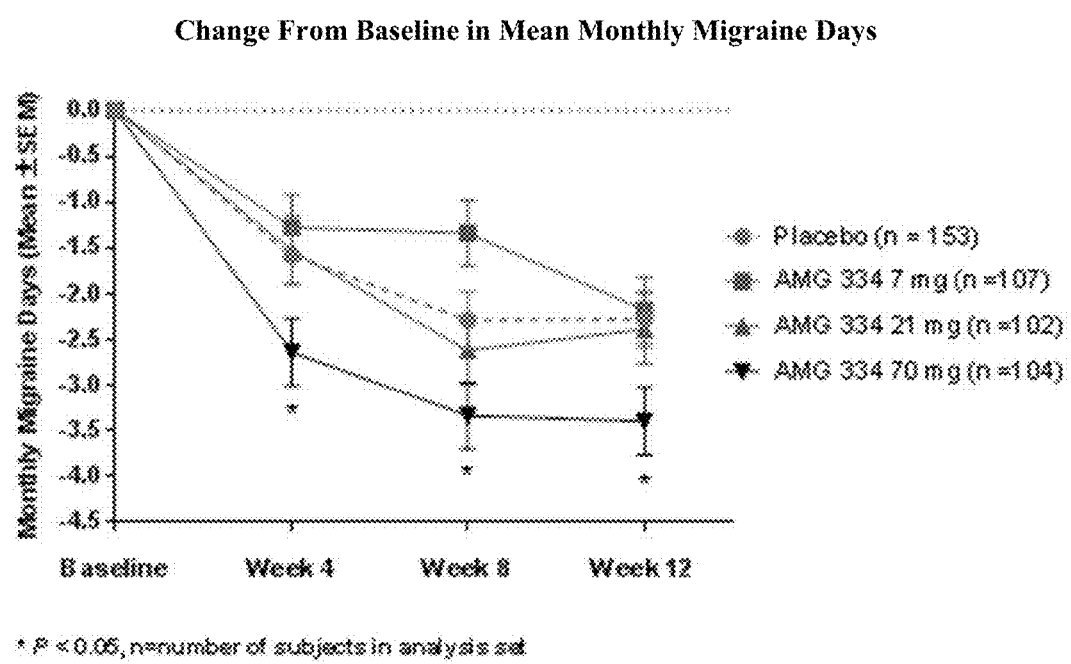
FIG. 5 shows the change from baseline in mean monthly migraine days in episodic migraine patients who received placebo or one of three monthly, subcutaneous doses (7 mg, 21 mg, or 70 mg) of AMG 334, a human monoclonal antibody against the CGRP receptor.
Figure 6:
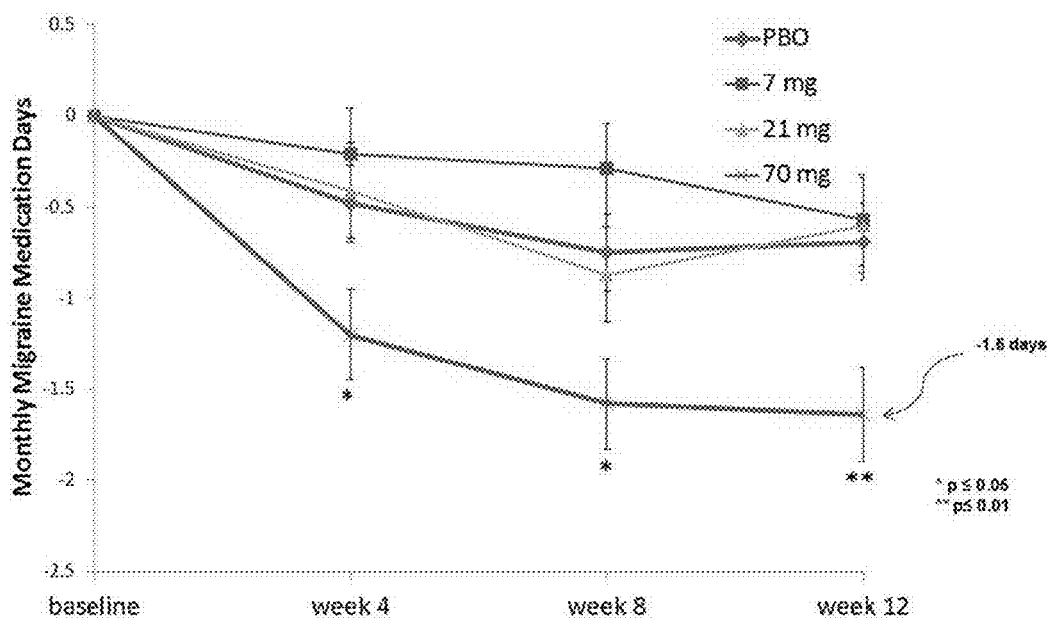
FIG. 6 shows the change from baseline in monthly acute migraine-specific medication (e.g. triptans, ergotamines) use days in episodic migraine patients who received placebo or one of three monthly, subcutaneous doses (7 mg, 21 mg, or 70 mg) of a human monoclonal antibody against the CGRP receptor (AMG 334).
Figure 7A:
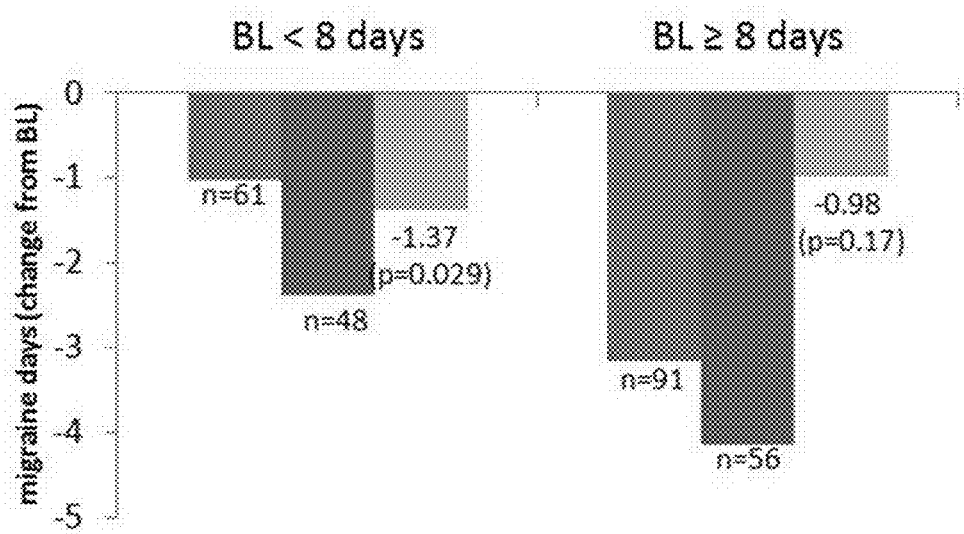
FIG. 7A depicts the change from baseline in mean monthly migraine days in low-frequency episodic migraine patients (less than 8 migraine headache days at baseline) and high-frequency episodic migraine patients (8 or more migraine headache days at baseline) who received placebo or a 70 mg subcutaneous injection of an anti-CGRP receptor antibody (AMG 334) once a month.
Figure 7B:
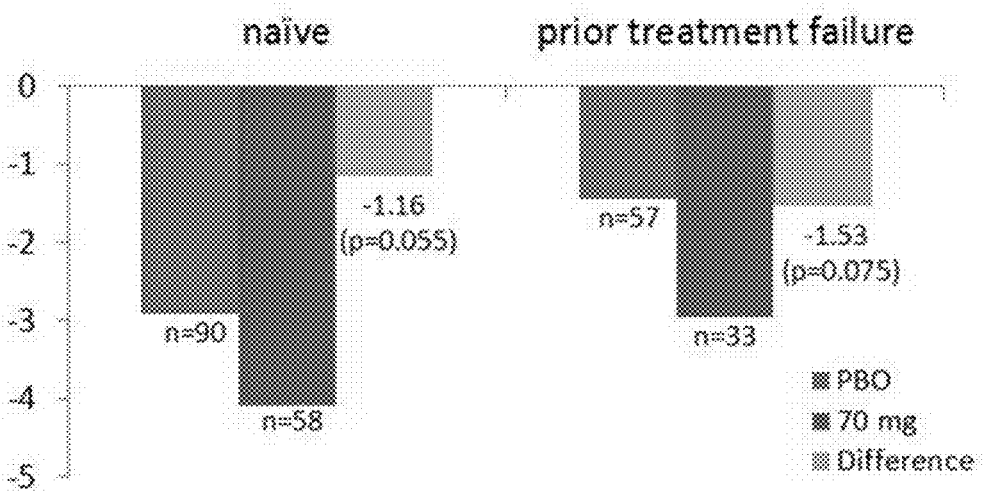
FIG. 7B depicts the change from baseline in mean monthly migraine days in episodic migraine patients who were either treatment-naïve or failed prior prophylactic migraine treatment and received either placebo or a 70 mg subcutaneous injection of an anti-CGRP receptor antibody (AMG 334) once a month.

483 subjects were randomized to placebo (n=160), AMG 334 7 mg (n=108), 21 mg (n=108) or 70 mg (n=107). Subjects were mostly female (80.5%); mean (SD) age was 41.1 (10.8) years. A statistically significant reduction in monthly mean migraine days was observed with AMG 334 70 mg (−3.40) vs placebo (−2.28). See FIG. 5. Post-hoc analysis showed a significant treatment effect as early as week 2. The reduction in monthly migraine days at lower doses of AMG 334 (7 mg: −2.18 and 21 mg: −2.39) was not statistically significant compared with the placebo group (−2.28). See FIG. 5. The 50% responder rate was 46.5% for 70 mg vs 29.9% for placebo (P=0.011) at week 12. Statistically significant reductions in monthly headache days (70 mg: −3.54 vs placebo: −2.39; P=0.022) and monthly acute migraine-specific medication use days (70 mg: −1.64 vs placebo: −0.69; P=0.004; FIG. 6) were also observed. The change in monthly migraine attacks was not statistically significant. Subgroup analyses demonstrated that the efficacy of AMG 334 was similar regardless of sex (data not shown), baseline migraine frequency (FIG. 7A), or prior history of prophylactic medication use (FIG. 7B). A summary of the data for the 70 mg dose of AMG 334 and placebo for various endpoints is shown in Table 11. No major safety findings were reported. The safety/tolerability profile was similar between AMG 334 and placebo. No apparent difference was observed in adverse event incidence rates in the AMG 334 treatment groups compared to placebo. No dose dependency of AMG 334 in adverse event incidence was observed. Six (1.9%) subjects who received AMG 334 vs 2 (1.3%) who received placebo discontinued investigational product due to adverse events during the double-blind treatment phase.

TABLE 11

AMG 334 Efficacy in Episodic Migraine[a]

| | Placebo | AMG 334 70 mg | Difference (95% CI) | p value[b] |
|---|---|---|---|---|
| Primary Endpoint | | | | |
| Monthly migraine days[c] | −2.28 (0.31) | −3.40 (0.37) | −1.12 (−2.06, −0.17) | 0.021 |
| Secondary Endpoints | | | | |
| 50% responder rate | 30% | 47% | 17% | 0.011 |
| Monthly migraine attacks[c] | −1.44 (0.17) | −1.84 (0.20) | −0.40 (−0.92, 0.12) | 0.130 |
| Key Exploratory Endpoints | | | | |
| Monthly headache days[c] | −2.39 (0.32) | −3.54 (0.39) | −1.16 (−2.14, −0.17) | 0.022 |
| Monthly migraine-specific medication use days[c] | −0.69 (0.21) | −1.64 (0.26) | −0.96 (−1.61, −0.30) | 0.004 |
| Headache Impact Test-6 (HIT-6) | −2.95 (0.5) | −4.1 (0.59) | −1.16 (−2.68, 0.35) | 0.130 |
| Migraine Disability Assessment (MIDAS) Total Score | −3.50 (1.8) | −8.80 (2.2) | −5.30 (−10.9, 0.3) | 0.064 |
| MIDAS Presenteeism Score | −1.20 (1.1) | −4.50 (1.3) | −3.30 (−6.5, 0.0) | 0.047 |

[a]Data shown are for week 12
[b]No multiplicity adjustments
[c]Data are change from baseline least square mean (Standard error)

Following the 12-week double-blind (DB) treatment phase of the study, patients were eligible to receive AMG 334 70 mg once a month (QM) during the open-label extension (OLE) phase for up to 256 weeks. During the OLE phase, patients continued to complete a daily diary until week 64. For this interim analysis, patients received AMG 334 70 mg QM up to week 76. Safety and tolerability were evaluated monthly. Efficacy endpoints were analyzed in two groups up to week 64: Group 1: patients who transitioned to AMG 334 70 mg QM after receiving placebo, AMG 334 7 mg, or AMG 334 21 mg in the DB phase (i.e., DB ineffective doses); Group 2: patients who continued to receive AMG 334 70 mg QM during the OLE phase (i.e., DB effective dose). The efficacy endpoints were: change from baseline in monthly migraine days, 50% responder rate, 75% responder rate, 100% responder rate, monthly migraine attacks, monthly migraine-specific medication (e.g. triptans, ergotamines) use days, and monthly headache days.

Figure 8:
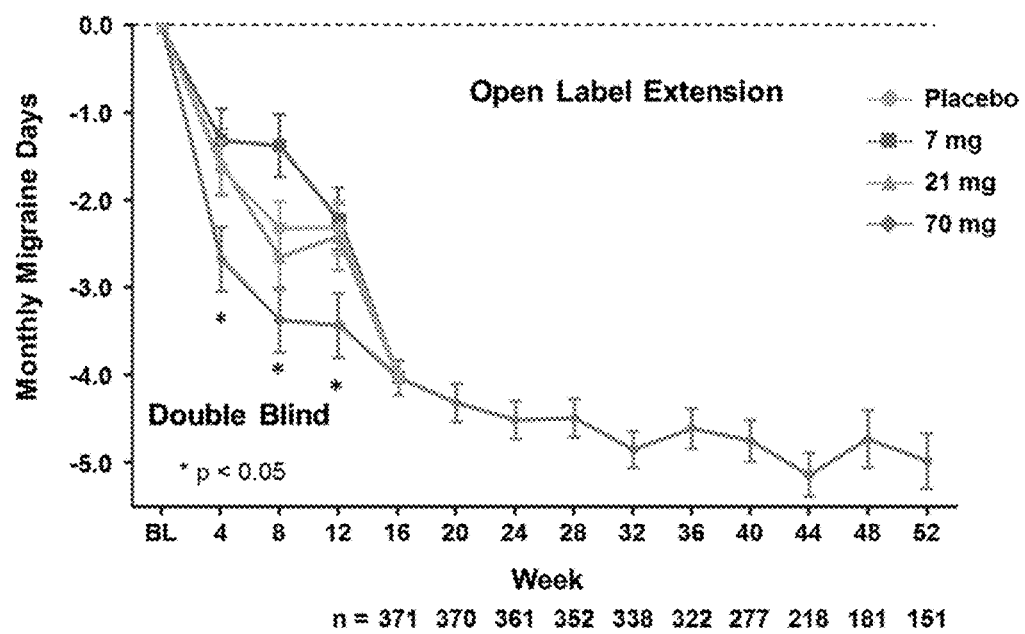
FIG. 8 shows the change from baseline in mean monthly migraine days in episodic migraine patients who received placebo or one of three monthly, subcutaneous doses (7 mg, 21 mg, or 70 mg) of an anti-CGRP receptor antibody (AMG 334). Following the 12-week, double-blind phase of the study, patients in each of the four treatment groups received a 70 mg monthly, subcutaneous dose of the anti-CGRP receptor antibody during the open-label extension phase of the study. Data are shown as least square mean and standard error during the double-blind phase and mean and standard error during the open-label extension phase.
Figure 9A:
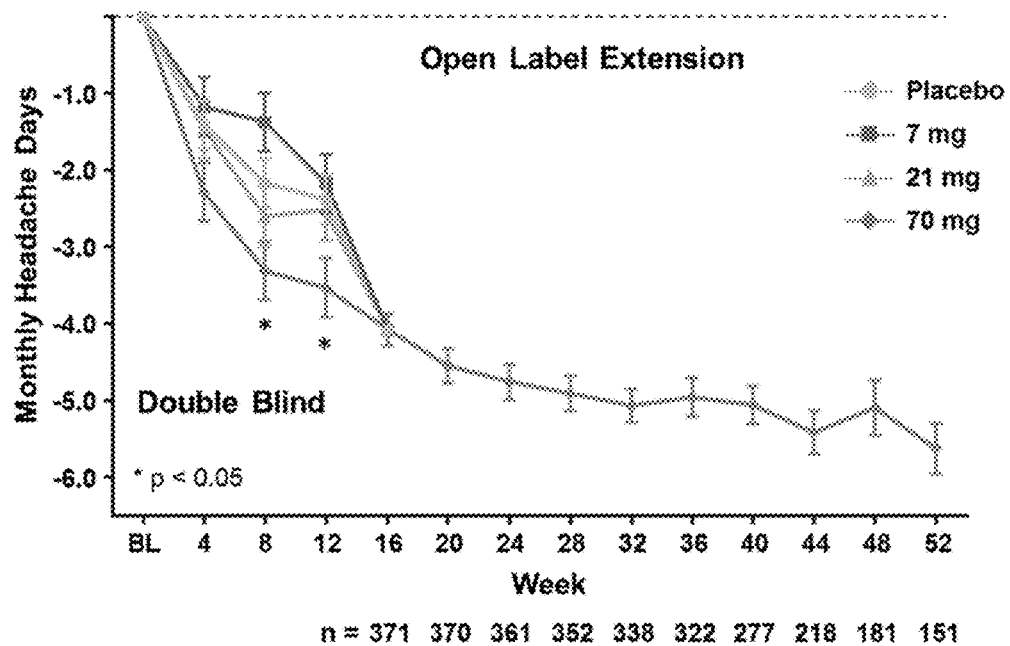
FIG. 9A shows the change from baseline in monthly headache days in episodic migraine patients who received placebo or one of three monthly, subcutaneous doses (7 mg, 21 mg, or 70 mg) of an anti-CGRP receptor antibody (AMG 334). Following the 12-week, double-blind phase of the study, patients in each of the four treatment groups received a 70 mg monthly, subcutaneous dose of the anti-CGRP receptor antibody during the open-label extension phase of the study. Data are shown as least square mean and standard error during the double-blind phase and mean and standard error during the open-label extension phase.
Figure 9B:
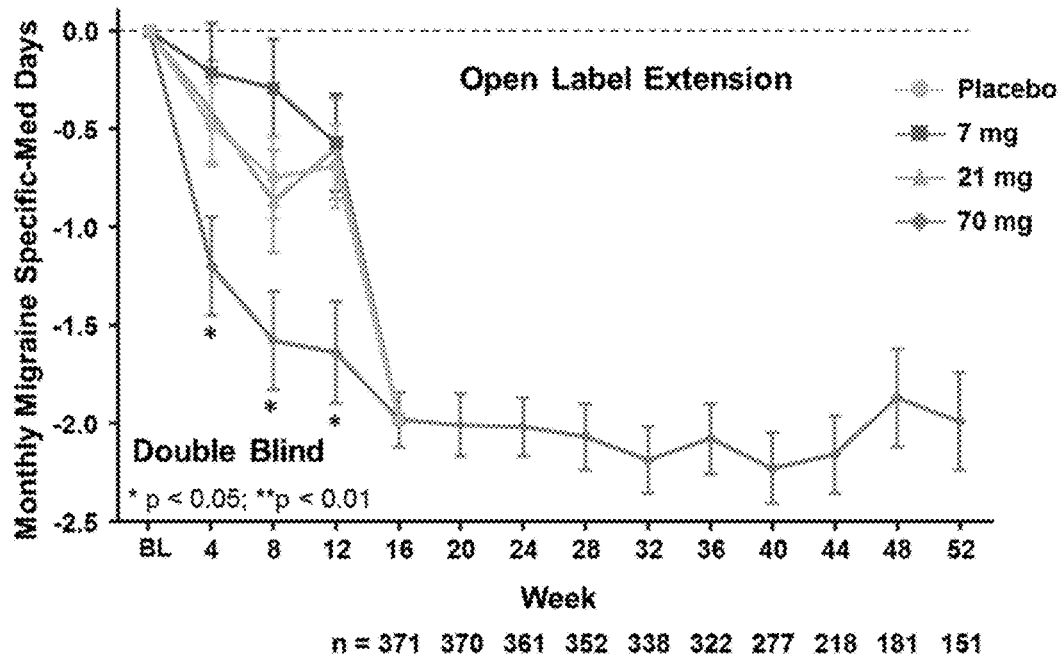
FIG. 9B shows the change from baseline in monthly migraine-specific medication (e.g. triptans, ergotamines) use days in episodic migraine patients who received placebo or one of three monthly, subcutaneous doses (7 mg, 21 mg, or 70 mg) of an anti-CGRP receptor antibody (AMG 334). Following the 12-week, double-blind phase of the study, patients in each of the four treatment groups received a 70 mg monthly, subcutaneous dose of the anti-CGRP receptor antibody during the open-label extension phase of the study. Data are shown as least square mean and standard error during the double-blind phase and mean and standard error during the open-label extension phase.

A total of 383 of 395 (97%) patients who were eligible to enter the OLE received open-label AMG 334 70 mg QM. The median duration of exposure to AMG 334 70 mg in the OLE phase was 239 days (34.1 weeks), with a total exposure of 263.7 patient-years. FIG. 8 depicts the change from baseline in monthly migraine days for the DB phase and the first ten months of the OLE phase. The results show that 70 mg of AMG 334 administered monthly reduced the number of monthly migraine days in patients who previously received placebo, 7 mg AMG 334 or 21 mg AMG 334. Specifically, compared with week 12 of the DB phase (primary endpoint), a further reduction from baseline in mean monthly migraine days was observed during the OLE phase (week 16 to week 64) regardless of DB treatment received (Group 1: −2.4 days at week 12 vs −4.0 days at week 16; Group 2: −3.5 days at week 12 vs −3.9 days at week 16). The treatment effect was sustained during the OLE phase (weeks 16 to 64) with monthly migraine day change from baseline ranging from −4.0 to −6.2 days for Group 1 and −3.7 to −4.9 days for Group 2. Similar results were observed for the 50% responder rate, 75% responder rate, and 100% responder rate, monthly migraine attacks, monthly headache days, and migraine-specific medication use. At week 52, 62% of patients experienced 50% or greater reduction in migraine days, 38% experienced 75% or greater reduction in migraine days, and 19% experienced 100% reduction in migraine days. Compared with week 12 of the DB phase, a further reduction from the study baseline in monthly headache days (FIG. 9A) and migraine-specific medication use days (FIG. 9B) was observed during the OLE phase.

Adverse events (AEs) were reported in 243 of 383 (63%) of patients. The most common AEs (≥3%) were nasopharyngitis, upper respiratory tract infection, arthralgia, influenza, back pain and sinusitis. Most AEs were CTCAE Grade 1 or 2. Serious AEs were reported in 13 patients (3%), of which 1 (<1%) was deemed treatment related (per investigator). Eleven patients (2%) discontinued the OLE phase due to AEs. There were no clinically significant findings on vital signs or laboratory tests (including liver function tests).

The phase 2 study results showed that AMG 334, when administered at a monthly dose of 70 mg, was efficacious in preventing episodic migraine, and AMG 334 had a safety/tolerability profile similar to placebo. Patients who continued to the OLE phase receiving AMG 334 70 mg QM showed a clinically meaningful and sustained reduction in migraine days. Safety and tolerability were consistent with that observed in the DB phase with no new safety signals observed.

Example 4. Randomized, Double-Blind, Placebo-Controlled, Phase 2 Study to Evaluate the Efficacy and Safety of AMG 334 for the Prevention of Chronic Migraine In this phase 2 study, the effects of AMG 334 (i.e. 4E4 antibody) compared to placebo in preventing chronic migraine were evaluated.

Patients with chronic migraine (≥15 headache days per month and ≥8 migraine days per month) were randomized 3:2:2 to receive either placebo, 70 mg AMG 334 subcutaneous (SC) every month (QM) or 140 mg AMG 334 SC QM for the duration of the 12-week double-blind treatment phase. The primary endpoint was the change from baseline in monthly migraine days at week 12. Secondary endpoints included the proportion of subjects with ≥50% reduction in monthly migraine days (i.e. 50% responder rate), reduction in monthly migraine attacks, and safety/tolerability. Key exploratory endpoints included reduction in monthly headache days, change from baseline in monthly cumulative headache hours, reduction from baseline in monthly average severity of migraine pain, and monthly acute migraine-specific medication (e.g. triptans, ergotamines) use days.

After signing informed consent, subjects entered the screening phase (up to 3 weeks), during which eligibility of the subjects was assessed. Eligible subjects included adults between 18 and 65 years of age with history of at least 5 attacks of migraine with or without aura and a history of at least 15 headache days per month of which at least 8 headache days were migraine days in each of the three months prior to screening. Subjects with coexisting Medication Overuse (MO) of triptans, ergot-derivatives, analgesics and combination drug use were eligible for the trial.

All eligible subjects from the screening phase were enrolled into a 4-week baseline phase. Subjects who met the inclusion criteria during the baseline phase were allowed to proceed to the treatment phase. The inclusion criteria for the baseline phase included:

≥15 headache days of which ≥8 headache days meet criteria as migraine days during the baseline phase;

≥4 distinct headache episodes, each lasting ≥4 hours OR if shorter, associated with use of a triptan or ergot-derivative on the same calendar day during the baseline phase; and Demonstrated at least 80% compliance with the eDiary (e.g., must complete eDiary items on at least 23 out of 28 days during the baseline phase).

At the day 1 visit, eligible subjects from the baseline phase were randomized into the 12-week double-blind treatment phase and began to receive double-blind investigational product QM SC. Eligible and enrolled subjects were randomized in a 3:2:2 ratio to either placebo, AMG 334 70 mg or AMG 334 140 mg, with approximately 210 subjects in the placebo group, approximately 140 subjects in the AMG 334 70 mg group and approximately 140 subjects in the AMG 334 140 mg group. The randomization was stratified by region (North America vs Other) and Medication Overuse at Baseline (MO vs non-MO). Double-blind AMG 334 70 mg, AMG 334 140 mg, or placebo was administered during the 12-week double blind treatment phase (i.e., at day 1 and weeks 4 and 8). During the double-blind treatment phase, 2 SC injections were given for each investigational product administration (i.e., day 1, week 4 and week 8). A safety follow-up visit occurs 12 weeks after completion of the study or early termination (i.e., 16 weeks after the last dose of investigational product).

The objective of the final analysis is to evaluate the efficacy and safety of AMG 334 70 mg and AMG 334 140 mg in subjects with chronic migraine. The final analysis for the study is performed at the end of the trial. Efficacy and safety data from the entire study period is analyzed and reported by double-blind treatment group. The results are expected to show that in subjects with chronic migraine, AMG 334 dose-dependently reduces from baseline the monthly migraine days compared with placebo and the adverse event profile of AMG 334 is similar to placebo.

Following the 12-week double-blind treatment phase of the study, an open-label phase was commenced. All subjects who complete the 12-week double-blind treatment phase are eligible for enrollment in the open-label phase during which subjects receive a 70 mg monthly dose of AMG 334 SC for 13 months followed by a 12-week safety follow up visit. Subjects use an electronic diary (eDiary) every day between the Day 1 and month 3 visit, between the month 5 and 6 visit, between the month 9 and 10 visit, and between the month 12 and 13 visit to report information about their migraine and non-migraine headaches and acute medication use.

The objectives of the open-label phase are to characterize the safety, tolerability, and efficacy of long-term administration of AMG 334. Key endpoints include:

change from baseline in monthly migraine days in subjects with chronic migraine;
proportion of subjects with at least 50% reduction from baseline in monthly migraine days;
reduction from baseline in monthly migraine attacks in subjects with chronic migraine;
change in physical impairment over time as measured by the Migraine Physical Function Impact Diary (MPFID); and
change in impact on everyday activities over time as measured by the MPFID.

The open-label study results are expected to show that long-term exposure of AMG 334 is safe and well tolerated in subjects with chronic migraine and the once monthly 70 mg SC dose effectively reduces the number of migraine days in subjects with chronic migraine.

Example 5. A Phase 3, Randomized, Double-Blind, Placebo-Controlled Study to Evaluate the Efficacy and Safety of AMG 334 in Migraine Prevention The primary objective of this study is to evaluate the effect of AMG 334 (i.e. 4E4 antibody) compared to placebo on the change from baseline in mean monthly migraine days, in subjects with episodic migraine. Secondary objectives of the study include the proportion of subjects with at least 50% reduction from baseline in mean monthly migraine days, the change from baseline in mean monthly acute migraine-specific medication treatment days, the change from baseline in physical impairment as measured by the Migraine Physical Function Impact Diary (MPFID), and the change from baseline in impact on everyday activities as measured by the MPFID.

Two doses of AMG 334, 70 and 140 mg, are evaluated in the present study. Subjects receive either AMG 334 140 mg, AMG 334 70 mg, or placebo once monthly (QM) subcutaneously (SC) for 24 weeks in the double-blind treatment phase, followed by a 28-week active treatment phase during which they will receive AMG 334 140 mg or AMG 334 70 mg QM SC. Approximately 852 subjects with episodic migraine (≥4 to <15 migraine days per month) are randomized 1:1:1 to placebo, AMG 334 70 mg, or AMG 334 140 mg. The randomization is stratified by region (North America vs Other) and prior treatment with migraine prophylactic medication (prior migraine prophylactic medication treatment vs. no prior migraine prophylactic medication treatment).

After signing informed consent, subjects enter the screening phase. The screening phase is composed of an initial screening phase (up to 3 weeks) followed by a 4-week baseline phase. During the screening and/or baseline phases, subjects are evaluated for eligibility. Eligible subjects include adults 18 to 65 years of age with history of migraine with or without aura for ≥12 months and who experience ≥4 to <15 migraine days per month with <15 headache days per month on average across the 3 months prior to screening.

At the day 1 visit, eligible subjects are enrolled (i.e., randomized) into the 24-week double-blind treatment phase and begin to receive double-blind investigational product QM SC. At the week 24 visit, subjects in each treatment group are re-randomized 1:1 to AMG 334 70 mg or AMG 334 140 mg for the 28-week active treatment phase and begin to receive investigational product QM SC that remains blinded for the dose level only. The re-randomization is stratified by treatment group assigned during the double-blind phase. Double-blind AMG 334 70 mg, AMG 334 140 mg, or placebo is administered during the 24-week double-blind treatment phase (i.e., at day 1 and weeks 4, 8, 12, 16, and 20) and active AMG 334 70 mg or AMG 334 140 mg is administered during the 28-week active treatment phase (i.e., at weeks 24, 28, 32, 36, 40, 44, and 48). Throughout the double-blind treatment phase and active treatment phase, 2 SC injections are given for each investigational product administration.

A safety follow-up visit occurs 16 weeks after the last dose of investigational product. Subjects use an electronic diary (eDiary) every day throughout the baseline phase, double-blind treatment phase and active treatment phase to report information about their migraine and non-migraine headaches and acute headache medication use. Subjects have scheduled in-clinic study visits monthly from week-4 through the end of the active treatment phase.

The phase 3 study results are expected to show that in subjects with episodic migraine, AMG 334 has a greater reduction from baseline in mean monthly migraine days, compared to placebo. The anticipated treatment effect of AMG 334 compared to placebo is 1.12 and 1.30 monthly migraine days mean reduction from baseline for 70 mg and 140 mg, respectively.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method for preventing or reducing the occurrence of migraine headache in a patient in need thereof comprising administering to the patient by subcutaneous injection once per month a dose of about 70 mg to about 140 mg of an anti-calcitonin gene-related peptide (CGRP) receptor monoclonal antibody or antigen-binding fragment thereof, wherein the anti-CGRP receptor monoclonal antibody or antigen-binding fragment thereof comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65.

2. The method of claim 1, wherein the dose is 70 mg.

3. The method of claim 1, wherein the dose is 140 mg.

4. The method of claim 3, wherein the 140 mg dose is administered as two consecutive injections of 70 mg each.

5. The method of claim 1, wherein the subcutaneous injection is delivered to the patient with a syringe pre-filled with a pharmaceutical composition comprising the anti-CGRP receptor monoclonal antibody or antigen-binding fragment thereof.

6. The method of claim 1, wherein the subcutaneous injection is delivered to the patient with an autoinjector.

7. The method of claim 1, wherein the number of monthly migraine headache days experienced by the patient is reduced following administration of the anti-CGRP receptor monoclonal antibody or antigen-binding fragment thereof as compared to the number of monthly migraine headache days experienced by a patient not receiving the anti-CGRP receptor monoclonal antibody or antigen-binding fragment thereof.

8. The method of claim 1, wherein the number of monthly migraine headache hours experienced by the patient is reduced following administration of the anti-CGRP receptor monoclonal antibody or antigen-binding fragment thereof as compared to the number of monthly migraine headache hours experienced by a patient not receiving the anti-CGRP receptor monoclonal antibody or antigen-binding fragment thereof.

9. The method of claim 1, wherein the number of monthly migraine-specific medication use days experienced by the patient is reduced following administration of the anti-CGRP receptor monoclonal antibody or antigen-binding fragment thereof as compared to the number of monthly migraine-specific medication use days experienced by a patient not receiving the anti-CGRP receptor monoclonal antibody or antigen-binding fragment thereof.

10. The method of claim 1, wherein administration of the anti-CGRP receptor monoclonal antibody or antigen-binding fragment thereof does not substantially cause an adverse side effect in the patient.

11. The method of claim 1, wherein the patient has or is diagnosed with episodic migraine.

12. The method of claim 1, wherein the patient has or is diagnosed with chronic migraine.

13. The method of claim 1, wherein the patient has not previously received prophylactic therapy for migraine headaches.

14. The method of claim 1, wherein the patient has failed or is intolerant to at least one other migraine headache prophylactic therapy.

15. The method of claim 14, wherein the other migraine headache prophylactic therapy is an antiepileptic, a tricyclic antidepressant, or a beta-blocker.

16. The method of claim 1, wherein the anti-CGRP receptor monoclonal antibody or antigen-binding fragment thereof specifically binds to the human CGRP receptor with a $K_D \leq 100$ nM.

17. The method of claim 1, wherein the anti-CGRP receptor monoclonal antibody or antigen-binding fragment thereof comprises a heavy chain variable region ($V_H$) comprising the sequence of SEQ ID NO:92, and a light chain variable region ($V_L$) comprising the sequence of SEQ ID NO:80.

18. The method of claim 1, wherein the anti-CGRP receptor monoclonal antibody comprises a heavy chain comprising the sequence of SEQ ID NO:105, and a light chain comprising the sequence of SEQ ID NO:123.

19. The method of claim 1, wherein the anti-CGRP receptor monoclonal antibody is a monoclonal IgG1 or monoclonal IgG2 antibody.

20. The method of claim 1, wherein the anti-CGRP receptor monoclonal antibody or antigen-binding fragment thereof is administered in a pharmaceutical composition comprising a buffer, a surfactant, and a stabilizing agent.

21. The method of claim 20, wherein the buffer is an acetate buffer.

22. The method of claim 20, wherein the surfactant is polysorbate 20 or polysorbate 80.

23. The method of claim 20, wherein the stabilizing agent is sucrose.

24. The method of claim 1, wherein the dose is administered as a single subcutaneous injection in a volume of about 1 mL or less.

25. A method for prophylactically treating a patient for migraine comprising administering to the patient by subcutaneous injection once per month a dose of about 70 mg to about 140 mg of an anti-CGRP receptor monoclonal antibody or antigen-binding fragment thereof, wherein the anti-CGRP receptor monoclonal antibody or antigen-binding fragment thereof comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65.

26. The method of claim 25, wherein the dose is 70 mg.

27. The method of claim 25, wherein the dose is 140 mg.

28. The method of claim 27, wherein the 140 mg dose is administered as two consecutive injections of 70 mg each.

29. The method of claim 25, wherein the subcutaneous injection is delivered to the patient with a syringe pre-filled with a pharmaceutical composition comprising the anti-CGRP receptor monoclonal antibody or antigen-binding fragment thereof.

30. The method of claim 25, wherein the subcutaneous injection is delivered to the patient with an autoinjector.

31. The method of claim 25, wherein the number of monthly migraine headache days experienced by the patient is reduced following administration of the anti-CGRP receptor monoclonal antibody or antigen-binding fragment thereof as compared to the number of monthly migraine headache days experienced by a patient not receiving the anti-CGRP receptor monoclonal antibody or antigen-binding fragment thereof.

32. The method of claim 25, wherein the number of monthly migraine headache hours experienced by the patient is reduced following administration of the anti-CGRP receptor monoclonal antibody or antigen-binding fragment thereof as compared to the number of monthly migraine headache hours experienced by a patient not receiving the anti-CGRP receptor monoclonal antibody or antigen-binding fragment thereof.

33. The method of claim 25, wherein the number of monthly migraine-specific medication use days experienced by the patient is reduced following administration of the anti-CGRP receptor monoclonal antibody or antigen-binding fragment thereof as compared to the number of monthly migraine-specific medication use days experienced by a patient not receiving the anti-CGRP receptor monoclonal antibody or antigen-binding fragment thereof.

34. The method of claim 25, wherein administration of the anti-CGRP receptor monoclonal antibody or antigen-binding fragment thereof does not substantially cause an adverse side effect in the patient.

35. The method of claim 25, wherein the migraine is episodic migraine.

36. The method of claim 25, wherein the migraine is chronic migraine.

37. The method of claim 25, wherein the patient has not previously received prophylactic therapy for migraine headaches.

38. The method of claim 25, wherein the patient has failed or is intolerant to at least one other migraine headache prophylactic therapy.

39. The method of claim 38, wherein the other migraine headache prophylactic therapy is an antiepileptic, a tricyclic antidepressant, or a beta-blocker.

40. The method of claim 25, wherein the anti-CGRP receptor monoclonal antibody or antigen-binding fragment thereof specifically binds to the human CGRP receptor with a $K_D \leq 100$ nM.

41. The method of claim 25, wherein the anti-CGRP receptor monoclonal antibody or antigen-binding fragment thereof comprises a heavy chain variable region ($V_H$) comprising the sequence of SEQ ID NO:92, and a light chain variable region ($V_L$) comprising the sequence of SEQ ID NO:80.

42. The method of claim 25, wherein the anti-CGRP receptor monoclonal antibody comprises a heavy chain comprising the sequence of SEQ ID NO:105, and a light chain comprising the sequence of SEQ ID NO:123.

43. The method of claim 25, wherein the anti-CGRP receptor monoclonal antibody is a monoclonal IgG1 or monoclonal IgG2 antibody.

44. The method of claim 25, wherein the anti-CGRP receptor monoclonal antibody or antigen-binding fragment thereof is administered in a pharmaceutical composition comprising a buffer, a surfactant, and a stabilizing agent.

45. The method of claim 44, wherein the buffer is an acetate buffer.

46. The method of claim 44, wherein the surfactant is polysorbate 20 or polysorbate 80.

47. The method of claim 44, wherein the stabilizing agent is sucrose.

48. The method of claim 25, wherein the dose is administered as a single subcutaneous injection in a volume of about 1 mL or less.

49. A method for preventing or reducing the occurrence of migraine headache in a patient in need thereof comprising administering to the patient by subcutaneous injection a dose of 70 mg or 140 mg of an anti-CGRP receptor monoclonal antibody once per month, wherein the anti-CGRP receptor monoclonal antibody comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65, and wherein the dose is administered as a single subcutaneous injection in a volume of about 1 mL or less.

50. The method of claim 49, wherein the dose is 70 mg.

51. The method of claim 49, wherein the dose is 140 mg.

52. The method of claim 49, wherein the anti-CGRP receptor monoclonal antibody comprises a heavy chain variable region ($V_H$) comprising the sequence of SEQ ID NO:92, and a light chain variable region ($V_L$) comprising the sequence of SEQ ID NO:80.

53. The method of claim 49, wherein the anti-CGRP receptor monoclonal antibody comprises a heavy chain comprising the sequence of SEQ ID NO:105, and a light chain comprising the sequence of SEQ ID NO:123.

54. A method for prophylactically treating a patient for migraine comprising administering to the patient by subcutaneous injection a dose of 70 mg or 140 mg of an anti-CGRP receptor monoclonal antibody once per month, wherein the anti-CGRP receptor monoclonal antibody comprises a CDRH1 having the sequence of SEQ ID NO:14, a CDRH2 having the sequence of SEQ ID NO:23, a CDRH3 having the sequence of SEQ ID NO:34, a CDRL1 having the sequence of SEQ ID NO:44, a CDRL2 having the sequence of SEQ ID NO:55, and a CDRL3 having the sequence of SEQ ID NO:65, and wherein the dose is administered as a single subcutaneous injection in a volume of about 1 mL or less.

55. The method of claim 54, wherein the dose is 70 mg.

56. The method of claim 54, wherein the dose is 140 mg.

57. The method of claim 54, wherein the anti-CGRP receptor monoclonal antibody comprises a heavy chain variable region ($V_H$) comprising the sequence of SEQ ID NO:92, and a light chain variable region ($V_L$) comprising the sequence of SEQ ID NO:80.

58. The method of claim 54, wherein the anti-CGRP receptor monoclonal antibody comprises a heavy chain comprising the sequence of SEQ ID NO:105, and a light chain comprising the sequence of SEQ ID NO:123.

\* \* \* \* \*

SEQUENCE LISTING

```
<160> NUMBER OF SEQ ID NOS: 136

<210> SEQ ID NO 1
<211> LENGTH: 472
<212> TYPE: PRT
<213> ORGANISM: Homo sapiens

<400> SEQUENCE: 1

Met Leu Tyr Ser Ile Phe His Phe Gly Leu Met Met Glu Lys Lys Cys
1               5                   10                  15

Thr Leu Tyr Phe Leu Val Leu Leu Pro Phe Phe Met Ile Leu Val Thr
            20                  25                  30
```

```
Ala Glu Leu Glu Glu Ser Pro Glu Asp Ser Ile Gln Leu Gly Val Thr
         35                  40                  45

Arg Asn Lys Ile Met Thr Ala Gln Tyr Glu Cys Tyr Gln Lys Ile Met
 50                  55                  60

Gln Asp Pro Ile Gln Gln Ala Glu Gly Val Tyr Cys Asn Arg Thr Trp
 65                  70                  75                  80

Asp Gly Trp Leu Cys Trp Asn Asp Val Ala Ala Gly Thr Glu Ser Met
                 85                  90                  95

Gln Leu Cys Pro Asp Tyr Phe Gln Asp Phe Asp Pro Ser Glu Lys Val
            100                 105                 110

Thr Lys Ile Cys Asp Gln Asp Gly Asn Trp Phe Arg His Pro Ala Ser
            115                 120                 125

Asn Arg Thr Trp Thr Asn Tyr Thr Gln Cys Asn Val Asn Thr His Glu
    130                 135                 140

Lys Val Lys Thr Ala Leu Asn Leu Phe Tyr Leu Thr Ile Ile Gly His
145                 150                 155                 160

Gly Leu Ser Ile Ala Ser Leu Leu Ile Ser Leu Gly Ile Phe Phe Tyr
                165                 170                 175

Phe Lys Ser Leu Ser Cys Gln Arg Ile Thr Leu His Lys Asn Leu Phe
            180                 185                 190

Phe Ser Phe Val Cys Asn Ser Val Val Thr Ile Ile His Leu Thr Ala
            195                 200                 205

Val Ala Asn Asn Gln Ala Leu Val Ala Thr Asn Pro Val Ser Cys Lys
    210                 215                 220

Val Ser Gln Phe Ile His Leu Tyr Leu Met Gly Cys Asn Tyr Phe Trp
225                 230                 235                 240

Met Leu Cys Glu Gly Ile Tyr Leu His Thr Leu Ile Val Val Ala Val
                245                 250                 255

Phe Ala Glu Lys Gln His Leu Met Trp Tyr Tyr Phe Leu Gly Trp Gly
            260                 265                 270

Phe Pro Leu Ile Pro Ala Cys Ile His Ala Ile Ala Arg Ser Leu Tyr
            275                 280                 285

Tyr Asn Asp Asn Cys Trp Ile Ser Ser Asp Thr His Leu Leu Tyr Ile
    290                 295                 300

Ile His Gly Pro Ile Cys Ala Ala Leu Leu Val Asn Leu Phe Phe Leu
305                 310                 315                 320

Leu Asn Ile Val Arg Val Leu Ile Thr Lys Leu Lys Val Thr His Gln
                325                 330                 335

Ala Glu Ser Asn Leu Tyr Met Lys Ala Val Arg Ala Thr Leu Ile Leu
            340                 345                 350

Val Pro Leu Leu Gly Ile Glu Phe Val Leu Ile Pro Trp Arg Pro Glu
            355                 360                 365

Gly Lys Ile Ala Glu Glu Val Tyr Asp Tyr Ile Met His Ile Leu Met
    370                 375                 380

His Phe Gln Gly Leu Leu Val Ser Thr Ile Phe Cys Phe Phe Asn Gly
385                 390                 395                 400

Glu Val Gln Ala Ile Leu Arg Arg Asn Trp Asn Gln Tyr Lys Ile Gln
                405                 410                 415

Phe Gly Asn Ser Phe Ser Asn Ser Glu Ala Leu Arg Ser Ala Ser Tyr
            420                 425                 430

Thr Val Ser Thr Ile Ser Asp Gly Pro Gly Tyr Ser His Asp Cys Pro
            435                 440                 445

Ser Glu His Leu Asn Gly Lys Ser Ile His Asp Ile Glu Asn Val Leu
```

450                 455                 460

Leu Lys Pro Glu Asn Leu Tyr Asn
465                 470

<210> SEQ ID NO 2
<211> LENGTH: 148
<212> TYPE: PRT
<213> ORGANISM: Homo sapiens

<400> SEQUENCE: 2

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
                20                  25                  30

Gly Ala Leu Leu Arg Glu Leu Cys Leu Thr Gln Phe Gln Val Asp Met
            35                  40                  45

Glu Ala Val Gly Glu Thr Leu Trp Cys Asp Trp Gly Arg Thr Ile Arg
        50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
                100                 105                 110

Asp Pro Pro Gly Ser Ile Leu Tyr Pro Phe Ile Val Val Pro Ile Thr
            115                 120                 125

Val Thr Leu Leu Val Thr Ala Leu Val Val Trp Gln Ser Lys Arg Thr
130                 135                 140

Glu Gly Ile Val
145

<210> SEQ ID NO 3
<211> LENGTH: 116
<212> TYPE: PRT
<213> ORGANISM: Homo sapiens

<400> SEQUENCE: 3

Glu Leu Glu Glu Ser Pro Glu Asp Ser Ile Gln Leu Gly Val Thr Arg
1               5                   10                  15

Asn Lys Ile Met Thr Ala Gln Tyr Glu Cys Tyr Gln Lys Ile Met Gln
                20                  25                  30

Asp Pro Ile Gln Gln Ala Glu Gly Val Tyr Cys Asn Arg Thr Trp Asp
            35                  40                  45

Gly Trp Leu Cys Trp Asn Asp Val Ala Ala Gly Thr Glu Ser Met Gln
        50                  55                  60

Leu Cys Pro Asp Tyr Phe Gln Asp Phe Asp Pro Ser Glu Lys Val Thr
65                  70                  75                  80

Lys Ile Cys Asp Gln Asp Gly Asn Trp Phe Arg His Pro Ala Ser Asn
                85                  90                  95

Arg Thr Trp Thr Asn Tyr Thr Gln Cys Asn Val Asn Thr His Glu Lys
                100                 105                 110

Val Lys Thr Ala
            115

<210> SEQ ID NO 4
<211> LENGTH: 137
<212> TYPE: PRT

<213> ORGANISM: Homo sapiens

<400> SEQUENCE: 4

```
Cys Gln Glu Ala Asn Tyr Gly Ala Leu Leu Arg Glu Leu Cys Leu Thr
1               5                   10                  15
Gln Phe Gln Val Asp Met Glu Ala Val Gly Glu Thr Leu Trp Cys Asp
                20                  25                  30
Trp Gly Arg Thr Ile Arg Ser Tyr Arg Glu Leu Ala Asp Cys Cys Gln
            35                  40                  45
Glu Ala Asn Tyr Gly Ala Leu Leu Arg Glu Leu Cys Leu Thr Gln Phe
        50                  55                  60
Gln Val Asp Met Glu Ala Val Gly Glu Thr Leu Trp Cys Asp Trp Gly
65                  70                  75                  80
Arg Thr Ile Arg Ser Tyr Arg Glu Leu Ala Asp Cys Thr Trp His Met
                85                  90                  95
Ala Glu Lys Leu Gly Cys Phe Trp Pro Asn Ala Glu Val Asp Arg Phe
                100                 105                 110
Phe Leu Ala Val His Gly Arg Tyr Phe Arg Ser Cys Pro Ile Ser Gly
            115                 120                 125
Arg Ala Val Arg Asp Pro Pro Gly Ser
        130                 135
```

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

```
Asp Ser Ile Gln Leu Gly Val Thr Arg Asn Lys Ile Met Thr Ala Gln
1               5                   10                  15
Tyr
```

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

```
Asp Val Ala Ala Gly Thr Glu Ser Met Gln Leu Cys Pro
1               5                   10
```

<210> SEQ ID NO 7
<211> LENGTH: 25
<212> TYPE: PRT
<213> ORGANISM: Artificial Sequence
<220> FEATURE:
<223> OTHER INFORMATION: Synthetic peptide

<400> SEQUENCE: 7

```
Asp Gly Asn Trp Phe Arg His Pro Ala Ser Asn Arg Thr Trp Thr Asn
1               5                   10                  15
Tyr Thr Gln Cys Asn Val Asn Thr His
                20                  25
```

<210> SEQ ID NO 8
<211> LENGTH: 8
<212> TYPE: PRT

```
<213> ORGANISM: Artificial Sequence
<220> FEATURE:
<223> OTHER INFORMATION: Synthetic peptide

<400> SEQUENCE: 8

Glu Cys Tyr Gln Lys Ile Met Gln
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asp Gly Trp Leu Cys Trp Asn
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Arg Glu Leu Ala Asp Cys Thr Trp His Met Ala Glu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic peptide

<400> SEQUENCE: 11

Asp Trp Gly Arg Thr Ile Arg Ser Tyr Arg Glu Leu Ala
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Glu Leu Cys Leu Thr Gln Phe Gln Val
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Asp Cys Thr Trp His Met Ala
1               5

<210> SEQ ID NO 14
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 14

Ser Phe Gly Met His
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Asn Ala Trp Met Ser
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide

<400> SEQUENCE: 16

Ser Tyr Ala Met Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Gly Tyr Tyr Met His
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Ser Tyr Gly Met His
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Asp Tyr Ala Met Ser
1               5

<210> SEQ ID NO 20
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 20

Asp Tyr Tyr Met Tyr
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Thr Tyr Ser Met Asn
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide

<400> SEQUENCE: 22

Ser Tyr Gly Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Val Ile Ser Phe Asp Gly Ser Ile Lys Tyr Ser Val Asp Ser Val Lys
1               5                   10                  15

Gly

<210> SEQ ID NO 24
<211> LENGTH: 19
<212> TYPE: PRT
<213> ORGANISM: Artificial Sequence
<220> FEATURE:
<223> OTHER INFORMATION: Synthetic peptide

<400> SEQUENCE: 24

Arg Ile Lys Ser Thr Thr Asp Gly Gly Thr Thr Asp Tyr Ala Ala Pro
1               5                   10                  15

Val Lys Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide

<400> SEQUENCE: 25

Ala Ile Ser Gly Ser Gly Gly Arg Thr Tyr Tyr Ala Asp Ser Val Lys
1               5                   10                  15

Gly
```

```
<210> SEQ ID NO 26
<211> LENGTH: 17
<212> TYPE: PRT
<213> ORGANISM: Artificial Sequence
<220> FEATURE:
<223> OTHER INFORMATION: Synthetic peptide

<400> SEQUENCE: 26

Trp Ile Asn Pro Asn Ser Gly Gly Thr Asn Tyr Ala Gln Lys Phe Gln
1               5                   10                  15
Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic peptide

<400> SEQUENCE: 27

Val Ile Ser Tyr Asp Gly Ser His Glu Ser Tyr Ala Asp Ser Val Lys
1               5                   10                  15
Gly

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide

<400> SEQUENCE: 28

Phe Ile Arg Ser Arg Ala Tyr Gly Gly Thr Pro Glu Tyr Ala Ala Ser
1               5                   10                  15
Val Lys Gly

<210> SEQ ID NO 29
<211> LENGTH: 19
<212> TYPE: PRT
<213> ORGANISM: Artificial Sequence
<220> FEATURE:
<223> OTHER INFORMATION: Synthetic peptide

<400> SEQUENCE: 29

Arg Ile Lys Ser Lys Thr Asp Gly Gly Thr Thr Asp Tyr Thr Ala Pro
1               5                   10                  15
Val Lys Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic peptide

<400> SEQUENCE: 30

Trp Ile Ser Pro Asn Ser Gly Gly Thr Asn Tyr Ala Gln Lys Phe Gln
1               5                   10                  15
Gly

<210> SEQ ID NO 31
<211> LENGTH: 19
<212> TYPE: PRT
<213> ORGANISM: Artificial Sequence
```

```
<220> FEATURE:
<223> OTHER INFORMATION: Synthetic peptide

<400> SEQUENCE: 31

Arg Ile Lys Ser Lys Thr Asp Gly Gly Thr Thr Asp Tyr Ala Ala Pro
1               5                   10                  15

Val Lys Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide

<400> SEQUENCE: 32

Ser Ile Ser Ser Ser Ser Ser Tyr Arg Tyr Tyr Ala Asp Ser Val Lys
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Synthetic peptide

<400> SEQUENCE: 33

Val Ile Trp Tyr Asp Gly Ser Asn Lys Tyr Tyr Ala Asp Ser Val Lys
1               5                   10                  15

Gly

<210> SEQ ID NO 34
<211> LENGTH: 21
<212> TYPE: PRT
<213> ORGANISM: Artificial Sequence
<220> FEATURE:
<223> OTHER INFORMATION: Synthetic peptide

<400> SEQUENCE: 34

Asp Arg Leu Asn Tyr Tyr Asp Ser Ser Gly Tyr Tyr His Tyr Lys Tyr
1               5                   10                  15

Tyr Gly Met Ala Val
                20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Asp Arg Thr Gly Tyr Ser Ile Ser Trp Ser Ser Tyr Tyr Tyr Tyr Tyr
1               5                   10                  15

Gly Met Asp Val
                20

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide
```

<400> SEQUENCE: 36

Asp Gln Arg Glu Val Gly Pro Tyr Ser Ser Gly Trp Tyr Asp Tyr Tyr
1               5                   10                  15

Tyr Gly Met Asp Val
            20

<210> SEQ ID NO 37
<211> LENGTH: 21
<212> TYPE: PRT
<213> ORGANISM: Artificial Sequence
<220> FEATURE:
<223> OTHER INFORMATION: Synthetic peptide

<400> SEQUENCE: 37

Asp Gln Met Ser Ile Ile Met Leu Arg Gly Val Phe Pro Pro Tyr Tyr
1               5                   10                  15

Tyr Gly Met Asp Val
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Glu Arg Lys Arg Val Thr Met Ser Thr Leu Tyr Tyr Tyr Phe Tyr Tyr
1               5                   10                  15

Gly Met Asp Val
            20

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

Gly Arg Gly Ile Ala Ala Arg Trp Asp Tyr
1               5                   10

<210> SEQ ID NO 40
<211> LENGTH: 18
<212> TYPE: PRT
<213> ORGANISM: Artificial Sequence
<220> FEATURE:
<223> OTHER INFORMATION: Synthetic peptide

<400> SEQUENCE: 40

Gly Gly Tyr Ser Gly Tyr Ala Gly Leu Tyr Ser His Tyr Tyr Gly Met
1               5                   10                  15

Asp Val

<210> SEQ ID NO 41
<211> LENGTH: 21
<212> TYPE: PRT
<213> ORGANISM: Artificial Sequence
<220> FEATURE:
<223> OTHER INFORMATION: Synthetic peptide

<400> SEQUENCE: 41

Asp Arg Leu Asn Tyr Tyr Asp Ser Ser Gly Tyr His Tyr Lys Tyr
1               5                   10                  15

Tyr Gly Leu Ala Val
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic peptide

<400> SEQUENCE: 42

Glu Gly Val Ser Gly Ser Ser Pro Tyr Ser Ile Ser Trp Tyr Asp Tyr
1               5                   10                  15

Tyr Tyr Gly Met Asp Val
            20

<210> SEQ ID NO 43
<211> LENGTH: 17
<212> TYPE: PRT
<213> ORGANISM: Artificial Sequence
<220> FEATURE:
<223> OTHER INFORMATION: Synthetic peptide

<400> SEQUENCE: 43

Ala Gly Gly Ile Ala Ala Ala Gly Leu Tyr Tyr Tyr Tyr Gly Met Asp
1               5                   10                  15

Val

<210> SEQ ID NO 44
<211> LENGTH: 13
<212> TYPE: PRT
<213> ORGANISM: Artificial Sequence
<220> FEATURE:
<223> OTHER INFORMATION: Synthetic peptide

<400> SEQUENCE: 44

Ser Gly Ser Ser Ser Asn Ile Gly Asn Asn Tyr Val Ser
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide

<400> SEQUENCE: 45

Ser Gly Ser Ser Ser Asn Ile Gly Ser Asn Tyr Val Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide

<400> SEQUENCE: 46

Arg Ala Ser Gln Gly Ile Arg Asn Asp Leu Gly
1               5                   10

<210> SEQ ID NO 47
<211> LENGTH: 11

```
<212> TYPE: PRT
<213> ORGANISM: Artificial Sequence
<220> FEATURE:
<223> OTHER INFORMATION: Synthetic peptide

<400> SEQUENCE: 47

Gln Gly Asp Ser Leu Arg Ser Phe Tyr Ala Ser
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Synthetic peptide

<400> SEQUENCE: 48

Lys Ser Ser Gln Ser Leu Leu His Ser Ala Gly Lys Thr Tyr Leu Tyr
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic peptide

<400> SEQUENCE: 49

Arg Ser Ser Gln Ser Leu Leu His Ser Phe Gly Tyr Asn Tyr Leu Asp
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Lys Ser Ser Gln Ser Leu Leu His Ser Asp Gly Lys Thr Tyr Leu Tyr
1               5                   10                  15

<210> SEQ ID NO 51
<211> LENGTH: 13
<212> TYPE: PRT
<213> ORGANISM: Artificial Sequence
<220> FEATURE:
<223> OTHER INFORMATION: Synthetic peptide

<400> SEQUENCE: 51

Ser Gly Ser Ser Ser Asn Ile Gly Ser Asn Thr Val Asn
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide

<400> SEQUENCE: 52

Lys Ser Ser Gln Ser Leu Leu His Ser Asp Gly Arg Asn Tyr Leu Tyr
1               5                   10                  15

<210> SEQ ID NO 53
<211> LENGTH: 11
<212> TYPE: PRT
```

```
<213> ORGANISM: Artificial Sequence
<220> FEATURE:
<223> OTHER INFORMATION: Synthetic peptide

<400> SEQUENCE: 53

Arg Ala Ser Gln Gly Ile Arg Lys Asp Leu Gly
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

Arg Ala Ser Gln Ser Val Ser Ser Gly Tyr Leu Thr
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Asp Asn Asn Lys Arg Pro Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Arg Ser Asn Gln Arg Pro Ser
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Ala Ala Ser Ser Leu Gln Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Gly Lys Asn Asn Arg Pro Ser
1               5

<210> SEQ ID NO 59
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 59

Glu Val Ser Asn Arg Phe Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Leu Gly Ser Asn Arg Ala Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Arg Asn Asn Gln Arg Pro Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Thr Asn Asn Gln Arg Pro Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Gly Ala Ser Ser Leu Gln Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Gly Ala Ser Ser Arg Ala Thr
1               5

<210> SEQ ID NO 65
<211> LENGTH: 11
<212> TYPE: PRT
<213> ORGANISM: Artificial Sequence
<220> FEATURE:
```

```
<223> OTHER INFORMATION: Synthetic peptide

<400> SEQUENCE: 65

Gly Thr Trp Asp Ser Arg Leu Ser Ala Val Val
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide

<400> SEQUENCE: 66

Ala Ala Trp Asp Asp Ser Leu Ser Gly Trp Val
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Leu Gln Tyr Asn Ile Tyr Pro Trp Thr
1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic peptide

<400> SEQUENCE: 68

Asn Ser Arg Asp Ser Ser Val Tyr His Leu Val
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Met Gln Ser Phe Pro Leu Pro Leu Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Met Gln Ala Leu Gln Thr Pro Phe Thr
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 71

Ala Ala Arg Asp Glu Ser Leu Asn Gly Val Val
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Leu Gln Tyr Asn Ser Phe Pro Trp Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Gln Gln Tyr Gly Asn Ser Leu Cys Arg
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Gln Gln Tyr Gly Asn Ser Leu Ser Arg
1               5

<210> SEQ ID NO 75
<211> LENGTH: 110
<212> TYPE: PRT
<213> ORGANISM: Artificial Sequence
<220> FEATURE:
<223> OTHER INFORMATION: Synthetic peptide

<400> SEQUENCE: 75

Gln Ser Val Leu Thr Gln Pro Pro Ser Val Ser Glu Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 76
<211> LENGTH: 110

```
<212> TYPE: PRT
<213> ORGANISM: Artificial Sequence
<220> FEATURE:
<223> OTHER INFORMATION: Synthetic polypeptide

<400> SEQUENCE: 76

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Ile Phe Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 77
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Leu Ala Thr Tyr Tyr Cys Leu Gln Tyr Asn Ile Tyr Pro Trp
                85                  90                  95

Thr Phe Gly Gln Gly Thr Lys Val Glu Ile Lys
            100                 105

<210> SEQ ID NO 78
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 78

Ser Ser Glu Leu Thr Gln Asp Pro Thr Val Ser Val Ala Leu Gly Gln
1               5                   10                  15

Thr Val Lys Ile Thr Cys Gln Gly Asp Ser Leu Arg Ser Phe Tyr Ala
            20                  25                  30

Ser Trp Tyr Gln Gln Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
```

```
                50                  55                  60
Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Val Tyr His
                 85                  90                  95

Leu Val Leu Gly Gly Gly Thr Lys Leu Thr Val Leu
            100                 105
```

<210> SEQ ID NO 79
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 79

```
Asp Ile Ile Leu Ala Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
             20                  25                  30

Ala Gly Lys Thr Tyr Leu Tyr Trp Tyr Leu Gln Lys Pro Gly Gln Pro
         35                  40                  45

Pro Gln Leu Leu Ile Tyr Glu Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ser
                 85                  90                  95

Phe Pro Leu Pro Leu Thr Phe Gly Gly Gly Thr Lys Val Glu Ile Lys
            100                 105                 110
```

<210> SEQ ID NO 80
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 80

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
     50                  55                  60

Gly Ser Lys Ser Gly Thr Ser Thr Leu Gly Ile Thr Gly Leu Gln
 65                  70                  75                  80

Thr Gly Asp Glu Ala Asp Tyr Tyr Cys Gly Thr Trp Asp Ser Arg Leu
                 85                  90                  95

Ser Ala Val Val Phe Gly Gly Gly Thr Lys Leu Thr Val Leu
            100                 105                 110
```

<210> SEQ ID NO 81
<211> LENGTH: 112
<212> TYPE: PRT
<213> ORGANISM: Artificial Sequence
<220> FEATURE:

<223> OTHER INFORMATION: Synthetic polypeptide

<400> SEQUENCE: 81

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Phe Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 82

Asp Ile Ile Leu Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Glu Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Met Gln Ser
                85                  90                  95

Phe Pro Leu Pro Leu Thr Phe Gly Gly Gly Thr Lys Val Glu Ile Lys
            100                 105                 110

<210> SEQ ID NO 83
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 83

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln

```
                65                  70                  75                  80
Thr Gly Asp Glu Ala Asp Tyr Tyr Cys Gly Thr Trp Asp Ser Arg Leu
                    85                  90                  95

Ser Ala Val Val Phe Gly Gly Gly Thr Lys Leu Thr Val Leu
                100                 105                 110
```

<210> SEQ ID NO 84
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 84

```
Gln Ser Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Ile Leu Arg Asn Asn Gln Arg Pro Ser Gly Val Pro Asp Arg Phe Ser
50                  55                  60

Gly Ser Lys Ser Gly Thr Ser Ala Ser Leu Thr Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
                100                 105                 110
```

<210> SEQ ID NO 85
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 85

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Phe Tyr Cys Ala Ala Arg Asp Glu Ser Leu
                85                  90                  95

Asn Gly Val Val Phe Gly Gly Gly Thr Lys Leu Thr Val Leu
                100                 105                 110
```

<210> SEQ ID NO 86
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 86

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Ala Ala Pro Lys Leu Leu
                35                  40                  45

Ile Phe Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 87
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 87

Asp Ile Thr Leu Thr Gln Thr Pro Leu Ser Leu Ser Val Ser Pro Gly
1               5                   10                  15

Gln Pro Ala Ser Ile Ser Cys Lys Ser Ser Gln Ser Leu Leu His Ser
                20                  25                  30

Asp Gly Arg Asn Tyr Leu Tyr Trp Tyr Leu Gln Lys Pro Gly Gln Pro
                35                  40                  45

Pro Gln Leu Leu Ile Tyr Glu Val Ser Asn Arg Phe Ser Gly Leu Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Phe Pro Leu Pro Leu Thr Phe Gly Gly Gly Thr Lys Val Glu Ile Lys
            100                 105                 110

<210> SEQ ID NO 88
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 88

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu 85                  90                  95

Ser Ala Val Val Phe Gly Gly Gly Thr Lys Leu Thr Val Leu
            100                 105                 110

<210> SEQ ID NO 89
<211> LENGTH: 107
<212> TYPE: PRT
<213> ORGANISM: Artificial Sequence
<220> FEATURE:
<223> OTHER INFORMATION: Synthetic peptide

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Lys Asp
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Phe Pro Trp
                85                  90                  95

Thr Phe Gly Gln Gly Thr Lys Val Glu Ile Lys
            100                 105

<210> SEQ ID NO 90
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Cys Arg Phe Gly Gln Gly Thr Lys Leu Glu Ile Lys
            100                 105

<210> SEQ ID NO 91
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 91

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser Gly
             20                  25                  30

Tyr Leu Thr Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Asn Ser Leu
                 85                  90                  95

Ser Arg Phe Gly Gln Gly Thr Lys Leu Glu Ile Lys
            100                 105

<210> SEQ ID NO 92
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 92

Gln Val Gln Leu Val Glu Ser Gly Gly Gly Val Val Gln Pro Gly Arg
 1               5                  10                  15

Ser Leu Arg Leu Ser Cys Ala Ser Gly Phe Thr Phe Ser Ser Phe
             20                  25                  30

Gly Met His Trp Val Arg Gln Ala Pro Gly Lys Gly Leu Glu Trp Val
         35                  40                  45

Ala Val Ile Ser Phe Asp Gly Ser Ile Lys Tyr Ser Val Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
        115                 120                 125

Ser Ser
    130

<210> SEQ ID NO 93
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 93

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Thr Thr Asp Gly Gly Thr Thr Asp Tyr Ala Ala
 50                  55                  60

Pro Val Lys Gly Arg Phe Thr Ile Ser Arg Asp Asp Ser Lys Asn Thr
```

```
                65                  70                  75                  80
Leu Tyr Leu Gln Met Asn Ser Leu Lys Thr Glu Asp Thr Ala Val Tyr
                    85                  90                  95

Tyr Cys Thr Thr Asp Arg Thr Gly Tyr Ser Ile Ser Trp Ser Ser Tyr
                    100                 105                 110

Tyr Tyr Tyr Tyr Gly Met Asp Val Trp Gly Gln Gly Thr Thr Val Thr
                    115                 120                 125

Val Ser Ser
    130
```

<210> SEQ ID NO 94
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 94

```
Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Arg Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Arg Glu Val Gly Pro Tyr Ser Ser Gly Trp Tyr Asp
                100                 105                 110

Tyr Tyr Tyr Gly Met Asp Val Trp Gly Gln Gly Thr Thr Val Thr Val
                115                 120                 125

Ser Ser
    130
```

<210> SEQ ID NO 95
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
                50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95
```

```
Ala Arg Asp Gln Met Ser Ile Ile Met Leu Arg Gly Val Phe Pro Pro
            100                 105                 110

Tyr Tyr Tyr Gly Met Asp Val Trp Gly Gln Gly Thr Thr Val Thr Val
            115                 120                 125

Ser Ser
    130
```

<210> SEQ ID NO 96
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 96

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser His Glu Ser Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Arg Lys Arg Val Thr Met Ser Thr Leu Tyr Tyr Tyr Phe
            100                 105                 110

Tyr Tyr Gly Met Asp Val Trp Gly Gln Gly Thr Thr Val Thr Val Ser
        115                 120                 125

Ser
```

<210> SEQ ID NO 97
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 97

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Ile
        35                  40                  45

Gly Phe Ile Arg Ser Arg Ala Tyr Gly Gly Thr Pro Glu Tyr Ala Ala
    50                  55                  60

Ser Val Lys Gly Arg Phe Thr Ile Ser Arg Asp Asp Ser Lys Thr Ile
65                  70                  75                  80

Ala Tyr Leu Gln Met Asn Ser Leu Lys Thr Glu Asp Thr Ala Val Tyr
                85                  90                  95

Phe Cys Ala Arg Gly Arg Gly Ile Ala Ala Arg Trp Asp Tyr Trp Gly
            100                 105                 110

Gln Gly Thr Leu Val Thr Val Ser Ser
        115                 120
```

<210> SEQ ID NO 98
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 98

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Thr Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser
        130
```

<210> SEQ ID NO 99
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Tyr Trp Val Arg Gln Ala Pro Gly Gln Gly Leu Glu Trp Met
        35                  40                  45

Gly Trp Ile Ser Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Gly Gly Tyr Ser Gly Tyr Ala Gly Leu Tyr Ser His Tyr Tyr
            100                 105                 110

Gly Met Asp Val Trp Gly Gln Gly Thr Thr Val Thr Val Ser Ser
        115                 120                 125
```

<210> SEQ ID NO 100
<211> LENGTH: 131
<212> TYPE: PRT
<213> ORGANISM: Artificial Sequence
<220> FEATURE:
<223> OTHER INFORMATION: Synthetic polypeptide

```
<400> SEQUENCE: 100

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Phe Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
            115                 120                 125

Val Ser Ser
    130

<210> SEQ ID NO 101
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 101

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
            115                 120                 125

Val Ser Ser
    130

<210> SEQ ID NO 102
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 102

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
 50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
            100                 105                 110

Lys Tyr Tyr Gly Leu Ala Val Trp Gly Gln Gly Thr Thr Val Thr Val
            115                 120                 125

Ser Ser
    130
```

```
<210> SEQ ID NO 103
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 103

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Arg Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Glu Gly Val Ser Gly Ser Pro Tyr Ser Ile Ser Trp Tyr
            100                 105                 110

Asp Tyr Tyr Tyr Gly Met Asp Val Trp Gly Gln Gly Thr Thr Val Thr
            115                 120                 125

Val Ser Ser
    130
```

```
<210> SEQ ID NO 104
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Trp Tyr Asp Gly Ser Asn Lys Tyr Tyr Ala Asp Ser Val
         50                  55                  60

Lys Gly Arg Phe Ile Ile Ser Arg Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Gly Ile Ala Ala Gly Leu Tyr Tyr Tyr Tyr Gly
             100                 105                 110

Met Asp Val Trp Gly Gln Gly Thr Thr Val Thr Val Ser Ser
             115                 120                 125
```

<210> SEQ ID NO 105
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 105

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Phe
             20                  25                  30

Gly Met His Trp Val Arg Gln Ala Pro Gly Lys Gly Leu Glu Trp Val
             35                  40                  45

Ala Val Ile Ser Phe Asp Gly Ser Ile Lys Tyr Ser Val Asp Ser Val
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Asp Arg Leu Asn Tyr Tyr Asp Ser Ser Gly Tyr Tyr His Tyr
             100                 105                 110

Lys Tyr Tyr Gly Met Ala Val Trp Gly Gln Gly Thr Thr Val Thr Val
             115                 120                 125

Ser Ser Ala Ser Thr Lys Gly Pro Ser Val Phe Pro Leu Ala Pro Cys
     130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                 165                 170                 175

Thr Ser Gly Val His Thr Phe Pro Ala Val Leu Gln Ser Ser Gly Leu
             180                 185                 190

Tyr Ser Leu Ser Ser Val Val Thr Val Pro Ser Ser Asn Phe Gly Thr
         195                 200                 205

Gln Thr Tyr Thr Cys Asn Val Asp His Lys Pro Ser Asn Thr Lys Val
     210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
                 245                 250                 255

Lys Asp Thr Leu Met Ile Ser Arg Thr Pro Glu Val Thr Cys Val Val
             260                 265                 270

Val Asp Val Ser His Glu Asp Pro Glu Val Gln Phe Asn Trp Tyr Val
         275                 280                 285
```

Asp Gly Val Glu Val His Asn Ala Lys Thr Lys Pro Arg Glu Glu Gln
            290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
            325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 106
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Thr Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
            115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
            165                 170                 175

Leu Thr Ser Gly Val His Thr Phe Pro Ala Val Leu Gln Ser Ser Gly
            180                 185                 190

```
Leu Tyr Ser Leu Ser Ser Val Thr Val Pro Ser Ser Asn Phe Gly
            195                 200                 205

Thr Gln Thr Tyr Thr Cys Asn Val Asp His Lys Pro Ser Asn Thr Lys
210                 215                 220

Val Asp Lys Thr Val Glu Arg Lys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Gln Phe Asn Trp Tyr
            275                 280                 285

Val Asp Gly Val Glu Val His Asn Ala Lys Thr Lys Pro Arg Glu Glu
290                 295                 300

Gln Phe Asn Ser Thr Phe Arg Val Val Ser Val Leu Thr Val Val His
305                 310                 315                 320

Gln Asp Trp Leu Asn Gly Lys Glu Tyr Lys Cys Lys Val Ser Asn Lys
                325                 330                 335

Gly Leu Pro Ala Pro Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
450                 455

<210> SEQ ID NO 107
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 107

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Asp Gln Arg Glu Val Gly Pro Tyr Ser Ser Gly Trp Tyr Asp
            100                 105                 110

Tyr Tyr Tyr Gly Met Asp Val Trp Gly Gln Gly Thr Thr Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Asn Phe Gly Thr
        195                 200                 205

Gln Thr Tyr Thr Cys Asn Val Asp His Lys Pro Ser Asn Thr Lys Val
    210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
                325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 108
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 108

-continued

```
Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
            85                  90                  95

Ala Arg Asp Gln Met Ser Ile Ile Met Leu Arg Gly Val Phe Pro Pro
            100                 105                 110

Tyr Tyr Tyr Gly Met Asp Val Trp Gly Gln Gly Thr Thr Val Thr Val
            115                 120                 125

Ser Ser Ala Ser Thr Lys Gly Pro Ser Val Phe Pro Leu Ala Pro Cys
            130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
            165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Asn Phe Gly Thr
            195                 200                 205

Gln Thr Tyr Thr Cys Asn Val Asp His Lys Pro Ser Asn Thr Lys Val
            210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
            275                 280                 285

Asp Gly Val Glu Val His Asn Ala Lys Thr Lys Pro Arg Glu Glu Gln
            290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
            325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
            405                 410                 415
```

```
Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
        450                 455

<210> SEQ ID NO 109
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 109

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser His Glu Ser Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Arg Lys Arg Val Thr Met Ser Thr Leu Tyr Tyr Tyr Phe
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Asn Phe Gly Thr Gln
        195                 200                 205

Thr Tyr Thr Cys Asn Val Asp His Lys Pro Ser Asn Thr Lys Val Asp
    210                 215                 220

Lys Thr Val Glu Arg Lys Cys Cys Val Glu Cys Pro Pro Cys Pro Ala
225                 230                 235                 240

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Phe Arg Val Val Ser Val Leu Thr Val Val His Gln Asp
305                 310                 315                 320
```

```
Trp Leu Asn Gly Lys Glu Tyr Lys Cys Lys Val Ser Asn Lys Gly Leu
            325                 330                 335

Pro Ala Pro Ile Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 110
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 110

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Ile
        35                  40                  45

Gly Phe Ile Arg Ser Arg Ala Tyr Gly Gly Thr Pro Glu Tyr Ala Ala
    50                  55                  60

Ser Val Lys Gly Arg Phe Thr Ile Ser Arg Asp Asp Ser Lys Thr Ile
65                  70                  75                  80

Ala Tyr Leu Gln Met Asn Ser Leu Lys Thr Glu Asp Thr Ala Val Tyr
                85                  90                  95

Phe Cys Ala Arg Gly Arg Gly Ile Ala Ala Arg Trp Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220
```

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 111
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Thr Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Ala Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser Ala Ser Thr Lys Gly Pro Ser Val Phe Pro Leu Ala Pro
    130                 135                 140

```
Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
            165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Asn Phe Gly
            195                 200                 205

Thr Gln Thr Tyr Thr Cys Asn Val Asp His Lys Pro Ser Asn Thr Lys
            210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Gln Phe Asn Trp Tyr
            275                 280                 285

Val Asp Gly Val Glu Val His Asn Ala Lys Thr Lys Pro Arg Glu Glu
            290                 295                 300

Gln Phe Asn Ser Thr Phe Arg Val Val Ser Val Leu Thr Val Val His
305                 310                 315                 320

Gln Asp Trp Leu Asn Gly Lys Glu Tyr Lys Cys Lys Val Ser Asn Lys
            325                 330                 335

Gly Leu Pro Ala Pro Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 112
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Tyr Trp Val Arg Gln Ala Pro Gly Gln Gly Leu Glu Trp Met
        35                  40                  45
```

```
Gly Trp Ile Ser Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Gly Gly Tyr Ser Gly Tyr Ala Gly Leu Tyr Ser His Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
        195                 200                 205

Thr Cys Asn Val Asp His Lys Pro Ser Asn Thr Lys Val Asp Lys Thr
    210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
450
```

-continued

<210> SEQ ID NO 113
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 113

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Phe Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Phe Arg Val Val Ser Val Leu Thr Val Val His
305                 310                 315                 320

Gln Asp Trp Leu Asn Gly Lys Glu Tyr Lys Cys Lys Val Ser Asn Lys
                325                 330                 335

Gly Leu Pro Ala Pro Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
```

```
                    370                 375                 380
Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                    405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
            435                 440                 445

Lys Ser Leu Ser Leu Ser Pro Gly Lys
        450                 455

<210> SEQ ID NO 114
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 114

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Arg Thr Gly Tyr Ser Ile Ser Trp Ser Ser Tyr
            100                 105                 110

Tyr Tyr Tyr Tyr Gly Met Asp Val Trp Gly Gln Gly Thr Thr Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Asn Phe Gly
        195                 200                 205

Thr Gln Thr Tyr Thr Cys Asn Val Asp His Lys Pro Ser Asn Thr Lys
    210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Gln Phe Asn Trp Tyr
```

```
                275                 280                 285
Val Asp Gly Val Glu Val His Asn Ala Lys Thr Lys Pro Arg Glu Glu
        290                 295                 300

Gln Phe Asn Ser Thr Phe Arg Val Val Ser Val Leu Thr Val Val His
305                 310                 315                 320

Gln Asp Trp Leu Asn Gly Lys Glu Tyr Lys Cys Lys Val Ser Asn Lys
                325                 330                 335

Gly Leu Pro Ala Pro Ile Glu Lys Thr Ile Ser Lys Thr Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 115
<211> LENGTH: 456
<212> TYPE: PRT
<213> ORGANISM: Artificial Sequence
<220> FEATURE:
<223> OTHER INFORMATION: Synthetic polypeptide

<400> SEQUENCE: 115

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Leu Asn Tyr Tyr Asp Ser Ser Gly Tyr Tyr His Tyr
            100                 105                 110

Lys Tyr Tyr Gly Leu Ala Val Trp Gly Gln Gly Thr Thr Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
```

```
                180                 185                 190
Tyr Ser Leu Ser Ser Val Val Thr Val Pro Ser Ser Asn Phe Gly Thr
            195                 200                 205

Gln Thr Tyr Thr Cys Asn Val Asp His Lys Pro Ser Asn Thr Lys Val
        210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Gln Phe Asn Trp Tyr Val
    275                 280                 285

Asp Gly Val Glu Val His Asn Ala Lys Thr Lys Pro Arg Glu Glu Gln
290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
            325                 330                 335

Leu Pro Ala Pro Ile Glu Lys Thr Ile Ser Lys Thr Lys Gly Gln Pro
        340                 345                 350

Arg Glu Pro Gln Val Tyr Thr Leu Pro Pro Ser Arg Glu Glu Met Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
        450                 455

<210> SEQ ID NO 116
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 116

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Arg Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
```

85                  90                  95
Ala Arg Glu Gly Val Ser Gly Ser Pro Tyr Ser Ile Ser Trp Tyr
                100                 105                 110

Asp Tyr Tyr Gly Met Asp Val Trp Gly Gln Gly Thr Thr Val Thr
                115                 120                 125

Val Ser Ser Ala Ser Thr Lys Gly Pro Ser Val Phe Pro Leu Ala Pro
130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Asn Phe Gly
                195                 200                 205

Thr Gln Thr Tyr Thr Cys Asn Val Asp His Lys Pro Ser Asn Thr Lys
210                 215                 220

Val Asp Lys Thr Val Glu Arg Lys Cys Cys Val Glu Cys Pro Pro Cys
225                 230                 235                 240

Pro Ala Pro Pro Val Ala Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Gln Phe Asn Trp Tyr
                275                 280                 285

Val Asp Gly Val Glu Val His Asn Ala Lys Thr Lys Pro Arg Glu Glu
                290                 295                 300

Gln Phe Asn Ser Thr Phe Arg Val Val Ser Val Leu Thr Val Val His
305                 310                 315                 320

Gln Asp Trp Leu Asn Gly Lys Glu Tyr Lys Cys Lys Val Ser Asn Lys
                325                 330                 335

Gly Leu Pro Ala Pro Ile Glu Lys Thr Ile Ser Lys Thr Lys Gly Gln
                340                 345                 350

Pro Arg Glu Pro Gln Val Tyr Thr Leu Pro Pro Ser Arg Glu Glu Met
                355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
450                 455

<210> SEQ ID NO 117
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 117

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Ile Ile Ser Arg Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Gly Ile Ala Ala Gly Leu Tyr Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 118
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 118

Gln Ser Val Leu Thr Gln Pro Pro Ser Val Ser Glu Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 119
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 119

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Ala Ala Pro Lys Leu Leu

```
                35                  40                  45
Ile Phe Arg Ser Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Gly Trp Val Phe Gly Gly Gly Thr Lys Leu Thr Val Leu Gly Gln
                100                 105                 110
Pro Lys Ala Asn Pro Thr Val Thr Leu Phe Pro Pro Ser Ser Glu Glu
            115                 120                 125
Leu Gln Ala Asn Lys Ala Thr Leu Val Cys Leu Ile Ser Asp Phe Tyr
            130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
            195                 200                 205
Thr Val Ala Pro Thr Glu Cys Ser
            210                 215

<210> SEQ ID NO 120
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 120

Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Arg Asn Asp
             20                  25                  30
Leu Gly Trp Phe Gln Gln Lys Pro Gly Lys Ala Pro Lys Arg Leu Ile
         35                  40                  45
Tyr Ala Ala Ser Ser Leu Gln Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Glu Asp Leu Ala Thr Tyr Tyr Cys Leu Gln Tyr Asn Ile Tyr Pro Trp
                 85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
```

```
                180              185              190
Ala Cys Glu Val Thr His Gln Gly Leu Ser Ser Pro Val Thr Lys Ser
            195              200              205

Phe Asn Arg Gly Glu Cys
    210

<210> SEQ ID NO 121
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 121

Ser Ser Glu Leu Thr Gln Asp Pro Thr Val Ser Val Ala Leu Gly Gln
1               5                   10                  15

Thr Val Lys Ile Thr Cys Gln Gly Asp Ser Leu Arg Ser Phe Tyr Ala
            20                  25                  30

Ser Trp Tyr Gln Gln Lys Pro Gly Gln Ala Pro Val Leu Val Phe Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Val Tyr His
                85                  90                  95

Leu Val Leu Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 122
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 122

Asp Ile Ile Leu Ala Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Ala Gly Lys Thr Tyr Leu Tyr Trp Tyr Leu Gln Lys Pro Gly Gln Pro
        35                  40                  45
```

```
Pro Gln Leu Leu Ile Tyr Glu Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ser
                 85                  90                  95

Phe Pro Leu Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 123
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 123

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Ser Thr Leu Gly Ile Thr Gly Leu Gln
 65                  70                  75                  80

Thr Gly Asp Glu Ala Asp Tyr Tyr Cys Gly Thr Trp Asp Ser Arg Leu
                 85                  90                  95

Ser Ala Val Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190
```

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 124
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 124

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Phe Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 125
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 125

Asp Ile Ile Leu Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Glu Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Met Gln Ser
                85                  90                  95

Phe Pro Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 126
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 126

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

-continued

Thr Val Ala Pro Thr Glu Cys Ser
        210                 215

<210> SEQ ID NO 127
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 127

Gln Ser Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Ile Leu Arg Asn Asn Gln Arg Pro Ser Gly Val Pro Asp Arg Phe Ser
    50                  55                  60

Gly Ser Lys Ser Gly Thr Ser Ala Ser Leu Thr Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 128
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 128

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln

```
                65                  70                  75                  80
Ser Glu Asp Glu Ala Asp Phe Tyr Cys Ala Ala Arg Asp Glu Ser Leu
                    85                  90                  95

Asn Gly Val Val Phe Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 129
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 129

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Ala Ala Pro Lys Leu Leu
            35                  40                  45

Ile Phe Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
```

<210> SEQ ID NO 130
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 130

```
Asp Ile Thr Leu Thr Gln Thr Pro Leu Ser Leu Ser Val Ser Pro Gly
1               5                   10                  15

Gln Pro Ala Ser Ile Ser Cys Lys Ser Ser Gln Ser Leu Leu His Ser
            20                  25                  30

Asp Gly Arg Asn Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Leu Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Phe Pro Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 131
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 131

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80
```

```
Thr Gly Asp Glu Ala Asp Tyr Tyr Cys Gly Thr Trp Asp Ser Arg Leu
                85                  90                  95

Ser Ala Val Val Phe Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 132
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Lys Asp
            20                  25                  30

Leu Gly Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 133
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Tyr Leu Thr Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95

Cys Arg Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 134
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 134

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Tyr Leu Thr Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
                85                  90                  95
```

```
Ser Arg Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 135
<211> LENGTH: 22
<212> TYPE: PRT
<213> ORGANISM: Artificial Sequence
<220> FEATURE:
<223> OTHER INFORMATION: Synthetic peptide

<400> SEQUENCE: 135

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide

<400> SEQUENCE: 136

Met Glu Thr Pro Ala Gln Leu Leu Phe Leu Leu Leu Leu Trp Leu Pro
1               5                   10                  15

Asp Thr Thr Gly
            20
```